(12) United States Patent
Otto et al.

(10) Patent No.: US 11,229,485 B2
(45) Date of Patent: Jan. 25, 2022

(54) PREOPERATIVE PLANNING AND ASSOCIATED INTRAOPERATIVE REGISTRATION FOR A SURGICAL SYSTEM

(71) Applicant: MAKO Surgical Corp., Fort Lauderdale, FL (US)

(72) Inventors: Jason Karl Otto, Sioux Falls, SD (US); Abdullah Zafar Abbasi, Plantation, FL (US); Milan Ikits, Davie, FL (US); Daniel Perez, Plantation, FL (US); Shang Mu, Princeton, NJ (US); Xiping Li, Weston, FL (US); Ta-Cheng Chang, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 277 days.

(21) Appl. No.: 16/436,102

(22) Filed: Jun. 10, 2019

(65) Prior Publication Data
US 2019/0321105 A1 Oct. 24, 2019

Related U.S. Application Data

(62) Division of application No. 15/167,771, filed on May 27, 2016, now Pat. No. 10,357,315.

(51) Int. Cl.
*A61B 34/10* (2016.01)
*A61B 5/055* (2006.01)
(Continued)

(52) U.S. Cl.
CPC ............ *A61B 34/10* (2016.02); *A61B 5/0037* (2013.01); *A61B 5/055* (2013.01); *A61B 5/1075* (2013.01);
(Continued)

(58) Field of Classification Search
CPC .................................... A61B 34/10–2034/108
See application file for complete search history.

(56) References Cited

U.S. PATENT DOCUMENTS

| 8,876,830 | B2 * | 11/2014 | Hodorek | .............. | A61B 17/157 606/87 |
| 2011/0196377 | A1 * | 8/2011 | Hodorek | .............. | A61B 17/157 606/87 |

(Continued)

*Primary Examiner* — Zade Coley
(74) *Attorney, Agent, or Firm* — Polsinelli PC

(57) ABSTRACT

Aspects of the disclosure may involve a method of generating resection plane data for use in planning an arthroplasty procedure on a patient bone. The method may include: obtaining patient data associated with at least a portion of the patient bone, the patient data captured using a medical imaging machine; generating a three-dimensional patient bone model from the patient data, the patient bone model including a polygonal surface mesh; identifying a location of a posterior point on the polygonal surface mesh; creating a three-dimensional shape centered at or near the location; identifying a most posterior vertex of all vertices of the polygonal surface mesh that may be enclosed by the three-dimensional shape; using the most posterior vertex as a factor for determining a posterior resection depth; and generating resection data using the posterior resection depth, the resection data configured to be utilized by a navigation system during the arthroplasty procedure.

22 Claims, 35 Drawing Sheets

(51) Int. Cl.
  *A61B 5/00*    (2006.01)
  *A61B 5/107*   (2006.01)
  *A61B 34/30*   (2016.01)
  *A61F 2/46*    (2006.01)
  *A61B 34/20*   (2016.01)
  *A61B 34/32*   (2016.01)

(52) U.S. Cl.
  CPC .......... *A61B 5/1077* (2013.01); *A61B 34/30* (2016.02); *A61B 34/32* (2016.02); *A61B 2034/104* (2016.02); *A61B 2034/105* (2016.02); *A61B 2034/107* (2016.02); *A61B 2034/108* (2016.02); *A61B 2034/2055* (2016.02); *A61B 2034/2068* (2016.02); *A61B 2505/05* (2013.01); *A61B 2576/02* (2013.01); *A61F 2002/4662* (2013.01)

(56) References Cited

U.S. PATENT DOCUMENTS

| | | | |
|---|---|---|---|
| 2011/0214279 A1* | 9/2011 | Park | G06T 7/0012 29/592 |
| 2013/0211531 A1* | 8/2013 | Steines | A61F 2/3859 623/20.35 |
| 2014/0228860 A1* | 8/2014 | Steines | A61B 34/30 606/130 |
| 2016/0228197 A1* | 8/2016 | Park | G06T 19/20 |

\* cited by examiner

FIG. 1
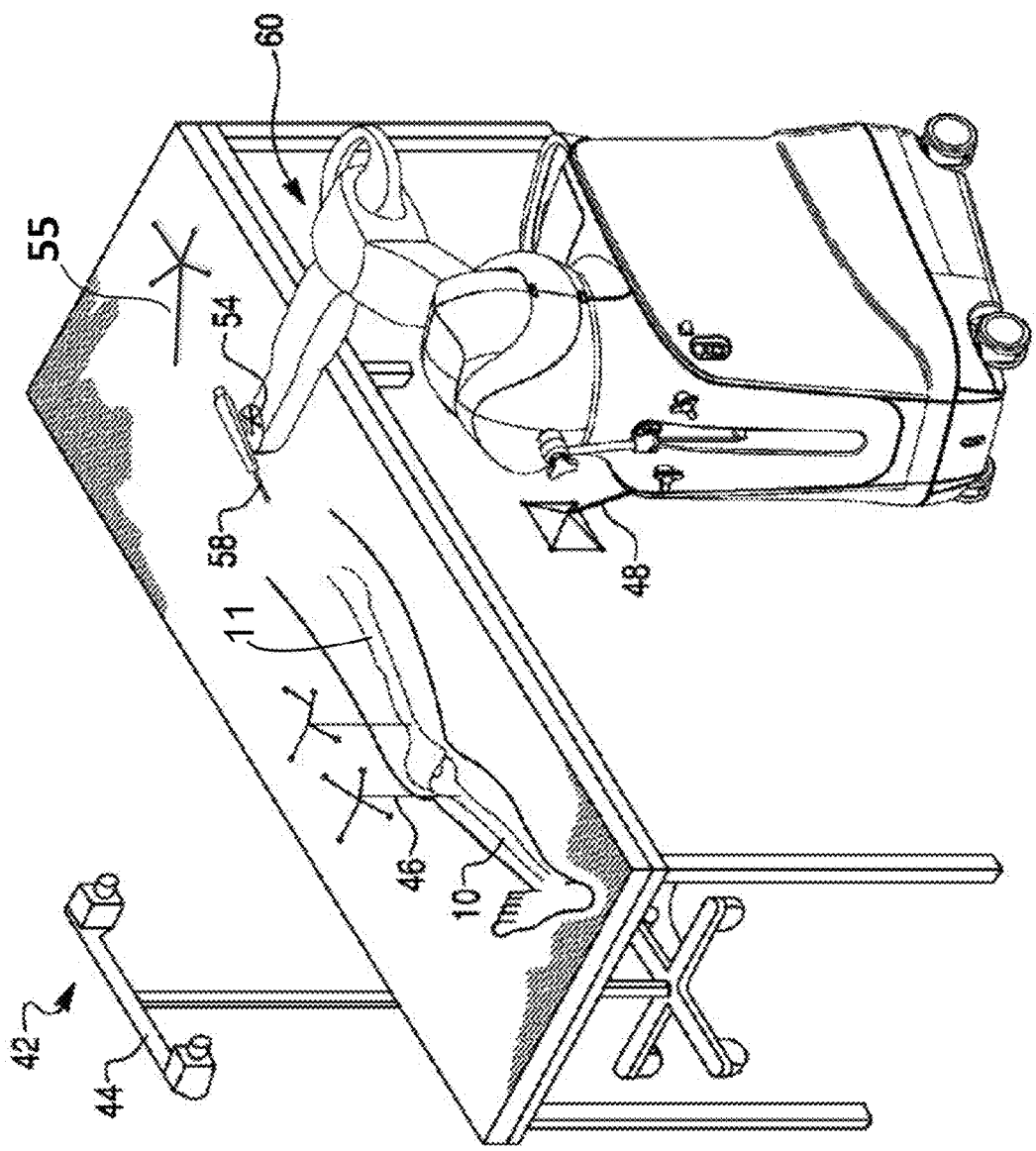
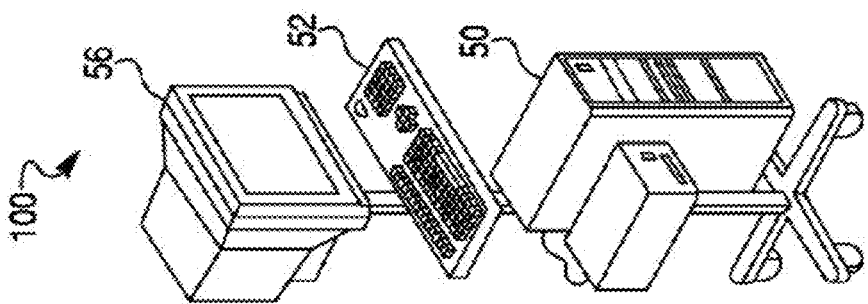

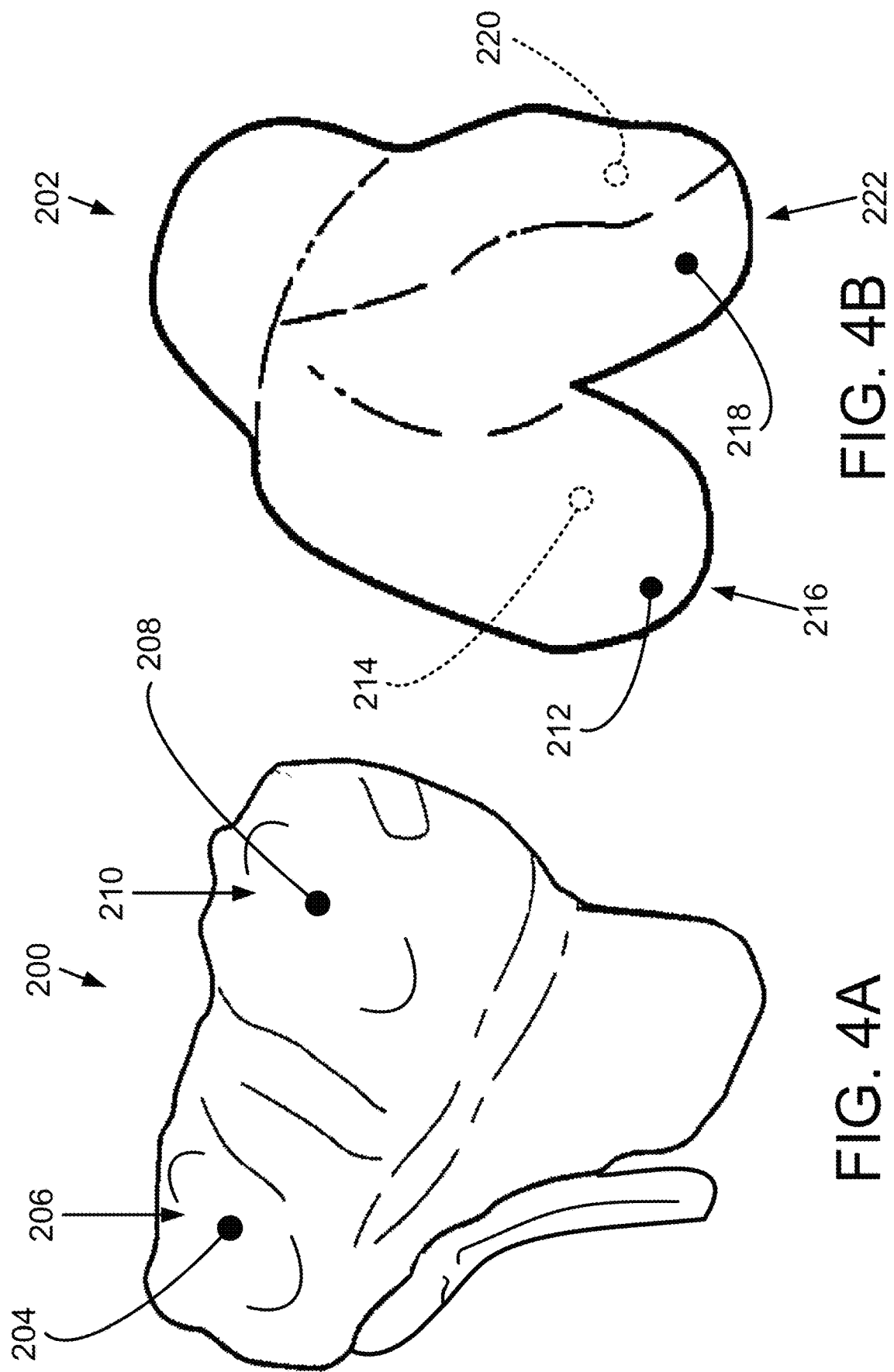

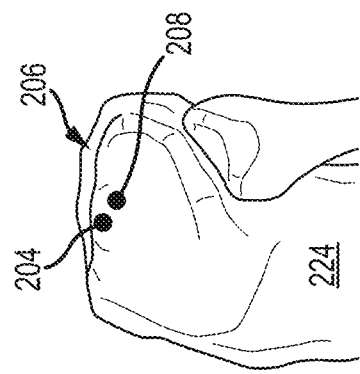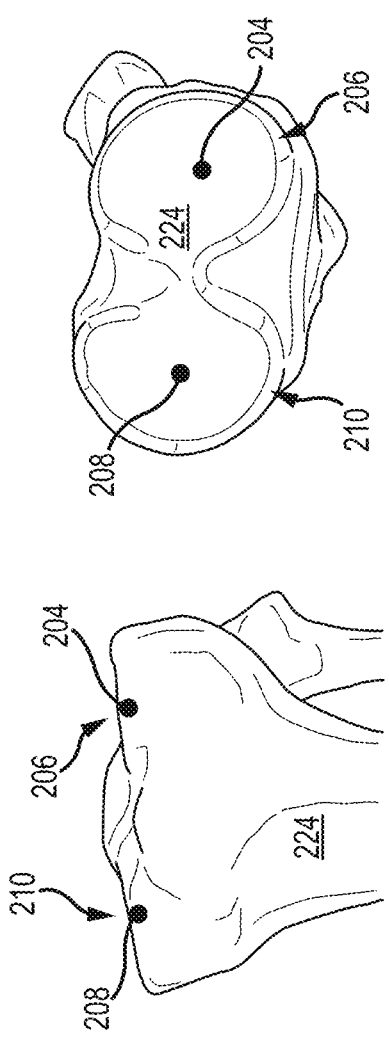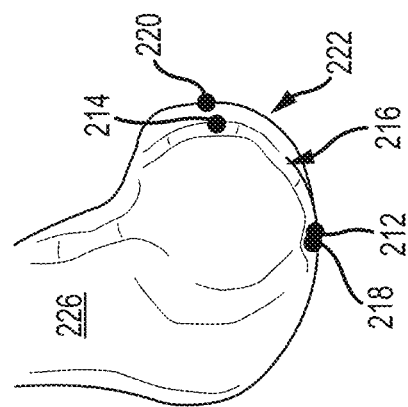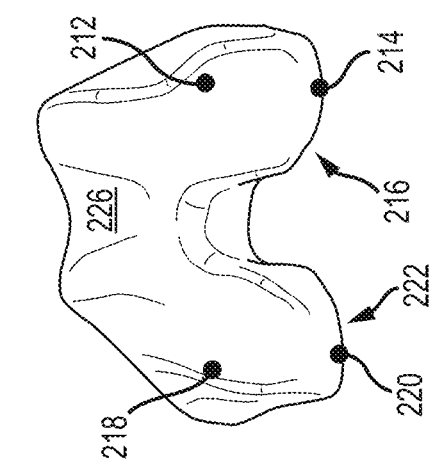

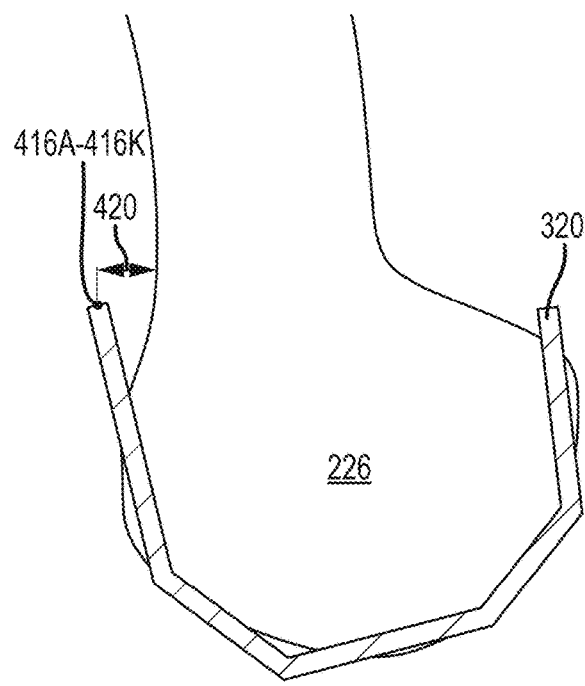
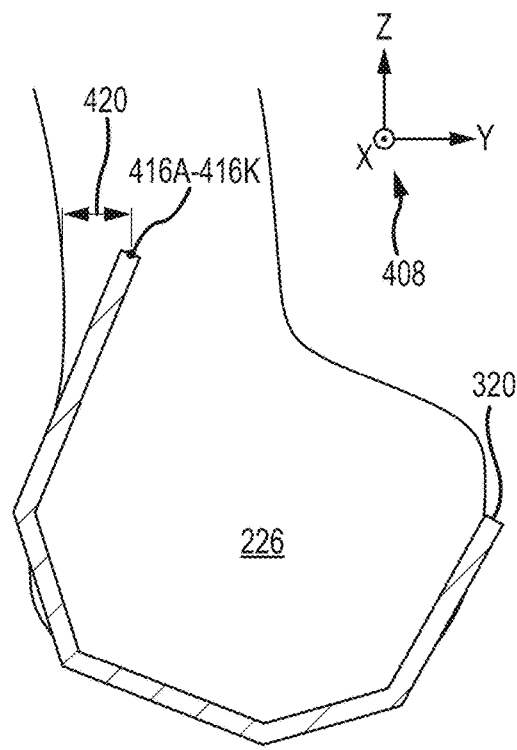
NO NOTCHING
NOTCHING
FIG.25A
FIG.25B

| Serial # | Femur Checkpoint | Error |
|---|---|---|
| 1 | Posterior Cut System Error | X1 |
| 2 | Distal Cut System Error | X2 |
| 3 | Anterior Chamfer Error due to Posterior Cut | X3 |
| 4 | Anterior Chamfer Error due to Distal Cut | X4 |
| 5 | Profile Error[2] | X5 |
| 6 | Root of Sum of Squares of (3), (4), (5) | X6 |
| 7 | Distance of Blade from TCP inside Checkpoint | X7 |
| | Total Threshold Distance (6) + (7) | X8 |

650

| Serial # | Tibia Checkpoint | Error |
|---|---|---|
| 1 | Proximal Cut Error | Y1 |
| 2 | Distance of Blade from TCP inside Checkpoint | Y2 |
| | Total Threshold Distance | Y3 |

PREOPERATIVE PLANNING AND ASSOCIATED INTRAOPERATIVE REGISTRATION FOR A SURGICAL SYSTEM

CROSS REFERENCE TO RELATED APPLICATIONS

The present application is a divisional application of U.S. application Ser. No. 15/167,771 filed May 27, 2016, which application is hereby incorporated by reference in its entirety.

TECHNICAL FIELD

The present disclosure relates to medical systems and methods. More specifically, the present disclosure relates to preoperative planning of surgeries and registering of associated information for use by a computerized surgical system.

BACKGROUND

Modern orthopedic joint replacement surgery typically involves at least some degree of preoperative planning of the surgery in order to increase the effectiveness and efficiency of the particular procedure. In particular, preoperative planning may increase the accuracy of bone resections and implant placement while reducing the overall time of the procedure and the time the patient joint is open and exposed.

The use of robotic systems in the performance of orthopedic joint replacement surgery can greatly reduce the intraoperative time of a particular procedure. Increasingly, the effectiveness of the procedure may be based on the tools, systems, and methods utilized during the preoperative planning stages.

Examples of steps involved in preoperative planning may involve determining: implant size, position, and orientation; resection planes and depths; access trajectories to the surgical site; and others. In certain instances, the preoperative plan may involve generating a three-dimensional ("3D"), patient specific, model of the patient bone(s) to undergo the joint replacement. The 3D patient model may be used as a visual aid in planning the various possibilities of implant sizes, implant orientations, implant positions, and corresponding resection planes and depths, among other parameters.

While the framework for certain aspects of preoperative planning may be known in the art, there is a need for tools, systems, and methods to further refine certain aspects of preoperative planning to further increase efficiency and effectiveness in robotic and robotic-assisted orthopedic joint replacement surgery.

SUMMARY

Aspects of the present disclosure may involve a method of generating resection plane data for use in planning an arthroplasty procedure on a patient bone. The method may include: obtaining patient data associated with at least a portion of the patient bone, the patient data captured using a medical imaging machine; generating a three-dimensional patient bone model from the patient data, the patient bone model including a polygonal surface mesh; identifying a location of a posterior point on the polygonal surface mesh; creating a three-dimensional shape centered at or near the location; identifying a most posterior vertex of all vertices of the polygonal surface mesh that may be enclosed by the three-dimensional shape; using the most posterior vertex as a factor for determining a posterior resection depth; and generating resection data using the posterior resection depth, the resection data configured to be utilized by a navigation system during the arthroplasty procedure.

In certain instances, the three-dimensional patient bone model may be a three-dimensional patient femur model.

In certain instances, the method may further include: identifying a first location of a first posterior point on a first three-dimensional bone model; and mapping the first location on the first three-dimensional bone model to the location on the three-dimensional patient bone model. The first location may be positionally correlated with the location.

In certain instances, the first three-dimensional bone model may be a generic bone model.

In certain instances, the three-dimensional shape may include a sphere with a radius of about 7 mm.

In certain instances, the radius may be multiplied by a scaling factor.

In certain instances, the scaling factor may be one of a medial-lateral or anterior-posterior size difference between the three-dimensional patient bone model and a generic bone model.

In certain instances, the polygonal surface mesh may be a triangular surface mesh.

In certain instances, the three-dimensional shape may include a sphere.

In certain instances, the navigation system operates in conjunction with an autonomous robot or a surgeon-assisted device in performing the arthroplasty procedure.

Aspects of the present disclosure may involve a method of generating resection plane data for use in planning an arthroplasty procedure on a patient bone. The method may include: obtaining patient data associated with at least a portion of the patient bone, the patient data captured using a medical imaging machine; generating a three-dimensional patient bone model from the patient data, the patient bone model including a polygonal surface mesh; identifying a location of a distal point on the polygonal surface mesh; creating a three-dimensional shape centered at or near the location; identifying a most distal vertex of all vertices of the polygonal surface mesh that are enclosed by the three-dimensional shape; and determining if the most distal vertex may be too close to a boundary of the three-dimensional shape; using the most distal vertex as a basis for determining a distal resection depth if the most distal vertex may be not too close to the boundary of the three-dimensional shape; and generating resection data using the distal resection depth, the resection data configured to be utilized by a navigation system during the arthroplasty procedure.

In certain instances, the three-dimensional shape may include an ellipsoid oriented relative to the three-dimensional patient bone model such that Rx extends medial-lateral, Ry extends anterior-posterior, and Rz extends distal-proximal. In certain instances, Rx may be about 7 mm, Ry may be about 10 mm, and Rz may be about 7 mm.

In certain instances, the most distal vertex may be too close to the boundary of the ellipsoid if a location of the most distal vertex may be greater than 0.65 for the ellipsoid function: $f = x^2/a^2 + y^2/b^2 + z^2/c^2$, x may be a difference in an x-direction between the first location and the most distal vertex, y may be a difference in a y-direction between the first location and the most distal vertex, z may be a difference in a z-direction between the first location and the most distal vertex, a may be Rx, b may be Ry, and c may be Rz.

In certain instances, the three-dimensional patient bone model may be a three-dimensional patient femur model.

In certain instances, the three-dimensional shape may include an ellipsoid, a sphere, a prism, a cube, or a cylinder.

In certain instances, the navigation system operates in conjunction with an autonomous robot or a surgeon-assisted device in performing the arthroplasty procedure.

Aspects of the present disclosure may involve a method of generating resection plane data for use in planning an arthroplasty procedure on a patient bone. The method may include: obtaining patient data associated with at least a portion of the patient bone, the patient data captured using a medical imaging machine; generating a three-dimensional patient bone model from the patient data, the patient bone model including a polygonal surface mesh; identifying a location of a distal point on the polygonal surface mesh; creating a first three-dimensional shape centered at or near the location; identifying a most distal vertex of all vertices of the polygonal surface mesh that are enclosed by the first three-dimensional shape; determining if the most distal vertex may be located on an osteophyte; using the most distal vertex or an adjusted location of the most distal vertex as a basis for determining a distal resection depth based on whether or not the most distal vertex may be located on the osteophyte; and generating resection data using the distal resection depth, the resection data configured to be utilized by a navigation system during the arthroplasty procedure.

In certain instances, determining if the most distal vertex may be located on an osteophyte may include creating a second three-dimensional shape positioned between the most distal vertex and the location.

In certain instances, the method may further include identifying particular vertices of the polygonal surface mesh that are enclosed by the second three-dimensional shape, and using information associated with the particular vertices to determine if the distal vertex may be located on an osteophyte.

In certain instances, the information may be a minimum and a maximum value in a direction associated with a presence of an osteophyte protruding from an articular surface.

In certain instances, the method may further include identifying particular vertices of the polygonal surface mesh that are enclosed by the second three-dimensional shape, and using a minimum vertex value of one of the particular vertices enclosed by the second three-dimensional shape in a certain coordinate direction and a maximum vertex value of another one of the particular vertices enclosed by the second three-dimensional shape in the certain coordinate direction to determine if the distal vertex may be located on an osteophyte.

In certain instances, the method may further include determining the difference between the maximum vertex value and the minimum vertex value, and using the difference to determine the presence of an osteophyte.

In certain instances, the second three-dimensional shape may include a sphere having a radius of about 2 mm and may be centered 1 mm towards the location from the most distal vertex.

In certain instances, the method may further include identifying particular vertices of the polygonal surface mesh that are enclosed by a boundary of the sphere, and determining a difference between a maximum vertex value of one of the particular vertices enclosed by the boundary in a certain coordinate direction and a minimum vertex value of another one of the particular vertices enclosed by the boundary in the certain coordinate direction.

In certain instances, the method may further include using the difference to determine whether to increase or decrease a size of the sphere.

In certain instances, the first three-dimensional shape may include an ellipsoid. In certain instances, the second three-dimensional shape may include a sphere.

In certain instances, the navigation system operates in conjunction with an autonomous robot or a surgeon-assisted device in performing the arthroplasty procedure.

Aspects of the present disclosure may involve a method of generating resection plane data for use in planning an arthroplasty procedure on a patient bone. The method may include: obtaining patient data associated with at least a portion of the patient bone; generating a three-dimensional patient bone model from the patient data, the patient bone model oriented in a three-dimensional coordinate system and including a polygonal surface mesh; identifying a particular direction in the three-dimensional coordinate system associated with a resection plane; identifying a location on the polygonal surface mesh; creating a surface at or near the location; identifying a particular vertex of all vertices of the polygonal surface mesh that extends furthest beyond the surface in the particular direction; using the particular vertex as a factor for determining a particular resection depth; and generating resection data using the particular resection depth, the particular resection data configured to be utilized by a navigation system during the arthroplasty procedure.

In certain instances, the surface may be a plane.

In certain instances, the surface may be a three-dimensional shape. In certain instances, the three-dimensional shape may be a sphere, ellipsoid, prism, or cube.

In certain instances, the method may further include identifying a first location of a first posterior point on a first three-dimensional bone model; and mapping the first location on the first three-dimensional bone model to the location on the three-dimensional patient bone model. The first location may be positionally correlated with the location.

In certain instances, the first three-dimensional bone model may be a generic bone model.

In certain instances, the surface may include a sphere with a radius of about 7 mm. In certain instances, the radius may be multiplied by a scaling factor. In certain instances, the scaling factor may be one of a medial-lateral or anterior-posterior size difference between the three-dimensional patient bone model and a generic bone model.

In certain instances, the navigation system operates in conjunction with an autonomous robot or a surgeon-assisted device in performing the arthroplasty procedure.

Aspects of the present disclosure may involve a method of generating resection plane and checkpoint positioning data for use in planning an arthroplasty procedure on a patient bone. The method may include: obtaining patient data associated with at least a portion of the patient bone, the patient data captured using a medical imaging machine; generating a three-dimensional patient bone model from the patient data, the patient bone model including a polygonal surface mesh; identifying a first location of a first checkpoint on the patient bone model; identifying a second location of a resection plane relative to the patient bone model, the resection plane defining a resection surface on the patient bone model to be exposed following a resection; determining a shortest signed distance vector from the first location to a point on the resection surface; using information associated with the shortest signed distance vector to determine if the first location of the first checkpoint may be located too close to the second location of the resection plane; and generating resection and checkpoint positioning data using the information, the resection and checkpoint positioning data configured to be utilized by a navigation system during the arthroplasty procedure.

In certain instances, the method may further include identifying a normal line for the resection surface, the normal line extending away from the patient bone model and perpendicular to the resection surface.

In certain instances, the method may further include determining the first location of the first checkpoint may be located too close to the second location of the resection plane when the normal line and the shortest signed distance vector point in opposite directions.

In certain instances, the patient bone model may be a femur bone model. In certain instances, the patient bone model may be a tibial bone model.

In certain instances, the method may further include determining the checkpoint may be located too close to the resection plane when: the normal line and the shortest signed distance vector point in a same direction, and a magnitude of the shortest signed distance vector may be less than or equal to about 4.50 mm.

In certain instances, the patient bone model may be a femur bone model. In certain instances, the patient bone model may be a tibial bone model.

In certain instances, the navigation system operates in conjunction with an autonomous robot or a surgeon-assisted device in performing the arthroplasty procedure.

Aspects of the present disclosure may involve a method of generating implant position and orientation data for use in planning an arthroplasty procedure on a patient bone including a lateral femur area, proximal femur area, and a posterior femur area. The method may include: obtaining patient data associated with at least a portion of the patient bone; generating a three-dimensional patient femur model from the patient data, the patient femur model including a surface boundary and a cortex region, the patient femur model being in a three-dimensional coordinate system with an X-axis in a medial-lateral direction, a Y-axis in an anterior-posterior direction with the +Y-axis pointing towards the posterior femur area, and a Z-axis in a superior-inferior direction with the +Z axis pointing towards the proximal femur area; obtaining a three-dimensional femoral implant model including an anterior flange portion having a superior edge and an anterior bone resection contact surface being planar and adjacent the superior edge; determining a position and orientation of the femoral implant model relative to the patient femur model; extending a haptic plane coplanar with the anterior bone resection contact surface, the haptic plane including a superior boundary positioned superior of the superior edge of the anterior flange portion of the femoral implant model; identifying a series of points on the superior boundary of the haptic plane; projecting a vector along the Y-axis from each of the series of points to a corresponding surface of the surface boundary of the patient femur model; determining that notching occurs based on a length and a direction of a smallest of the vectors; and generating implant component position and orientation data based on the determined position and orientation of the femoral implant model relative to the patient femur model, the implant component position and orientation data configured to be utilized by a navigation system during the arthroplasty procedure.

In certain instances, notching occurs when: the length of the smallest of the vectors may be equal to or greater than 0 mm; and the direction of the smallest of the vectors may be opposite of the +Y-axis of the coordinate system.

In certain instances, no notching occurs when: the length of the smallest of the vectors may be greater than 0 mm; and the direction of the smallest of the vectors may be in a same direction as the +Y-axis of the coordinate system.

In certain instances, the length may be based on a perceivable depth of notching.

In certain instances, the series of points are equally spaced along the superior boundary of the haptic plane. In certain instances, the series of points are equally spaced based upon a radius of curvature at or near the cortex region of the patient femur model. In certain instances, the series of points are equally spaced based upon a clinically relevant depth of perceivable notching. In certain instances, the series of points are equally spaced based upon: a radius of curvature at or near the cortex region of the patient femur model; and a clinically relevant depth of perceivable notching. In certain instances, the series of points are equally spaced about 3.15 mm apart.

In certain instances, the patient data may be captured using a medical imaging machine.

In certain instances, the navigation system operates in conjunction with an autonomous robot or a surgeon-assisted device in performing the arthroplasty procedure.

Aspects of the present disclosure may involve a method of generating implant position and orientation data for use in planning an arthroplasty procedure on a patient bone including a lateral femur area, proximal femur area, and a posterior femur area. The method may include: obtaining patient data associated with at least a portion of the patient bone, the patient data captured using a medical imaging machine; generating a three-dimensional patient femur model from the patient data; obtaining a three-dimensional femoral implant model including an anterior flange portion having an associated haptic resection object having a superior boundary edge; determining a position and orientation of the femoral implant model relative to the patient femur model; determining that notching occurs based on an intersection of the superior boundary edge and the three-dimensional patient femur model; and generating implant component position and orientation data based on the determined position and orientation of the femoral implant model relative to the patient femur model, the implant component position and orientation data configured to be utilized by a navigation system during the arthroplasty procedure.

In certain instances, the three-dimensional patient femur model may include a surface boundary and a cortex region, the patient femur model being in a three-dimensional coordinate system with an X-axis in a medial-lateral direction, a Y-axis in an anterior-posterior direction with the +Y-axis pointing towards the posterior femur area, and a Z-axis in a superior-inferior direction with the +Z axis pointing towards the proximal femur area; the method further including: identifying a series of points on the superior boundary edge of the haptic resection object; projecting a vector along the Y-axis from each of the series of points to a corresponding surface of the surface boundary of the patient femur model; and determining that notching occurs based on a length and a direction of a smallest of the vectors.

In certain instances, notching occurs when: the length of the smallest of the vectors may be equal to or greater than 0 mm; and the direction of the smallest of the vectors may be opposite of the +Y-axis of the coordinate system.

In certain instances, no notching occurs when: the length of the smallest of the vectors may be greater than 0 mm; and the direction of the smallest of the vectors may be in a same direction as the +Y-axis of the coordinate system.

In certain instances, the length may be based on a perceivable depth of notching.

In certain instances, the series of points are equally spaced along the superior boundary edge. In certain instances, the series of points are equally spaced based upon a radius of curvature at or near the cortex region of the patient femur model. In certain instances, the series of points are equally spaced based upon a clinically relevant depth of perceivable notching. In certain instances, the series of points are equally spaced based upon: a radius of curvature at or near the cortex region of the patient femur model; and a clinically relevant depth of perceivable notching. In certain instances, the series of points are equally spaced about 3.15 mm apart.

In certain instances, the navigation system operates in conjunction with an autonomous robot or a surgeon-assisted device in performing the arthroplasty procedure.

Aspects of the present disclosure may involve a method of generating resection data for use in planning an arthroplasty procedure on a patient bone covered at least partially in cartilage. The method may include: receiving a three-dimensional patient bone model including a bone model surface, the three-dimensional patient bone model correlated with a position and orientation of the patient bone via a navigation system, the three-dimensional patient bone model in a three-dimensional coordinate system; identifying a target region on the bone model surface of the three-dimensional patient bone model for intra-operative registration; receiving location data for a first plurality of points based on the intra-operative registration of the cartilage on the patient bone in locations corresponding to points within the target region on the bone model surface of the three-dimensional bone model; determining a resection depth based at least in part on the location data for the first plurality of point; and generating resection data using the resection depth, the resection data configured to be utilized by the navigation system during the arthroplasty procedure.

In certain instances, the method may further include mapping the location data for the first plurality of points into the three-dimensional coordinate system.

In certain instances, determining the resection depth may include determining a depth difference between the first plurality of points and the target region on the bone model surface.

In certain instances, the method may further include determining the resection depth by adding the depth difference to a bone-only resection depth.

In certain instances, the bone-only resection depth may be adjusted distally by the addition of the depth difference.

In certain instances, determining the resection depth may include altering a bone-only resection depth based on the first plurality of points.

In certain instances, the bone-only resection depth may be adjusted distally based on the first plurality of points.

In certain instances, the patient bone may include a femur and the three-dimensional patient bone model may include a three-dimensional patient femur model.

In certain instances, the target region may include an articular area of at least one of a medial or lateral condyle of the three-dimensional patient femur model.

In certain instances, the patient bone may include a tibia and the three-dimensional patient bone model may include a three-dimensional patient tibia model.

In certain instances, the resection depth may include a proximal resection depth of the tibia, the proximal resection depth may be adjusted proximally based on the location data for the first plurality of points.

In certain instances, the target region may include an articular area of at least one of a medial or lateral tibial plateau of the three-dimensional patient tibia model.

In certain instances, the three-dimensional patient bone model may be a bone only model.

In certain instances, the three-dimensional patient bone model may be generated from medical images of the patient bone.

In certain instances, the navigation system operates in conjunction with an autonomous robot or a surgeon-assisted device in performing the arthroplasty procedure.

Aspects of the present disclosure may involve a method of generating resection data for use in planning an arthroplasty procedure on a knee joint including a femur and a tibia of a patient. The method may include: receiving a three-dimensional femur model and a three-dimensional femur implant model oriented relative to each other in a first pre-planned orientation in a common three-dimensional coordinate system, the three-dimensional femur model corresponding to the femur of the patient, the three-dimensional femur implant model including a medial condyle surface and a lateral condyle surface; receiving a three-dimensional tibia model and a three-dimensional tibia implant model oriented relative to each other in a second pre-planned orientation in the common three-dimensional coordinate system, the three-dimensional tibia model corresponding to the tibia of the patient, the three-dimensional tibia implant model including a medial articular surface and a lateral articular surface, the three-dimensional femur model and the three-dimensional tibia model oriented relative to each other according to a pose of the femur and tibia of the patient via a navigation system; receiving first position and orientation data corresponding to a first position and orientation of the femur and the tibia in a first pose; calculating a first signed distance between the medial condyle surface of the three-dimensional femur implant model and a first point on or associated with the three-dimensional tibia implant model in the first pose; calculating a second signed distance between the lateral condyle surface of the three-dimensional femur implant model and a second point on or associated with the three-dimensional tibia implant model in the first pose; determining or adjusting a resection depth based on the first and second signed distances; and generating resection data using the resection depth, the resection data configured to be utilized by the navigation system during the arthroplasty procedure.

In certain instances, the three-dimensional femur model and the three-dimensional tibia model are generated from medical images of the knee joint of the patient.

In certain instances, the first pose may be with the knee joint in extension.

In certain instances, the first point may be on the medial articular surface of the three-dimensional tibia implant model, and the second point may be on the lateral articular surface of the three-dimensional tibia implant model.

In certain instances, the first and second signed distances are calculated via a global search closest distance algorithm.

In certain instances, the global search closest distance algorithm identifies a reference vertex associated with each of the medial and lateral condyle surfaces and the medial and lateral articular surfaces.

In certain instances, the method may further include: receiving second position and orientation data corresponding to a second position and orientation of the femur and the tibia in a second pose that may be different than the first pose; calculating a third signed distance between the medial condyle surface of the three-dimensional femur implant model and the medial articular surface of the three-dimensional tibia implant model in the second pose; and calculating a fourth signed distance between the lateral condyle surface of the three-dimensional femur implant model and the lateral articular surface of the three-dimensional tibia implant model in the second pose.

In certain instances, the second pose may be flexion.

In certain instances, the first, second, third, and fourth signed distances are calculated via a global search closest distance algorithm.

In certain instances, the first and second signed distances are calculated via a global search closest distance algorithm, and the third and fourth signed distances are calculated via an incremental search closest distance algorithm.

In certain instances, the global search closest distance algorithm identifies a reference vertex associated with each of the medial and lateral condyle surfaces and the medial and lateral articular surfaces, and the incremental search closest distance algorithm may be utilized for particular vertexes that are adjacent the reference vertexes of the medial and lateral condyle surfaces to determine if any of the particular vertexes are closer to the corresponding medial or lateral articular surface, respectively, than the reference vertexes.

In certain instances, the three-dimensional femur implant model may include a first triangular surface mesh including vertexes, the three-dimensional tibia implant model including a second triangular surface mesh including faces, the first and second signed distances are calculated between the vertexes of the three-dimensional femur implant model and the faces of the three-dimensional tibia implant model.

In certain instances, the medial and lateral articular surfaces of the three-dimensional tibia implant model are modified to be flatter or less concave for determining the resection depth as compared with medial and articular surfaces of a physical tibial implant to be employed in the arthroplasty procedure.

In certain instances, the first point may be on a medial portion of a tibial resection plane associated with the three-dimensional tibia implant model, and the second point may be on a lateral portion of the tibial resection plane associated with the three-dimensional tibia implant model.

In certain instances, the navigation system operates in conjunction with an autonomous robot or a surgeon-assisted device in performing the arthroplasty procedure.

Aspects of the present disclosure may involve a method of generating resection data for use in planning an arthroplasty procedure on a joint formed by a first bone and a second bone of the patient. The method may include: receiving a first three-dimensional bone model and a first three-dimensional implant model oriented relative to each other in a first pre-planned orientation in a common three-dimensional coordinate system, the first three-dimensional bone model corresponding to the first bone of the patient, the first three-dimensional implant model including a first implant articular surface; receiving a second three-dimensional bone model and a second three-dimensional implant model oriented relative to each other in a second pre-planned orientation in the common three-dimensional coordinate system, the second three-dimensional bone model corresponding to the second bone of the patient, the second three-dimensional implant model including a second implant articular surface, the first three-dimensional bone model and the second three-dimensional bone model oriented relative to each other according to a pose of the first bone and the second bone of the patient via a navigation system; receiving first position and orientation data corresponding to a first position and orientation of the first bone and the second bone in a first pose; calculating a first signed distance between the first implant articular surface of the first three-dimensional implant model and a first point on or associated with the second three-dimensional implant model in the first pose; determining or adjusting a resection depth based on the first distance; and generating resection data using the resection depth, the resection data configured to be utilized by the navigation system during the arthroplasty procedure.

In certain instances, the joint may be one of a knee, ankle, elbow, or wrist.

In certain instances, the first bone may be a femur and the second bone may be a tibia.

In certain instances, the first point may be on a portion of a proximal tibial resection plane associated with the second three-dimensional implant model.

In certain instances, the first three-dimensional implant model may include a medial condyle surface and a lateral condyle surface, the second three-dimensional implant model may include a medial articular surface and a lateral articular surface, the first signed distance determined between the medial condyle surface and the first point.

In certain instances, the method may further include calculating a second signed distance between the lateral condyle surface and a second point on or associated with the second three-dimensional implant model in the first pose.

In certain instances, the first point may be on the medial articular surface of the second three-dimensional implant model, and the second point may be on the lateral articular surface of the second three-dimensional implant model.

In certain instances, the medial and lateral articular surfaces of the second three-dimensional implant model are modified to be flatter or less concave for determining the resection depth as compared with medial and articular surfaces of a physical implant to be employed in the arthroplasty procedure.

In certain instances, the first and second signed distances are calculated via a global search closest distance algorithm.

In certain instances, the global search closest distance algorithm identifies a reference vertex associated with each of the medial and lateral condyle surfaces and the medial and lateral articular surfaces.

In certain instances, the method may further include: receiving second position and orientation data corresponding to a second position and orientation of the first bone and the second bone in a second pose that may be different than the first pose; calculating a third signed distance between the medial condyle surface of the first three-dimensional implant model and the medial articular surface of the second three-dimensional implant model in the second pose; and calculating a fourth signed distance between the lateral condyle surface of the first three-dimensional implant model and the lateral articular surface of the second three-dimensional implant model in the second pose.

In certain instances, the first, second, third, and fourth signed distances are calculated via a global search closest distance algorithm.

In certain instances, the first and second signed distances are calculated via a global search closest distance algorithm, and the third and fourth signed distances are calculated via an incremental search closest distance algorithm.

In certain instances, the global search closest distance algorithm identifies a reference vertex associated with each of the medial and lateral condyle surfaces and the medial and lateral articular surfaces, and the incremental search closest distance algorithm may be utilized for particular vertexes that are adjacent the reference vertexes of the medial and lateral condyle surfaces to determine if any of the particular vertexes are closer to the corresponding medial or lateral articular surface, respectively, than the reference vertexes.

In certain instances, the navigation system operates in conjunction with an autonomous robot or a surgeon-assisted device in performing the arthroplasty procedure.

While multiple embodiments are disclosed, still other embodiments of the present disclosure will become apparent to those skilled in the art from the following detailed description, which shows and describes illustrative embodiments of the disclosure. As will be realized, the embodiments discussed herein are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 1 is an illustration of a surgical system.

FIGS. 4A and 4B respectively illustrate three dimensional computer models of a proximal end of a generic tibia and a distal end of a generic femur wherein each three dimensional model is represents a statistical average of its respective bone type according to both size and shape.

FIGS. 5A-5C respectively illustrate coronal, axial or transverse, and sagittal views of the proximal end of the three dimensional computer model of the patient tibia (i.e., the patient tibia model).

FIGS. 6A-6C respectively illustrate coronal, axial or transverse, and sagittal views of the distal end of the three dimensional computer model of the patient femur (i.e., patient femur model).

FIGS. 25A and 25B are cross-sectional sagittal views of the patient femur model and the candidate femoral implant model thereon in no-notching and notching arrangements, respectively.

FIG. 26H is a table illustrating errors associated with the various resections.

DETAILED DESCRIPTION

Figure 2:
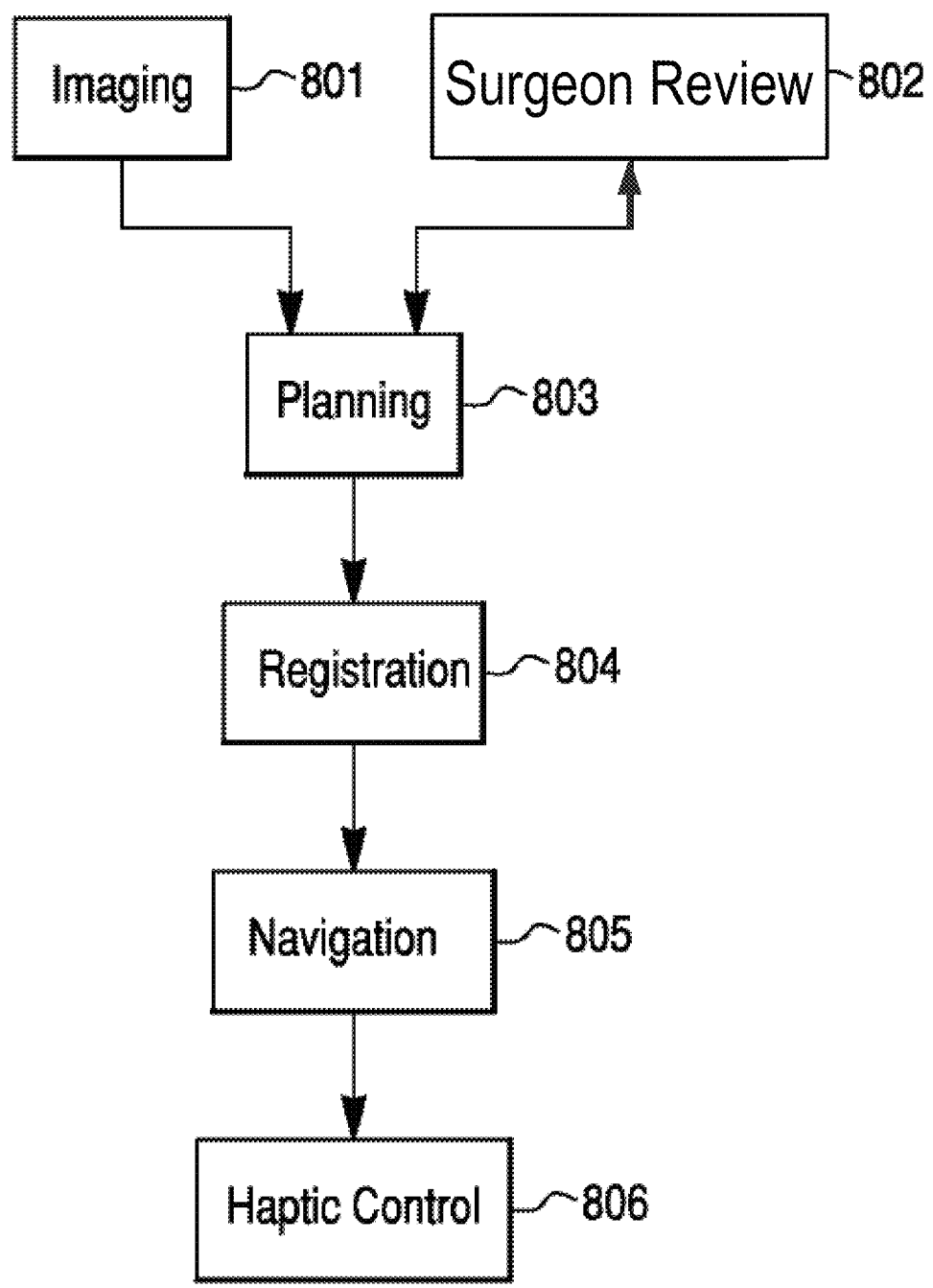
FIG. 2 is a flow chart illustrating surgical planning and performance of an arthroplasty.

Preoperative planning of arthroplasty surgical procedures for execution via a surgical system 100 is disclosed herein. The preoperative planning includes defining bone resection depths and identifying whether or not unacceptable notching of the femoral anterior cortex is associated with the proposed bone resection depths and proposed pose of the candidate implants. Assuming the preoperatively planned bone resection depths and implant poses are free of unacceptable notching of the femoral anterior cortex and approved by the surgeon, the bone resection depths can be updated to account for cartilage thickness by intraoperatively registering the cartilage condylar surfaces of the actual patient bones to the patient bone models employed in the preoperative planning. By so accounting for the cartilage thickness, the actual implants, upon implantation via the surgical system 100, will have their respective condylar surfaces located so as to act in place of the resected cartilage condylar surfaces of the actual patient bones.

Before beginning a detailed discussion of the preoperative planning and the intraoperative registering of the cartilage condylar surface, an overview of the surgical system and its operation will now be given as follows.

I. Overview of Surgical System

To begin a detailed discussion of the surgical system, reference is made to FIG. 1. As can be understood from FIG. 1, the surgical system 100 includes a navigation system 42, a computer 50, and a haptic device 60. The navigation system tracks the patient's bone (i.e., tibia 10, femur 11), as well as surgical tools (e.g., pointer device, probe, cutting tool) utilized during the surgery, to allow the surgeon to visualize the bone and tools on a display 56 during the osteotomy procedure.

The navigation system 42 may be any type of navigation system configured to track the pose (i.e. position and orientation) of a bone. For example, the navigation system 42 may include a non-mechanical tracking system, a mechanical tracking system, or any combination of non-mechanical and mechanical tracking systems. The navigation system 42 includes a detection device 44 that obtains a pose of an object with respect to a coordinate frame of reference of the detection device 44. As the object moves in the coordinate frame of reference, the detection device tracks the pose of the object to detect movement of the object.

In one embodiment, the navigation system 42 includes a non-mechanical tracking system as shown in FIG. 1. The non-mechanical tracking system is an optical tracking system with a detection device 44 and a trackable element (e.g. navigation marker 46) that is disposed on a tracked object and is detectable by the detection device 44. In one embodiment, the detection device 44 includes a visible light-based detector, such as a MicronTracker (Claron Technology Inc., Toronto, Canada), that detects a pattern (e.g., a checkerboard pattern) on a trackable element. In another embodiment, the detection device 44 includes a stereo camera pair sensitive to infrared radiation and positionable in an operating room where the arthroplasty procedure will be performed. The trackable element is affixed to the tracked object in a secure and stable manner and includes an array of markers having a known geometric relationship to the tracked object. As is known, the trackable elements may be active (e.g., light emitting diodes or LEDs) or passive (e.g., reflective spheres, a checkerboard pattern, etc.) and have a unique geometry (e.g., a unique geometric arrangement of the markers) or, in the case of active, wired or wireless markers, a unique firing pattern. In operation, the detection device 44 detects positions of the trackable elements, and the surgical system 100 (e.g., the detection device 44 using embedded electronics) calculates a pose of the tracked object based on the trackable elements' positions, unique geometry, and known geometric relationship to the tracked object. The tracking system 42 includes a trackable element for each object the user desires to track, such as the navigation marker 46 located on the bone 10. During haptically guided robotic-assisted surgeries, the navigation system may further include a haptic device marker 48 (to track a global or gross position of the haptic device 60), an end effector marker 54 (to track a distal end of the haptic device 60), and a free-hand navigation probe 55 for use in the registration process.

As indicated in FIG. 1, the surgical system 100 further includes a processing circuit, represented in the figures as a computer 50. The processing circuit includes a processor and memory device. The processor can be implemented as a general purpose processor, an application specific integrated circuit (ASIC), one or more field programmable gate arrays (FPGAs), a group of processing components, a purpose-specific processor, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes, layers and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit and includes computer code for executing (e.g., by the processing circuit and/or processor) one or more processes described herein.

The computer 50 is configured to communicate with the navigation system 42 and the haptic device 60. Furthermore, the computer 50 may receive information related to osteotomy procedures and perform various functions related to performance of osteotomy procedures. For example, the computer 50 may have software as necessary to perform functions related to image analysis, surgical planning, registration, navigation, image guidance, and haptic guidance. More particularly, the navigation system may operate in conjunction with an autonomous robot or a surgeon-assisted device (haptic device) in performing the arthroplasty procedure.

The computer 50 receives images of the patient's anatomy on which an arthroplasty procedure is to be performed. Referring to FIG. 2, prior to performance of an arthroplasty, the patient's anatomy is scanned using any known imaging technique, such as CT or MRI (Step 801) captured with a medical imaging machine. And while the disclosure makes reference to medical images captured or generated with a medical imaging machine such as a CT or MRI machine, other methods of generating the medical images are possible and contemplated herein. For example, an image of the bone may be generated intra-operatively via a medical imaging machine such as a hand-held scanning or imaging device that scans or registers the topography of the bone surface. Thus, the term medical imaging machine is intended to encompass relatively large devices located at imaging centers as well as hand-held imaging devices used intra-operatively.

Continuing on, the scan data is then segmented to obtain a three-dimensional representation of the patient's anatomy. For example, prior to performance of a knee arthroplasty, a three-dimensional representation of the femur and tibia is created. Using the three-dimensional representation and as part of the planning process, femoral and tibial landmarks can be selected, and the patient's femoral-tibial alignment is calculated along with the orientation and placement of the proposed femoral and tibial implants, which may be selected as to model and size via the computer 50. The femoral and tibial landmarks may include the femoral head center, the distal trochlear groove, the center of intercondylar eminence, the tibia-ankle center, and the medial tibial spine, among others. The femoral-tibial alignment is the angle between the femur mechanical axis (i.e., line from femoral head center to distal trochlear groove) and the tibial mechanical axis (i.e., line from ankle center to intercondylar eminence center). Based on the patient's current femoral-tibial alignment and the desired femoral-tibial alignment to be achieved by the arthroplasty procedure and further including the size, model and placement of the proposed femoral and tibial implants, including the desired extension, varus-valgus angle, and internal-external rotation associated with the implantation of the proposed implants, the computer 50 is programmed to calculate the desired implantation of the proposed implants or at least assist in the preoperative planning of the implantation of the proposed implants, including the resections to be made via the haptic device 60 in the process of performing the arthroplasty procedure (Step 803). The preoperative plan achieved via Step 803 is provided to the surgeon for review, adjustment and approval, and the preoperative plan is updated as directed by the surgeon (Step 802).

Since the computer 50 is used to develop a surgical plan according to Step 803, it should be understood that a user can interact with the computer 50 at any stage during surgical planning to input information and modify any portion of the surgical plan. The surgical plan includes a plurality of planned virtual boundaries. The virtual boundaries can represent holes and/or cuts to be made in a bone 10, 11 during an arthroplasty procedure. Once the surgical plan has been developed, a haptic device 60 is used to assist a user in creating the planned holes and cuts in the bones 10, 11. Preoperative planning, especially with respect to bone resection depth planning and the prevention of femoral anterior shaft notching, will be explained more fully below.

The drilling of holes and creation of cuts or resections in bones 10, 11 can be accomplished with the assistance of a haptically guided interactive robotic system, such as the haptic guidance system described in U.S. Pat. No. 8,010,180, titled "Haptic Guidance System and Method," granted Aug. 30, 2011, and hereby incorporated by reference herein in its entirety. As the surgeon manipulates a robotic arm to drill holes in the bone or perform cuts with a high speed drill, sagittal saw, or other suitable tool, the system provides haptic feedback to guide the surgeon in sculpting the holes and cuts into the appropriate shape, which is pre-programmed into the control system of the robotic arm. Haptic guidance and feedback will be explained more fully below.

During surgical planning, the computer 50 further receives information related to femoral and tibial implants to be implanted during the arthroplasty procedure. For example, a user may input parameters of selected femoral and tibial implants into the computer 50 using the input device 52 (e.g. keyboard, mouse, etc.). Alternatively, the computer 50 may contain a pre-established database of various implants and their parameters, and a user can choose the selected implants from the database. In a still further embodiment, the implants may be custom designed based on a patient-specific surgical plan. Selection of the implants may occur during any stage of surgical planning The surgical plan may further be based on at least one parameter of the implants or a function of a parameter of the implants. Because the implants can be selected at any stage of the surgical planning process, the implants may be selected prior to or after determination of the planned virtual boundaries by the computer 50. If the implants are selected first, the planned virtual boundaries may be based at least in part on a parameter of the implants. For example, the distance (or any other relationship) between the planned virtual boundaries representing holes or cuts to made in the bones 10, 11 may be planned based on the desired varus-valgus femoral-tibial alignment, extension, internal-external rotation, or any other factors associated with a desired surgical outcome of the implantation of the arthroplasty implants. In this manner, implementation of the surgical plan will result in proper alignment of the resected bone surfaces and holes to allow the selected implants to achieve the desired surgical outcome. Alternatively, the computer 50 may develop the surgical plan, including the planned virtual boundaries, prior to implant selection. In this case, the implant may be selected (e.g. input, chosen, or designed) based at least in part on the planned virtual boundaries. For example, the implants can be selected based on the planned virtual boundaries such that execution of the surgical plan will result in proper alignment of the resected bone surfaces and holes to allow the selected implants to achieve the desired surgical outcome.

The virtual boundaries exist in virtual space and can be representative of features existing or to be created in physical (i.e. real) space. Virtual boundaries correspond to working boundaries in physical space that are capable of interacting with objects in physical space. For example, working boundaries can interact with a surgical tool 58 coupled to haptic device 60. Although the surgical plan is often described herein to include virtual boundaries representing holes and resections, the surgical plan may include virtual boundaries representing other modifications to a bone 10, 11. Furthermore, virtual boundaries may correspond to any working boundary in physical space capable of interacting with objects in physical space.

Referring again to FIG. 2, after surgical planning and prior to performing an arthroplasty procedure, the physical anatomy (e.g. bones 10, 11) is registered to a virtual representation of the anatomy (e.g. a preoperative three-dimensional representation) using any known registration technique (Step 804). Possible registration techniques include the point-based registration technique described in above-referenced U.S. Pat. No. 8,010,180, or 2D/3D registration utilizing a hand-held radiographic imaging device as described in U.S. application Ser. No. 13/562,163, titled "Radiographic Imaging Device," filed Jul. 30, 2012, and hereby incorporated by reference herein in its entirety. Registration of the patient's anatomy allows for accurate navigation during the surgical procedure (Step 805), which enables each of the virtual boundaries to correspond to a working boundary in physical space. For example, referring to FIGS. 3A and 3B, a virtual boundary 62 representing a resection in a tibia bone 10 is displayed on a computer or other display 63 and the virtual boundary 62 corresponds to a working boundary 66 in physical space 69, such as a surgery site in a surgical operating room. A portion of working boundary 66 in turn corresponds to the planned location of the resection in the tibia 10.

Figure 3B:
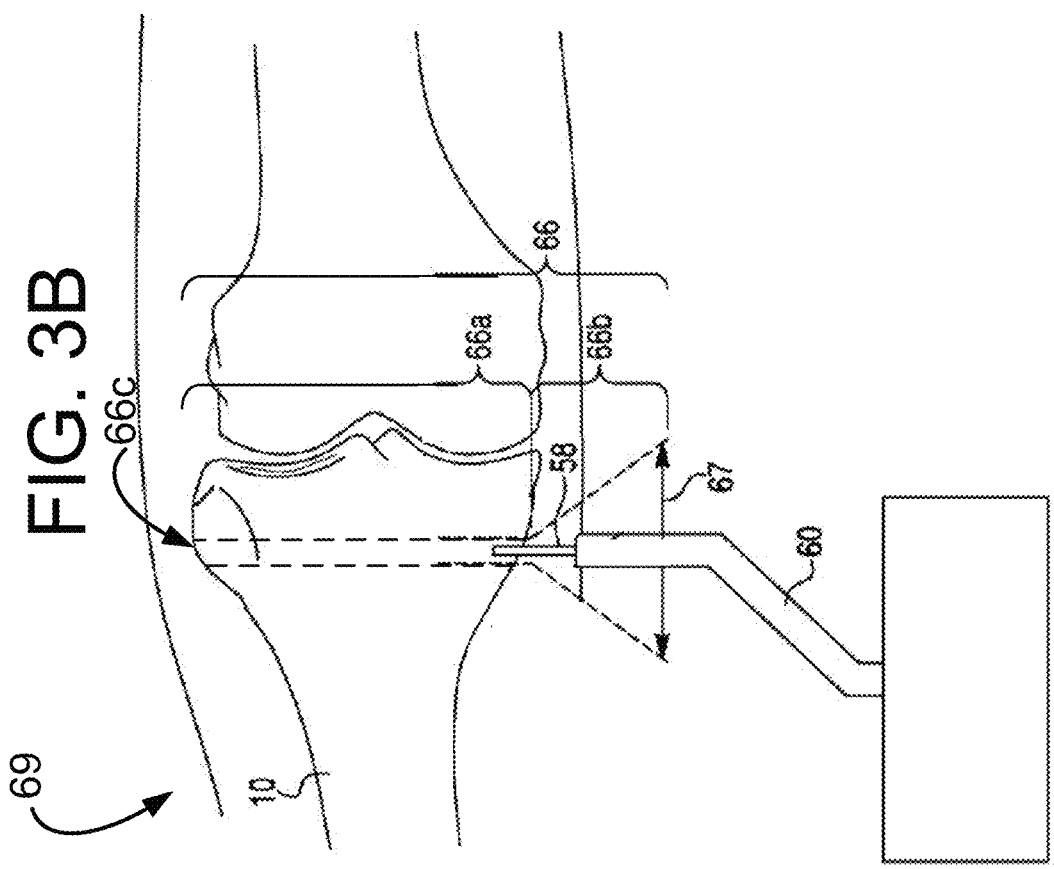
FIGS. 3A and 3B illustrate haptic guidance during performance of an arthroplasty.
Figure 3A:
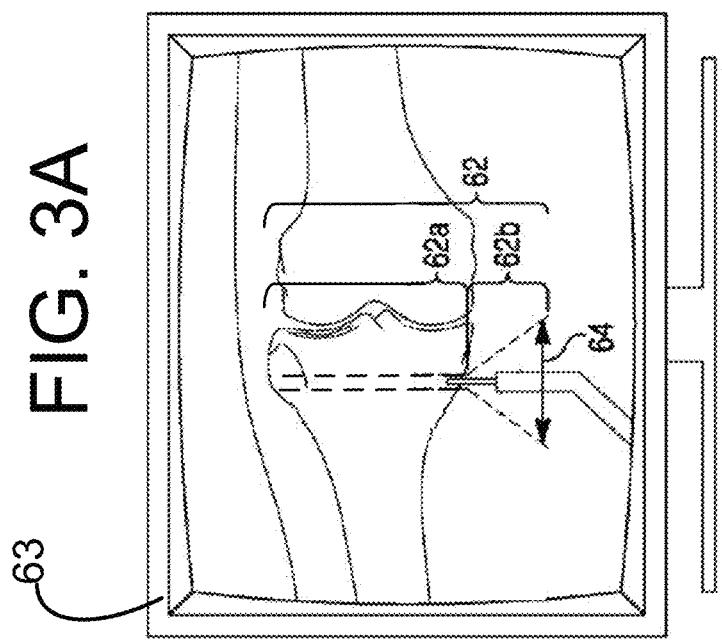

The virtual boundaries and, therefore, the corresponding working boundaries, can be any configuration or shape. Referring to FIG. 3A, virtual boundary 62 representing a proximal resection to be created in the tibia bone 10, may be any configuration suitable for assisting a user during creation of the proximal resection in the tibia 10. Portions of virtual boundary 62, illustrated within the virtual representation of the tibia bone 10, represent bone to be removed by a surgical tool Similar virtual boundaries may be generated for holes to be drilled or milled into the tibia bone 10 for facilitating the implantation of a tibial implant on the resected tibia 10. The virtual boundaries (and therefore, the corresponding working boundaries) may include a surface or surfaces that fully enclose and surround a three-dimensional volume. In an alternative embodiment, the virtual and working boundaries do not fully enclose a three-dimensional volume, but rather include both "active" surfaces and "open" portions. For example, virtual boundary 62 representing a proximal resection in a tibia bone may have an essentially rectangular box-shaped "active" surface 62a and a collapsing funnel or triangular box-shaped "active" surface 62b connected to the rectangular box-shaped portion, with an "open" portion 64. In one embodiment, virtual boundary 62 can be created with a collapsing funnel as described in U.S. application Ser. No. 13/340,668, titled "Systems and Methods for Selectively Activating Haptic Guide Zones," filed Dec. 29, 2011, and hereby incorporated by reference herein in its entirety. The working boundary 66 corresponding to virtual boundary 62 has the same configuration as virtual boundary 62. In other words, working boundary 66 guiding a proximal resection in a tibia bone 10 may have an essentially rectangular box-shaped "active" surface 66a and a collapsing funnel or triangular box-shaped "active" surface 66b connected to the rectangular box-shaped portion, with an "open" portion 67.

In an additional embodiment, the virtual boundary 62 representing the resection in the bone 10 includes only the substantially rectangular box-shaped portion 62 a. An end of a virtual boundary having only a rectangular box-shaped portion may have an "open" top such that the open top of the corresponding working boundary coincides with the outer surface of the bone 10. Alternatively, as shown in FIGS. 3A and 3B, the rectangular box-shaped working boundary portion 66 a corresponding to virtual boundary portion 62 a may extend past the outer surface of the bone 10.

In some embodiments, the virtual boundary 62 representing a resection through a portion of the bone may have an essentially planar shape, with our without a thickness. Alternatively, virtual boundary 62 can be curved or have an irregular shape. Where the virtual boundary 62 is depicted as a line or planar shape and the virtual boundary 62 also has a thickness, the virtual boundary 62 may be slightly thicker than a surgical tool used to create the resection in the bone, such that the tool can be constrained within the active surfaces of working boundary 66 while within the bone. Such a linear or planar virtual boundary 62 may be planned such that the corresponding working boundary 66 extends past the outer surface of the bone 10 in a funnel or other appropriate shape to assist a surgeon as the surgical tool 58 is approaching the bone 10. Haptic guidance and feedback (as described below) can be provided to a user based on relationships between surgical tool 58 and the active surfaces of working boundaries.

The surgical plan may also include virtual boundaries to facilitate entry into and exit from haptic control, including automatic alignment of the surgical tool, as described in U.S. application Ser. No. 13/725,348, titled "Systems and Methods for Haptic Control of a Surgical Tool," filed Dec. 21, 2012, and hereby incorporated by reference herein in its entirety.

The surgical plan, including the virtual boundaries, may be developed based on information related to the patient's bone density. The density of a patient's bone is calculated using data obtained from the CT, MRI, or other imaging of the patient's anatomy. In one embodiment, a calibration object representative of human bone and having a known calcium content is imaged to obtain a correspondence between image intensity values and bone density measurements. This correspondence can then be applied to convert intensity values of individual images of the patient's anatomy into bone density measurements. The individual images of the patient's anatomy, with the corresponding map of bone density measurements, are then segmented and used to create a three-dimensional representation (i.e. model) of the patient's anatomy, including the patient's bone density information. Image analysis, such as finite element analysis (FEA), may then be performed on the model to evaluate its structural integrity.

The ability to evaluate the structural integrity of the patient's anatomy improves the effectiveness of arthroplasty planning. For example, if certain portions of the patient's bone appear less dense (i.e. osteoporotic), the holes, resections and implant placement can be planned to minimize the risk of fracture of the weakened portions of bone. Furthermore, the planned structure of the bone and implant combination after implementation of the surgical plan (e.g. the post-operative bone and implant arrangement) can also be evaluated for structural integrity, preoperatively, to improve surgical planning. In this embodiment, holes and/or cuts are planned and the bone model and implant model are manipulated to represent the patient's bone and implant arrangement after performance of the arthroplasty and implantation procedures. Various other factors affecting the structural integrity of the post-operative bone and implant arrangement may be taken into account, such as the patient's weight and lifestyle. The structural integrity of the post-operative bone and implant arrangement is analyzed to determine whether the arrangement will be structurally sound and kinematically functional post-operatively. If the analysis uncovers structural weaknesses or kinematic concerns, the surgical plan can be modified to achieve a desired post-operative structural integrity and function.

Once the surgical plan has been finalized, a surgeon may perform the arthroplasty procedure with the assistance of haptic device 60 (step 806). Through haptic device 60, the surgical system 100 provides haptic guidance and feedback to the surgeon to help the surgeon accurately implement the surgical plan. Haptic guidance and feedback during an arthroplasty procedure allows for greater control of the surgical tool compared to conventional arthroplasty techniques, resulting in more accurate alignment and placement of the implant. Furthermore, haptic guidance and feedback is intended to eliminate the need to use K-wires and fluoroscopy for planning purposes. Instead, the surgical plan is created and verified using the three-dimensional representation of the patient's anatomy, and the haptic device provides guidance during the surgical procedure.

"Haptic" refers to a sense of touch, and the field of haptics relates to human interactive devices that provide tactile and/or force feedback to an operator. Tactile feedback generally includes tactile sensations such as, for example, vibration. Force feedback (also known as "wrench") refers to feedback in the form of force (e.g., resistance to movement) and/or torque. Wrench includes, for example, feedback in the form of force, torque, or a combination of force and torque. Haptic feedback may also encompass disabling or altering the amount of power provided to the surgical tool, which can provide tactile and/or force feedback to the user.

Surgical system 100 provides haptic feedback to the surgeon based on a relationship between surgical tool 58 and at least one of the working boundaries. The relationship between surgical tool 58 and a working boundary can be any suitable relationship between surgical tool 58 and a working boundary that can be obtained by the navigation system and utilized by the surgical system 100 to provide haptic feedback. For example, the relationship may be the position, orientation, pose, velocity, or acceleration of the surgical tool 58 relative to one or more working boundaries. The relationship may further be any combination of position, orientation, pose, velocity, and acceleration of the surgical tool 58 relative to one or more working boundaries. The "relationship" between the surgical tool 58 and a working boundary may also refer to a quantity or measurement resulting from another relationship between the surgical tool 58 and a working boundary. In other words, a "relationship" can be a function of another relationship. As a specific example, the "relationship" between the surgical tool 58 and a working boundary may be the magnitude of a haptic force generated by the positional relationship between the surgical tool 58 and a working boundary.

During operation, a surgeon manipulates the haptic device 60 to guide a surgical tool 58 coupled to the device. The surgical system 100 provides haptic feedback to the user, through haptic device 60, to assist the surgeon during creation of the planned holes, cuts, or other modifications to the patient's bone needed to facilitate implantation of the femoral and tibial implants. For example, the surgical system 100 may assist the surgeon by substantially preventing or constraining the surgical tool 58 from crossing a working boundary. The surgical system 100 may constrain the surgical tool from crossing a working boundary by any number and combination of haptic feedback mechanisms, including by providing tactile feedback, by providing force feedback, and/or by altering the amount of power provided to the surgical tool. "Constrain," as used herein, is used to describe a tendency to restrict movement. Therefore, the surgical system may constrain the surgical tool 58 directly by applying an opposing force to the haptic device 60, which tends to restrict movement of the surgical tool 58. The surgical system may also constrain the surgical tool 58 indirectly by providing tactile feedback to alert a user to change his or her actions, because alerting a user to change his or her actions tends to restrict movement of the surgical tool 58. In a still further embodiment, the surgical system 100 may constrain the surgical tool 58 by limiting power to the surgical tool 58, which again tends to restrict movement of the tool.

In various embodiments, the surgical system 100 provides haptic feedback to the user as the surgical tool 58 approaches a working boundary, upon contact of the surgical tool 58 with the working boundary, and/or after the surgical tool 58 has penetrated the working boundary by a predetermined depth. The surgeon may experience the haptic feedback, for example, as a vibration, as a wrench resisting or actively opposing further movement of the haptic device, or as a solid "wall" substantially preventing further movement of the haptic device. The user may alternatively experience the haptic feedback as a tactile sensation (e.g. change in vibration) resulting from alteration of power provided to the surgical tool 58, or a tactile sensation resulting from cessation of power provided to the tool. If power to the surgical tool is altered or stopped when the surgical tool 58 is drilling, cutting, or otherwise operating directly on bone, the surgeon will feel haptic feedback in the form of resistance to further movement because the tool is no longer able to drill, cut, or otherwise move through the bone. In one embodiment, power to the surgical tool is altered (e.g. power to the tool is decreased) or stopped (e.g. the tool is disabled) upon contact between the surgical tool 58 and a working boundary. Alternatively, the power provided to the surgical tool 58 may be altered (e.g. decreased) as the surgical tool 58 approaches a working boundary.

In another embodiment, the surgical system 100 may assist the surgeon in creating the planned holes, cuts, and other modifications to the bone by providing haptic feedback to guide the surgical tool 58 towards or along a working boundary. As one example, the surgical system 100 may provide forces to the haptic device 60 based on a positional relationship between the tip of surgical tool 58 and the closest coordinates of a working boundary. These forces may cause the surgical tool 58 to approach the closest working boundary. Once the surgical tool 58 is substantially near to or contacting the working boundary, the surgical system 100 may apply forces that tend to guide the surgical tool 58 to move along a portion of the working boundary. In another embodiment, the forces tend to guide the surgical tool 58 to move from one portion of the working boundary to another portion of a working boundary (e.g. from a funnel-shaped portion of the working boundary to a rectangular box-shaped portion of a working boundary).

In yet another embodiment, the surgical system 100 is configured to assist the surgeon in creating the planned holes, cuts, and modifications to the bone by providing haptic feedback to guide the surgical tool from one working boundary to another working boundary. For example, the surgeon may experience forces tending to draw the surgical tool 58 towards working boundary 66 when the user guides the surgical tool 58 towards working boundary 66. When the user subsequently removes the surgical tool 58 from the space surrounded by working boundary 66 and manipulates the haptic device 60 such that the surgical tool 58 approaches a second working boundary (not shown), the surgeon may experience forces pushing away from working boundary 66 and towards the second working boundary.

Haptic feedback as described herein may operate in conjunction with modifications to the working boundaries by the surgical system 100. Although discussed herein as modifications to "working boundaries," it should be understood that the surgical system 100 modifies the virtual boundaries, which correspond to the working boundaries. Some examples of modifications to a working boundary include: 1) reconfiguration of the working boundary (e.g. a change in shape or size), and 2) activating and deactivating the entire working boundary or portions of the working boundary (e.g. converting "open" portions to "active" surfaces and converting "active" surfaces to "open" portions). Modifications to working boundaries, similarly to haptic feedback, may be performed by the surgical system 100 based on a relationship between the surgical tool 58 and one or more working boundaries. Modifications to the working boundaries further assist a user in creating the required holes and cuts during an arthroplasty procedure by facilitating a variety of actions, such as movement of the surgical tool 58 towards a bone and cutting of the bone by the surgical tool 58.

In one embodiment, modifications to the working boundary facilitate movement of the surgical tool 58 towards a bone 10. During a surgical procedure, because the patient's anatomy is tracked by the navigation system, the surgical system 100 moves the entirety of working boundary 66 in correspondence with movement of the patient's anatomy. In addition to this baseline movement, portions of working boundary 66 may be reshaped and/or reconfigured to facilitate movement of the surgical tool 58 towards the bone 10. As one example, the surgical system may tilt funnel-shaped portion 66 b of working boundary 66 relative to the rectangular box-shaped portion 66 a during the surgical procedure based on a relationship between the surgical tool 58 and the working boundary 66. The working boundary 66 can therefore be dynamically modified during the surgical procedure such that the surgical tool 58 remains within the space surrounded by the portion 66 b of working boundary 66 as the surgical tool 58 approaches the bone 10.

In another embodiment, working boundaries or portions of working boundaries are activated and deactivated. Activating and deactivating entire working boundaries may assist a user when the surgical tool 58 is approaching the bone 10. For example, a second working boundary (not shown) may be deactivated during the time when the surgeon is approaching the first working boundary 66 or when the surgical tool 58 is within the space surrounded by the first working boundary 66. Similarly, the first working boundary 66 may be deactivated after the surgeon has completed creation of a first corresponding resection and is ready to create a second resection. In one embodiment, working boundary 66 may be deactivated after surgical tool 58 enters the area within the funnel-portion leading to the second working boundary but is still outside of first funnel-portion 66 b. Activating a portion of a working boundary converts a previously open portion (e.g. open top 67) to an active surface of the working boundary. In contrast, deactivating a portion of the working boundary converts a previously active surface (e.g. the end portion 66 c of working boundary 66) of the working boundary to an "open" portion.

Activating and deactivating entire working boundaries or their portions may be accomplished dynamically by the surgical system 100 during the surgical procedure. In other words, the surgical system 100 may be programmed to determine, during the surgical procedure, the presence of factors and relationships that trigger activation and deactivation of virtual boundaries or portions of the virtual boundaries. In another embodiment, a user can interact with the surgical system 100 (e.g. by using the input device 52) to denote the start or completion of various stages of the arthroplasty procedure, thereby triggering working boundaries or their portions to activate or deactivate.

In view of the operation and function of the surgical system 100 as described above, the discussion will now turn to methods of preoperatively planning the surgery to be performed via the surgical system 100, followed by a detailed discussion of methods of registering the preoperative plan to the patient's actual bone and also to applicable components of the surgical system 100.

The haptic device 60 may be described as a surgeon-assisted device or tool because the device 60 is manipulated by a surgeon to perform the various resections, drill holes, etc. In certain embodiments, the device 60 may be an autonomous robot, as opposed to surgeon-assisted. That is, a tool path, as opposed to haptic boundaries, may be defined for resecting the bones and drilling holes since an autonomous robot may only operate along a pre-determined tool path such that there is no need for haptic feedback. In certain embodiments, the device 60 may be a cutting device with at least one degree of freedom that operates in conjunction with the navigation system 42. For example, a cutting tool may include a rotating burr with a tracker on the tool. The cutting tool may be freely manipulate-able and handheld by a surgeon. In such a case, the haptic feedback may be limited to the burr ceasing to rotate upon meeting the virtual boundary. As such, the device 60 is to be viewed broadly as encompassing any of the devices described in this application, as well as others.

II. Preoperative Planning of Arthroplasty Procedure

The preoperative planning process disclosed herein includes a bone resection depth determination and an anterior shaft notching assessment. The bone resection depth determination includes selecting and positioning three dimensional computer models of candidate femoral and tibial implants relative to three dimensional computer models of the patient's distal femur and proximal tibia to determine a position and orientation of the implants that will achieve a desirable surgical outcome for the arthroplasty procedure. As part of this assessment, the depths of the necessary tibial and femoral resections are calculated, along with the orientations of the planes of those resections.

The anterior shaft notching assessment includes determining whether or not an anterior flange portion of the three dimensional model of the selected femoral implant will intersect the anterior shaft of the three dimensional model of the patient's distal femur when the implant three dimensional model is positioned and oriented relative to the femur three dimensional model as proposed during the bone resection depth determination. Such an intersection of the two models is indicative of notching of the anterior femoral shaft, which must be avoided.

Each of these two preoperative planning processes is discussed below in detail and in turn.

A. Bone Resection Depth

FIGS. 4A and 4B respectively illustrate three dimensional computer models 200, 202 of a proximal end of a generic tibia 200 and a distal end of a generic femur 202. In certain embodiments, each three dimensional model represents a statistical average of its respective bone type according to both size and shape. For example, in one embodiment, generic tibia model 200 is a result of an analysis of the medical images (e.g., CT, MRI, X-ray, etc.) of many (e.g., thousands or tens of thousands) of actual tibias with respect to size and shape, and this analysis is used to generate the generic tibia model 200, which is a statistical average of the many actual tibias. Similarly, generic femur model 202 is a result of an analysis of the medical images (e.g., CT, MRI, X-ray, etc.) of many (e.g., thousands or tens of thousands) of actual femurs with respect to size and shape, and this analysis is used to generate the generic femur model 202, which is a statistical average of the many actual femurs.

In certain embodiments, each three dimensional model represents a randomly selected bone from a catalog or library of bones. The library of bones may include computer models of actual bones (e.g., cadaveric) and/or computer models of medical bone models, among others. While the models 200, 202 could be any such bone models, for the purposes of the present disclosure, reference will be made to the generic tibia 200 and generic femur 202 as representing a statistical average of a tibia and femur, respectively, according to size and shape. As indicated in FIG. 4A, target points 204, 208 are identified on the generic tibia model 200. In certain embodiments, as seen in FIG. 4A, the most distally recessed point 204 on the tibial lateral condyle recess 206 and the most distally recessed point 208 on the tibial medial condyle recess 210 are identified and electronically stored along with the generic tibia model 200. Such most distally recessed tibial condyle points 204, 208 will typically be centered medial-lateral and anterior-posterior in the respective tibial condyle recesses 206, 210. The most distally recessed tibial condyle points 204, 208 may be depicted on the generic tibia model 200 as circular or spherical points, as shown in FIG. 4A. In certain embodiments, the target points 204, 208 may be located on other portions of the tibia model 200. For example, in certain embodiments, the target points 204, 208 may be the most proximally proud or most proximally extending point on the generic tibia model 200. Additionally, in certain embodiments, the target points 204, 208 may be the center of the condyles, or points located a certain fraction (e.g., ⅔) from the anterior edge, which may represent a low point on a tibial insert implanted on the generic tibia model 200. These and other points 204, 208 are possible without departing from the scope of the present disclosure. For the purposes of the present disclosure, reference will be made to the most distally recessed point 204 on the tibial lateral condyle recess 206 and the most distally recessed point 208 on the tibial medial condyle recess 210.

As illustrated in FIG. 4B, the most distal point 212 and the most posterior point 214 on the femoral lateral condyle 216 and the most distal point 218 and the most posterior point 220 on the femoral medial condyle 222 are identified and electronically stored along with the generic femur model 202. The most distal femoral condyle points 212, 218 and most posterior femoral condyle points 214, 220 may be depicted on the generic femur model 202 as circular or spherical points, as depicted in FIG. 4B. In FIG. 4B, the distal points 212, 218 and the posterior points 214, 220 are identified on the generic femur model 202 when the model 202 is at zero degrees rotation in the sagittal plane. That is, the femur model 202 is in an un-flexed position or orientation. The generic femur model 202, however, may be rotated in the sagittal plane to adjust for the planned flexion of the femoral component to be implanted on the femur. In certain embodiments, the generic femur model 202 may be rotated two degrees, among other degrees, in the sagittal plane, and the distal points 212, 218 and the posterior points 214, 220 may be identified on the model 202 in this flexed orientation.

As discussed above in the overview of the surgical system, medical images of the patient tibia and femur are segmented and then complied into three dimensional meshes or computer models of the patient tibia and femur. FIGS. 5A-5C respectively illustrate coronal, axial or transverse, and sagittal views of the proximal end of the three dimensional computer model of the patient tibia (i.e., the patient tibia model 224), and FIGS. 6A-6C respectively illustrate coronal, axial or transverse, and sagittal views of the distal end of the three dimensional computer model of the patient femur (i.e., patient femur model 226). While the three dimensional computer models of the patient tibia and femur are described as being generated from segmenting medical images (e.g., CT, MRI), it is foreseen that other methods of generating patient models may be employed. For example, patient bone models or portions thereof may be generated intra-operatively via registering a bone or cartilage surface in one or more areas of the bone. Such a process may generate one or more bone surface profiles. Thus, the various methods described herein are intended to encompass three dimensional bone models generated from segmented medical images (e.g., CT, MRI) as well as intra-operative imaging methods, and others.

1. Fine-Tuning Most Distally Recessed Tibial Condyle Points on Patient Tibia Model As can be understood from a comparison of FIGS. 4A and 5A-5C, the most distally recessed tibial condyle points 204, 208 of the generic tibial model 200 have been imported or mapped onto the corresponding locations of the patient tibia model 224. An affine transformation is used to map the points 204, 208 from the generic tibial model 200 to the patient tibia model 224. More specifically, the target points 204, 208 from the generic tibial model 200 are mapped onto/into the patient tibial model 224 by first transforming the target points 204, 208 using the already computed affine transform and then finding the closest surface point from each transformed target point to the segmented surface of the patient tibial model 224. As a result and as can be understood from FIGS. 5A-5C, the most distally recessed tibial condyle points 204, 208 end up being positioned at or very close to the most distally recessed locations on the lateral and medial tibial condyles of the patient tibia model 224. In some embodiments and instances, the locations of the points 204, 208 may be scaled according to the medial-lateral scaling factor between generic and patient models 200, 224. The transformation process may be similarly accomplished with alternative, previously mentioned target points 204, 208 such as the center of the condyle, the most proximally proud lateral condyle, etc. Generally speaking, any target point(s) on the generic bone model may be transformed to the patient specific bone model such that the target points 204, 208 end up being positioned at or very close to the desired locations on the patient specific bone model.

It is noted that the generic model 200 and the patient tibia model 224 may share a common coordinate system to aid in initial alignment. The origin of the patient tibia model 224 may be the top center of the tibia as defined by a CT landmarking process. The system or user may define these points. The generic model 200 may have a predefined origin selected by the system or a user in the same manner as is done for the patient tibia model 224.

Refinement of the distally recessed tibial condyle points 204, 208 may be accomplished by identifying the real local minimum on the patient tibia model 224, identifying the real local maximum on the patient tibia model 224, identifying an edge location (e.g., anterior edge), identifying a tangential point, and finding a point where the surface matches a certain slope, etc. Additional or alternative refinement of the distally recessed tibial condyle points 204, 208 may utilize similar methods and functions described in reference to the femur.

The patient tibia model 224 and the points 204, 208 thereon may be depicted on the display 54 as a three dimensional computer model capable of being rotated and moved. Additionally or alternatively, the patient tibia model 224 and the points 204, 208 thereon may be depicted on the display 54 in three different views, namely, a coronal view, an axial or transverse view, and a sagittal view as respectively illustrated in FIGS. 5A-5C. Where one or more of the points 204, 208 is hidden by bone structure of the model 224, for example, as is the case in FIGS. 5A and 5C, the hidden points 204, 208 may be depicted translucent or in another depiction that indicates the points are present, but located behind some bone structure in the view. In certain embodiments where one or more of the points 204, 208 is hidden by the bone structure of the model 224, the bone model 224 may be depicted translucent, so the points 204, 208 are identifiable behind the occluding bone structure. Where the one or more of the points 204, 208 are fully visible in a view (in other words, not hidden by bone structure of the model 224), as is in the case of FIG. 5B, the visible points 204, 208 may be depicted as solid fully visible points to indicate the points are not hidden by bone structure of the model 224 but are fully visible in the view.

These points 204, 208, when properly positioned on the patient tibia model 224, can serve as bone resection depth points to be used to calculate the depth of bone resections to the patient tibia that will allow a selected tibial implant (in conjunction with a selected femur implant) to achieve a desired surgical outcome when the actual implants are implanted onto the patient's tibia and femur as part of the arthroplasty procedure preoperatively planned as described herein.

Once the target points, such as the most distally recessed tibial condyle points 204, 208, have been properly located on the patient tibia model 224 as described above, these points 204, 208 can be used with a three dimensional computer model of a candidate tibial implant 300, or data associated with such an implant 300, to preoperatively calculate the associated bone resections that need to be made in the actual patient bone to receive the actual tibial implant to achieve a desired surgical outcome from implanting the actual tibial implant onto the actual patient bone during the actual arthroplasty procedure.

Figure 11:
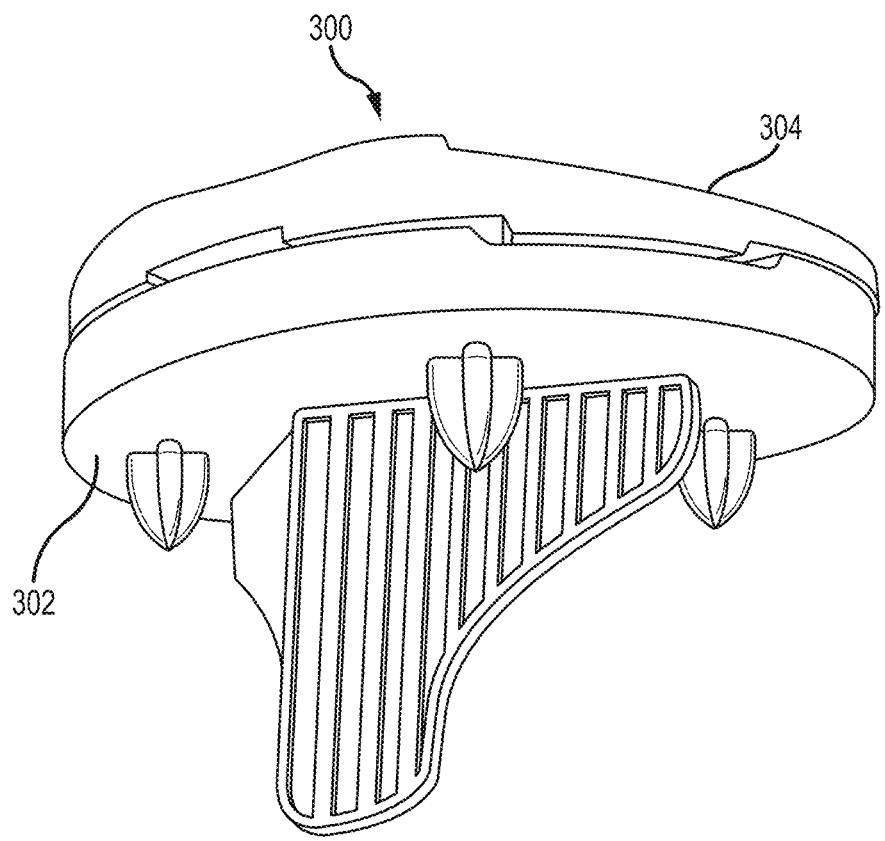
FIG. 11 is a distal-anterior view of a three dimensional computer model of the candidate tibial implant (i.e., the tibial implant model) illustrating its bone resection contacting surface distally opposite its tibial plateau.

FIG. 11 is a distal-anterior view of a three dimensional computer model of the candidate tibial implant (i.e., the tibial implant model 300) illustrating its bone resection contacting surface 302 distally opposite its tibial plateau 304. As can be understood from FIGS. 12A-12C, which respectively illustrate coronal, axial or transverse, and sagittal views of the tibial implant model 300 superimposed on the proximal end of the three dimensional computer model of the patient tibia (i.e., the patient tibia model 224), one or both of the points 204, 208 may be aligned with a similar or equivalent most distally recessed tibial condyle point or region on the articular surface of the tibial plateau 304 of the implant model 300, thereby defining a proposed tibial resection 306 that extends along the bone resection contacting surface 302 of the implant model 300. The defined proposed tibial resection 306 is defined according to resection depth and planar orientation. Of course, the defined proposed tibial resection 306 can be adjusted or modified by preoperative, and/or in some embodiments, intraoperative, surgeon input by changing the resection depth distally or proximally relative to the points 204, 208, changing the size of the candidate tibial implant model 300 to a smaller or larger size, changing the planar orientation of the proposed resection 306 to account for a desired varus-valgus, internal-external, or extension-flexion rotation, to cause both points 204, 208 or only a single point 204, 208 to correspond to similar points on the lateral and medial articular surfaces of the tibial plateau 304 of the implant model 300, depending on whether or not an anatomic (natural) alignment is sought or a more traditional mechanical axis alignment is sought.

Figure 12C:
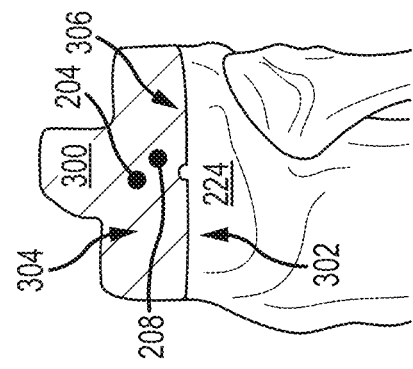
FIGS. 12A-12C respectively illustrate coronal, axial or transverse, and sagittal views of the tibial implant model superimposed on the proximal end of the three dimensional computer model of the patient tibia (i.e., the patient tibia model).
Figure 12B:
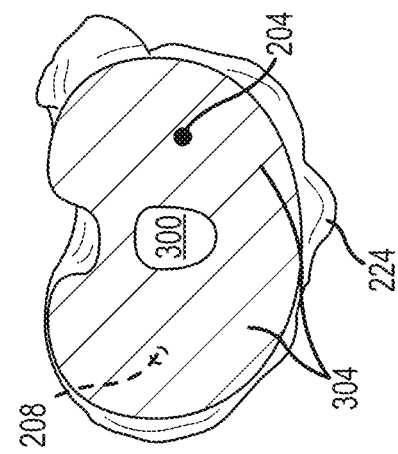
Figure 12A:
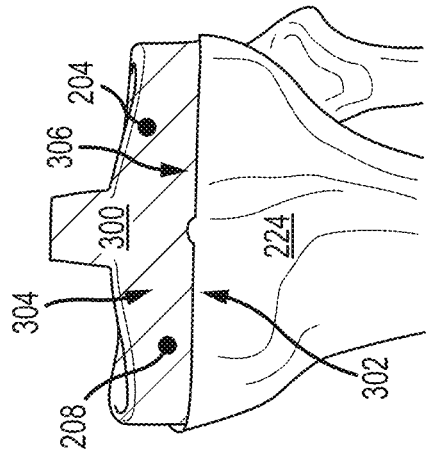
Figure 15C:
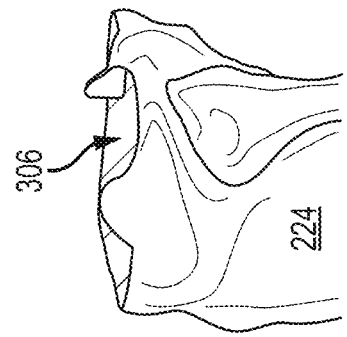
FIGS. 15A-15C are various views of the tibia model as proposed to be resected and illustrating the proposed tibial resection.
Figure 15B:
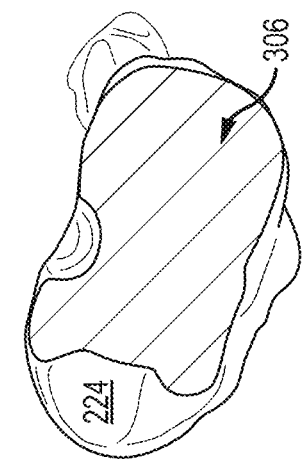
Figure 15A:
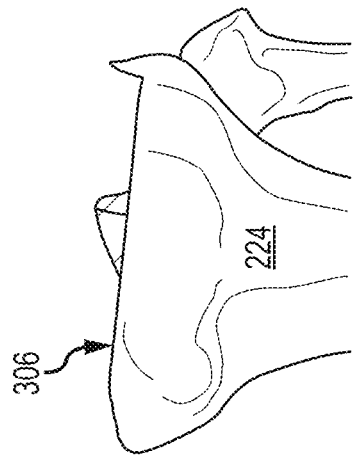

FIGS. 12A-12C are illustrative of a situation where just a single point 204, 208 is aligned with a similar point or region on one of the articular surfaces of the tibial plateau 304 of the implant model 300. For example, as can be seen in FIGS. 12A and 12C, the lateral point 204 is aligned with a similar point or region on the lateral articular surface of the tibial plateau 304 of the implant model 300, but the medial point 208 is not aligned with its similar point or region on the medial plateau of the implant model 300. Thus, as can be understood from FIG. 12B, the medial point 208 is shown in dashed lines to represent that it would appear as transparent on the computer display 54 due to being recessed within the volume of the implant model 300, and the lateral point 208 is shown as a solid circle to represent that it would appear solid on the computer display due to being on the lateral articular surface of the tibial plateau of the implant model 300. It is noted that the tibial implant model 300 may be depicted transparently so that the resection depth is visible through the implant model 300. With only the single matching of the points, which happens to be on the lateral side, the orientation of the bone resection contacting surface 302 of the implant model 300, and as a result, the orientation of the proposed resection plane 306, is then determined by maintaining the matching of the lateral points while achieving a desired angle of the proposed resection plane 306 relative to an axis of the patient's leg, femur or tibia, such as, for example, the tibial mechanical axis or leg mechanical axis. Once the surgeon has approved the depth and orientation of the proposed tibial resection plane 306, the associated data can be provided to the surgical system 100 for use by the navigation system in guiding the haptic device 60 during the surgery, and the resected patient tibia model 224 may be represented to the surgeon intra-operatively as indicated in FIGS. 15A-15C, which are various views of the tibia model 224 as proposed to be resected and illustrating the proposed tibial resection 306.

While the preceding discussion of defining the proposed tibial resection plane 306 has been made in the context of superimposing a candidate tibial implant 300 on the tibia model 224 and showing such superimposing visually on the computer display 54 of the system 100, in other embodiments, such a process can take place by data representative of the candidate tibial implant 300, not requiring a three dimensional representation of the candidate tibial implant or its actual visual representation on the computer display 54.

2. Fine-Tuning Most Posterior and Most Distal Femoral Condyle Points on Patient Femur Model As can be understood from a comparison of FIGS. 4B and 6A-6C, the most distal femur condyle points 212, 218 and the most posterior femur condyle points 214, 220 of the generic femoral model 202 have been imported or mapped onto the corresponding locations of the patient femur model 226. As discussed with reference to the tibial transformation, an affine transform is used to map the points 212, 214, 218, 220 from the generic femur model 202 to the patient femur model 226. As a result and as can be understood from FIGS. 6A-6C, the most distal femoral condyle points 212, 218 end up being positioned at or very close to the most distal locations on the lateral and medial femoral condyles of the patient femur model 226. Similarly, the most posterior femoral condyle points 214, 220 end up being positioned at or very close to the most posterior locations on the lateral and medial femoral condyles of the patient femur model 226. In some embodiments and instances, the locations of the points 212, 214, 218, 220 may be scaled according to the medial-lateral scaling factor between generic and patient models 202, 226. In some embodiments and instances, the affine transform may incorporate the scaling functionality.

It is noted that the generic model 202 and the patient femur model 226 may share a common coordinate system to aid in initial alignment. The origin of the patient femur model 226 for a total knee arthroplasty may be the distal trochlear groove, as defined by a CT landmarking process. The origin of the patient femur model 226 for a partial knee arthroplasty may be the midpoint center between the medial and lateral epicondyles, as defined by a CT landmarking process. The system or user may define these points. The generic model 202 may have a predefined origin selected by the system or a user in the same manner as is done for the patient femur model 226.

In one embodiment, the "most distal" and "most posterior" points on the femoral condyle surfaces are used in the sense of a femoral implant placed at two degrees of flexion or at another degree of flexion as reviewed and directed by a surgeon. Also, for any of the points 204, 208 of the tibia model 224 or the points 212, 214, 218, 220 of the femur model 226, these points should not be placed on an osteophyte or any other surface on the models not likely to be referenced or used by a surgeon in the preoperative planning. Determining whether or not the points 204, 208, 212, 214, 218, 220 lie on an osteophyte will be discussed below.

Once the points 212, 214, 218, 220 have been initially mapped onto the patient femur model 226 from the generic femur model 202 via the affine transform, the locations of the points 212, 214, 218, 220 on the patient femur model 226 are adjusted to final locations via an algorithm that functions as now described.

A virtual implant coordinate system is placed at two degrees of flexion from the femoral mechanical axis coordinate space. The anterior-posterior and proximal-distal direction of this coordinate system is used in the following discussion regarding the femur resection depth points.

Figure 7:
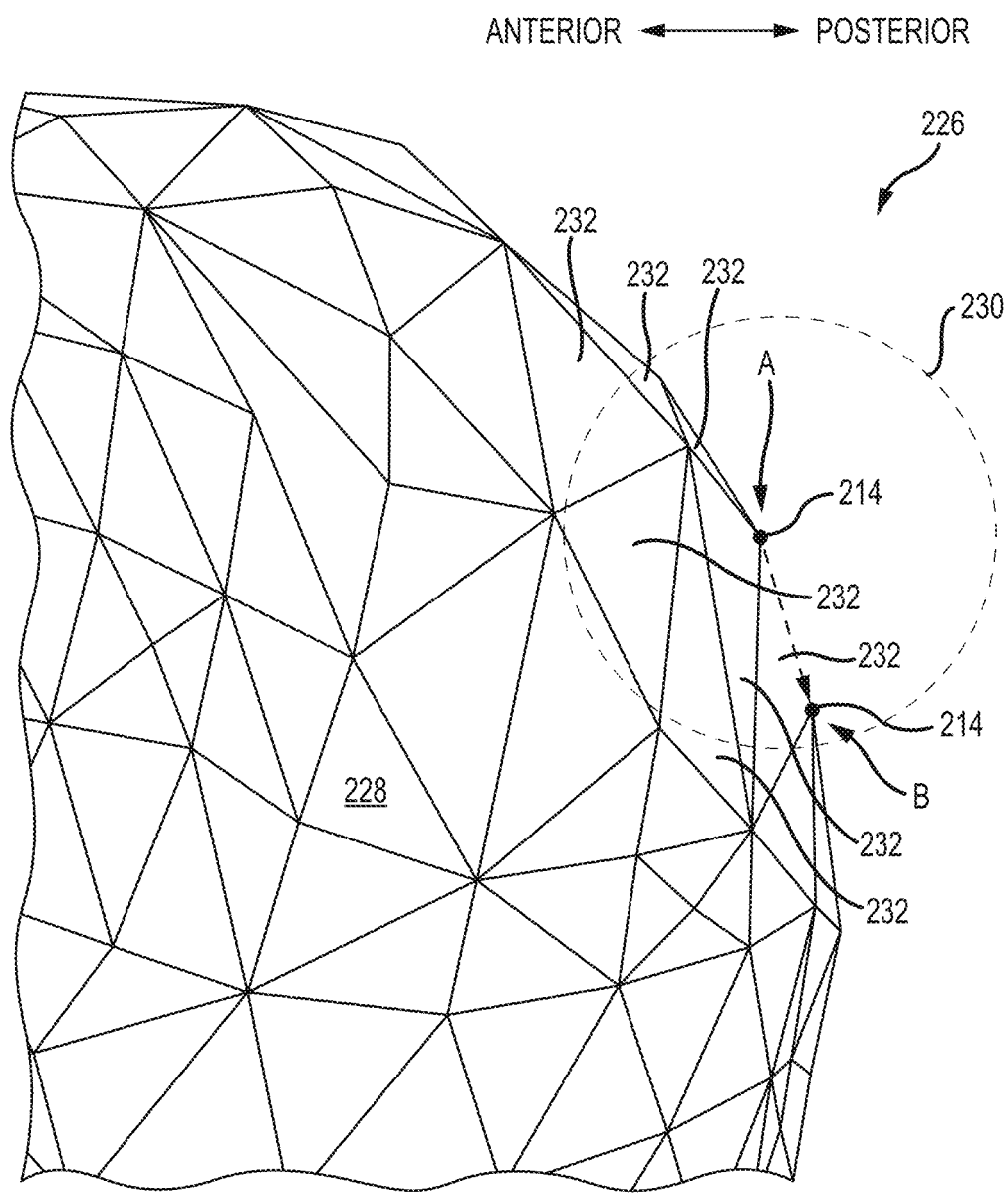
FIG. 7 is an enlarged view of a triangular surface mesh of a posterior condylar region of a three dimensional patient femur computer model and illustrating a method of adjusting the location of posterior points on the patient femur model that were mapped onto the patient femur model from a three dimensional generic femur computer model.
Figure 8:
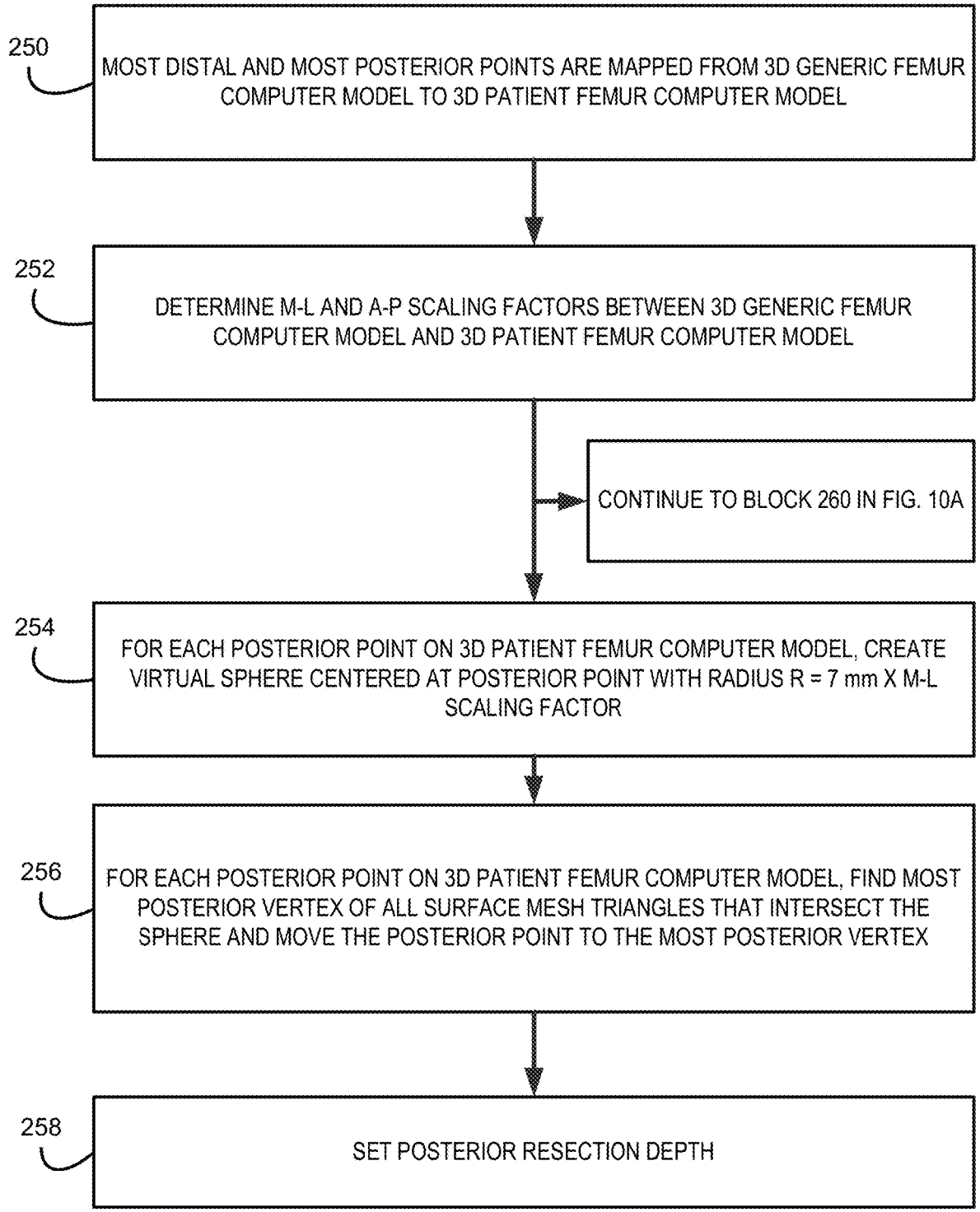
FIG. 8 is a flow chart illustrating the method of adjusting the placement of the mapped posterior points on the patient femur model.

As discussed in detail in the immediately following paragraphs with respect to FIGS. 7 and 8, for each of the two posterior points 214, 220, the algorithm conducts a search around the initial location of each point 214, 220, and the final adjusted location of each point 214, 220 is determined to be the most posterior vertex of all triangular surface mesh faces intersecting a sphere centered at or near the initial location of each point 214, 220. In one embodiment, the radius of the sphere 230 is seven millimeters if the patient femur model 226 substantially matches the generic femur model 202 with respect to medial-lateral size. If scaling is needed due to medial-lateral size differences between the patient femur model 226 and the generic femur model 202, then the sphere 230 may be scaled larger or smaller than seven millimeters in radius depending on the scaling between the two models 202, 226.

Thus, as can be understood from FIGS. 7 and 8, which are, respectively, an enlarged view of a triangular surface mesh 228 of a posterior condylar region of a three dimensional patient femur computer model 226 and a flow chart outlining the method of adjusting the placement of the mapped posterior points 214, 220 on the patient femur model 226, the posterior points 214, 220 are mapped from the generic femur model 202 to the condyles of the patient femur model 226 [block 250]. The medial-lateral and anterior-posterior scaling factors are determined between the generic femur model 202 and the patient femur model 226, and these scaling factors are stored for later use [block 252]. For each posterior point 214, 220 on the patient femur model, a virtual sphere 230 is centered at the point 214, 220, the sphere 230 having a radius R that is 7 mm multiplied by the medial-lateral scaling factor [block 254].

As illustrated in FIG. 7, the initial location of a posterior point 214 mapped from the generic femur model 202 onto the patient femur model 226 is indicated at the location called out by Arrow A. As seen in FIG. 7, the posterior point 214 is located on the surface mesh 228 as computed by the affine transform. In the case of other transforms, the point 214 may, however, be spaced outwardly apart from the triangular surface mesh 228 or be recessed within the triangular surface mesh 228. The initial location at Arrow A of the posterior point 214 is surrounded by the sphere 230, which, as discussed above, may have a radius of seven millimeters or other radii depending on M-L scaling between the two models 202, 226. The sphere 230 intersects a number of triangular faces 232 and vertices of the surface mesh 228, and the algorithm adjusts (i.e., moves) the posterior point 214 as indicated by the dashed arrow to the vertex that is most posterior of any of the vertexes of any of the triangular faces 232 intersected by the sphere 230 [block 256]. The resulting adjusted final location of the posterior point 214 on the patient femur model 226 is indicated by Arrow B in FIG. 7. The posterior resection depth is then determined based on the adjusted final location of the posterior point 214 [block 258]. The surgical system 100 may then generate resection data using the posterior resection depth. The resection data may be used during the intraoperative part of the arthroplasty procedure and be employed as a haptic boundary for controlling the haptic device 60 or surgical robot. Additionally or alternatively, the resection data may be utilized by a surgical robot during the arthroplasty procedure. Additionally or alternatively, the resection data may be utilized by a navigation system during the arthroplasty procedure. The navigation system may operate in conjunction with an autonomous robot or a surgeon-assisted device in performing the arthroplasty procedure. An autonomous robot, such as a cutting device with at least two degrees of freedom (e.g., rotating burr and translation capabilities) may perform the arthroplasty procedure with the resection data utilized as a tool path for performing a resection. A surgeon-assisted device, such as the haptic device 60 described herein or a cutting tool with at least one degree of freedom (e.g., rotating burr moved or translated by a surgeon), may perform the arthroplasty procedure with the resection data being a virtual or haptic boundary for controlling or limiting certain movements of the cutting tool (e.g., depth of resection). Thus, the steps in FIG. 8 may describe a method of generating resection plane data for use in planning an arthroplasty procedure on a patient bone.

While a sphere 230 is described in the present disclosure, it is foreseen that other three-dimensional shapes may be employed instead of a sphere. For example, an ellipsoid, prism, or box, among other three-dimensional shapes may be used without limitation and without departing from the scope of the present disclosure. Additionally or alternatively, a two-dimensional shape such as a plane or a surface without a thickness may be used herein.

While the technique for identifying the location of the most posterior point 214 on the patient femur model 226 is not iterative, in certain embodiments, finding the location may be an iterative process. In certain instances, the bone surface at the posterior end may be relatively healthy and non-diseased. Thus, determining the location of the most posterior point 214 may be accomplished with a non-iterative approach.

As discussed in detail in the immediately following paragraphs with respect to FIGS. 8-10C, each of the two distal points 212, 218, the algorithm conducts a search around the initial location of each point 212, 218, and the final adjusted location of each point 212, 218 is determined to be the most distal of all surface mesh vertices located inside an ellipsoid 240 centered at or near the initial location of each point 212, 218 where X is in the medial-lateral direction, Y is in the anterior-posterior direction, and Z is in the proximal-distal direction. As the algorithm progresses through its iterations, the size of the ellipsoid 240 is dynamically adjusted, depending on whether: (1) the found most distal point is close to the boundary of the ellipsoid 240; and (2) the proximal-distal span of a region around the found point is large, indicating that the point is close to the medial-lateral edge of the condyle or close to osteophytes. A new most distal point is found after each ellipsoid iteration adjustment until the process is satisfied by finding the final most distal point 212, 218.

It is noted that while the present disclosure describes an ellipsoid 240, it is foreseen that other three-dimensional shapes may be employed instead of an ellipsoid. For example, a sphere, prism, or box, among other three-dimensional shapes may be used without limitation and without departing from the scope of the present disclosure. Additionally or alternatively, a two-dimensional shape such as a plane or a surface without a thickness may be used herein.

With respect to the operation of the algorithm as detailed below and mentioned immediately above, if the distal point is too close to the ellipsoid boundary, then this means that a more distal point exists outside the ellipsoid and the search ellipsoid is enlarged. As will become evident from the following discussion, this process is essentially repeated with some variation in size and shape of the search volume (i.e., the ellipsoid and later used spheres as discussed below) and checks on the process until the most distal point lies within the search volume and not on its edge. Also, as will become evident from the following discussion, one of the checks on the process is where the semi-minor axis $R_Z$ of the current iteration of the process has an excessive jump from the most distal point from the semi-minor axis $R_Z$ of the immediately preceding iteration of the process. If so, it is assumed the search volume has encompassed an osteophyte. In response to this osteophyte, the search volume is then reduced in size by the amount of the excessive jump and the most distal point is then found.

In one embodiment, the semi-minor axes (Rx and Rz) of the ellipsoid are equal and are each seven millimeters if the patient femur model 226 substantially matches the generic femur model 202 with respect to medial-lateral size. If scaling is needed due to medial-lateral size differences between the patient femur model 226 and the generic femur model 202, then the semi-minor axes of the ellipsoid may be scaled larger or smaller than seven millimeters depending on the M-L scaling between the two models 202, 226. Similarly, the semi-major axis (Ry) of the ellipsoid is ten millimeters if the patient femur model 226 substantially matches the generic femur model 202 with respect to anterior-posterior size. If scaling is needed due to anterior-posterior size differences between the patient femur model 226 and the generic femur model 202, then the semi-major axis of the ellipsoid may scaled larger or smaller than ten millimeters depending on the A-P scaling between the two models 202, 226.

Figure 9A:
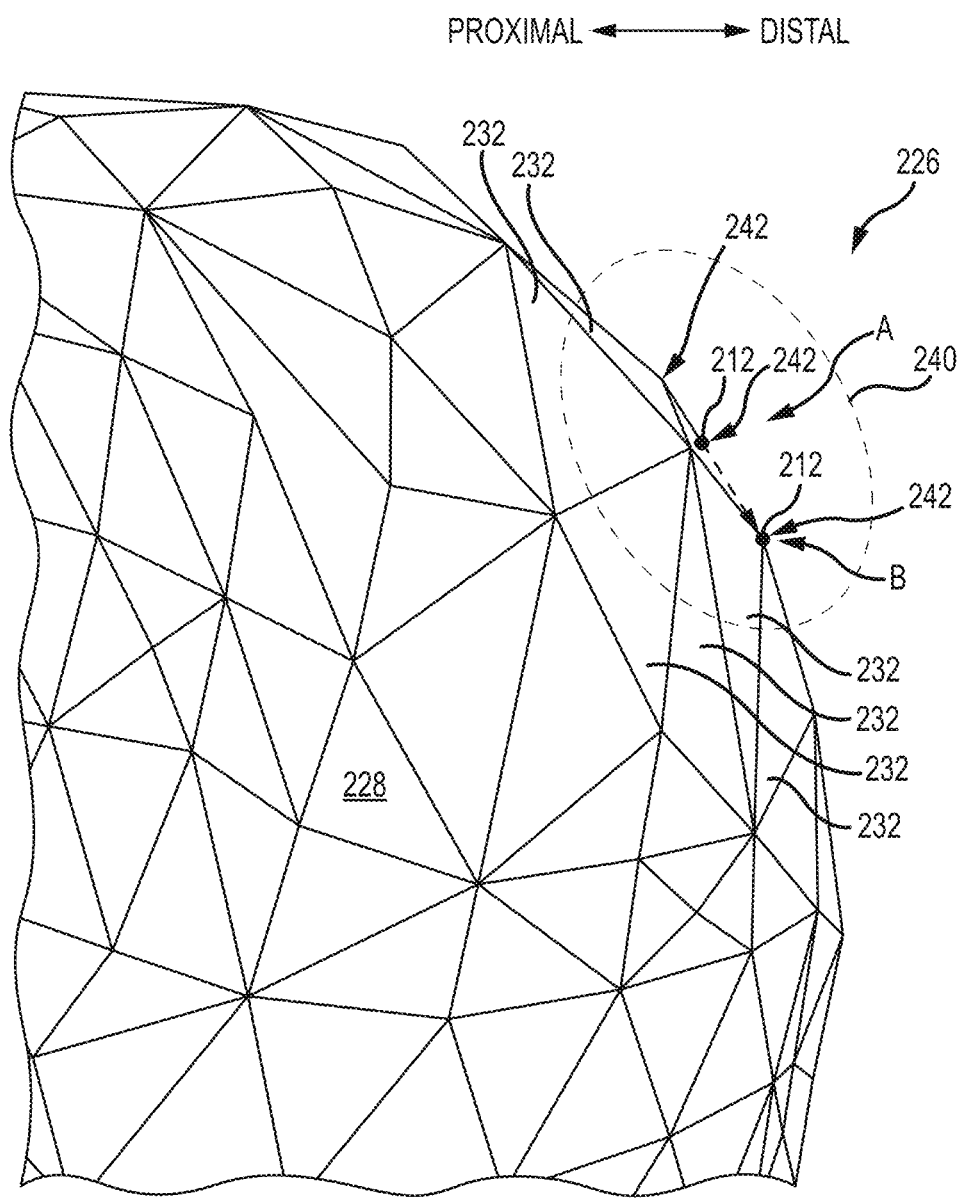
FIG. 9A is an enlarged view of a triangular surface mesh of a distal condylar region of a three dimensional patient femur computer model and illustrating a method of adjusting the location of distal points on the patient femur model that were mapped onto the patient femur model from a three dimensional generic femur computer model.
Figure 9B:
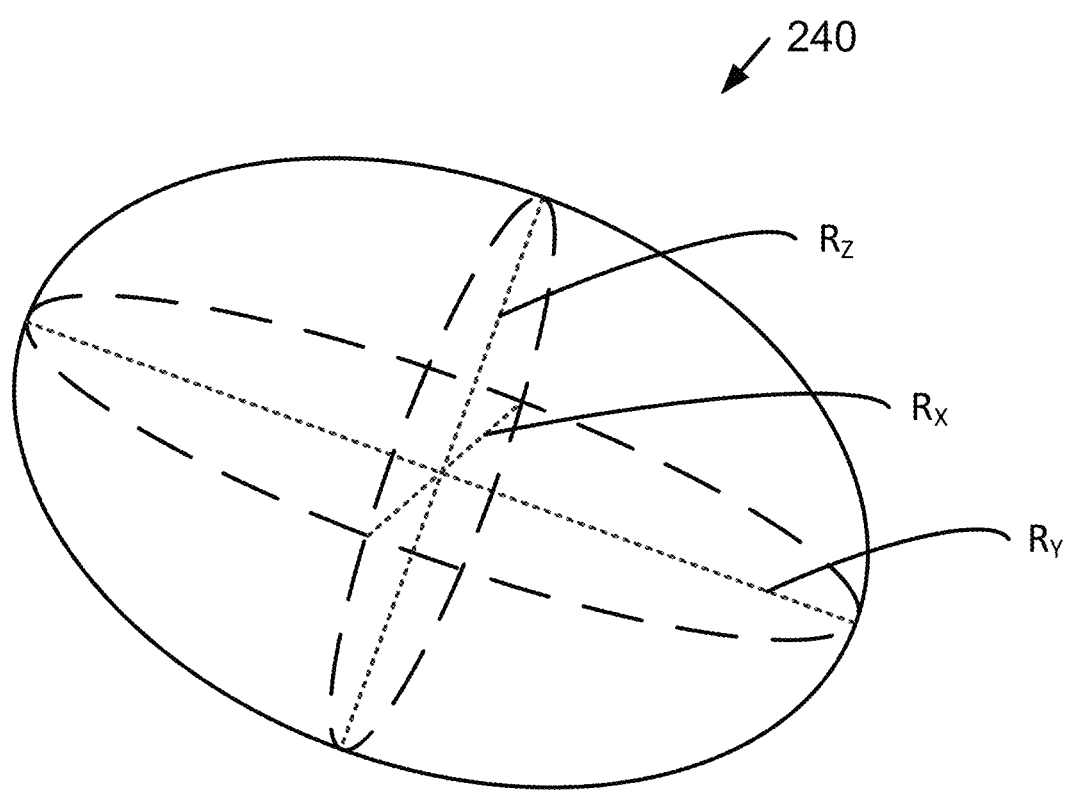
FIG. 9B is an enlarged isometric view of the ellipsoid employed in FIG. 9A.
Figure 10A:
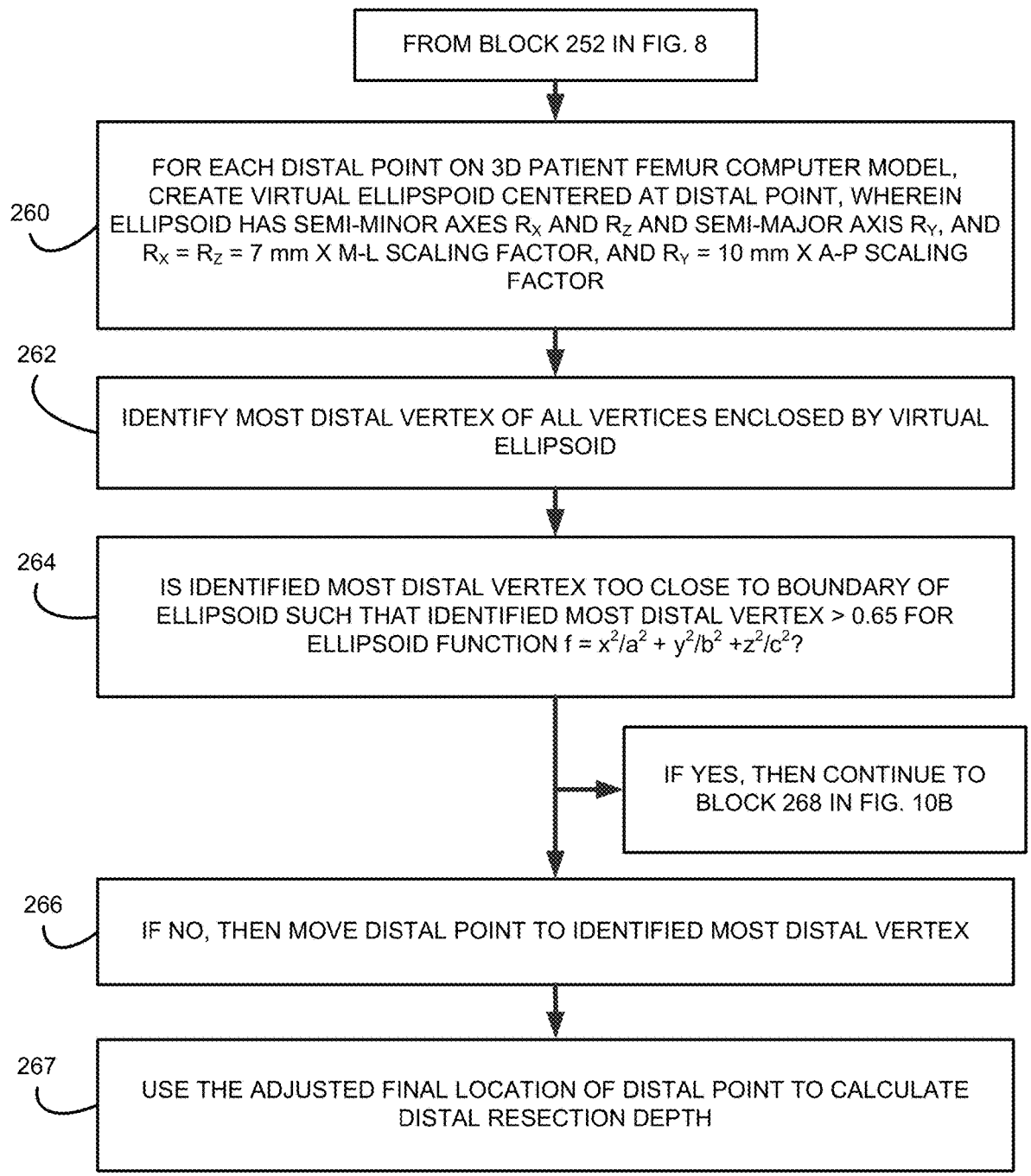
FIGS. 10A-10C is a flow chart outlining the method of adjusting the placement of the mapped distal points on the patient femur model, the distal points having been mapped from the generic femur model to the condyles of the patient femur model.

Thus, as can be understood from FIG. 8 and continued with FIGS. 9A and 10, which are, respectively, an enlarged view of a triangular surface mesh 228 of a distal condylar region of a three dimensional patient femur computer model 226, and a flow chart outlining the method of adjusting the placement of the mapped distal points 212, 218 on the patient femur model 226, the distal points 212, 218 are mapped from the generic femur model 202 to the condyles of the patient femur model 226 [block 250]. The medial-lateral and anterior-posterior scaling factors are determined between the generic femur model 202 and the patient femur model 226, and these scaling factors are stored for later use [block 252]. As shown in FIG. 9A and outlined in FIG. 10A, for each distal point 212, 218 on the patient femur model, a virtual ellipsoid 240 is centered at the point 212, 218, the ellipsoid 240 having semi-minor axes of $R_X$ and $R_Z$ and a semi-major axis $R_Y$, wherein $R_X$ and $R_Z$ each respectively equal 7 mm multiplied by the anterior-posterior scaling factor, and $R_Y$ equals 10 mm multiplied by the anterior-posterior scaling factor [block 260]. These axes $R_X$, $R_Z$ and $R_Y$ are illustrated in FIG. 9B, which is an enlarged isometric view of the ellipsoid 240 employed in FIG. 9A.

As illustrated in FIG. 9A, the initial location of a distal point 212 mapped from the generic femur model 202 onto the patient femur model 226 is indicated at the location called out by Arrow A, which is on the triangular surface mesh 228. As indicated previously, a different transform may position the initial distal point 212 spaced outwardly apart from the triangular surface mesh 228 or recessed within the triangular surface mesh 228, depending on the particular transform employed. The initial location at Arrow A of the distal point 212 on the surface mesh 228 is surrounded by the ellipsoid 240, which, as discussed above, may have semi-minor axes $R_X$, $R_Z$ that are each seven millimeters or other lengths depending on A-P scaling between the two models 202, 226, and a semi-major axis $R_Y$ this is ten millimeters or other lengths depending on A-P scaling between the two models 202, 226. The ellipsoid 240 encompasses a number of vertices 242 of the triangular faces 232 of the surface mesh 228, and the algorithm finds the most distal vertex of all the vertices 242 inside the ellipsoid 240, which is the vertex 242 identified in FIG. 9A by Arrow B [block 262]. The algorithm then assesses whether or not the most distal vertex 214 identified in FIG. 9A by Arrow B is too close to the boundary of the ellipsoid 240 [block 264].

In one embodiment, the algorithm defines an identified most distal vertex 242 (indicated by arrow B in FIG. 9A) as being too close to the boundary of the ellipsoid 240 if the functional result for the identified most distal vertex 242 is greater than 0.65 (non-dimensional) when the position of the identified most distal vertex 242 is applied to the ellipsoid function: $f=x^2/a^2+y^2/b^2+z^2/c^2$. In the ellipsoid function, x is Tx-Px, where Tx is the x-coordinate of the target point (A in FIG. 9C), and Px is the x-coordinate of the computed new distal point (B in FIG. 9C). That is, x is the distance, in the x-direction, from the center of the ellipse to the computed new distal point P. Similarly is the case for y and z in the ellipsoid function. That is, y is Ty-Py, where Ty is the y-coordinate of the target point, and Py is the y-coordinate of the computed new distal point. And, z is Tz-Pz, where Tz is the z-coordinate of the target point, and Pz is the z-coordinate of the computed new distal point. In the ellipsoid function: a is the radius, Rx=7 mm (total ML width of ellipse is 14 mm); b is the radius, Ry=10 mm (total AP length of ellipse is 20 mm); and, c is the radius, Rz=7 mm (total height of ellipse is 14 mm).

A value of 0.65 is equivalent to about 1.5 mm from the edge of the ellipse. Ultimately, if the identified most distal vertex 242 is not too close to the boundary of the ellipsoid 240 (e.g., 1.5 mm from edge), then, as indicated by the dashed arrow in FIG. 9A, the distal point 212 is moved to the identified most distal vertex 242 indicated in FIG. 9A by arrow B as being the most distal vertex [block 266], the resulting adjusted final location of the distal point 212 on the patient femur model 226 being as indicated by Arrow B in FIG. 9A. This adjusted final location of the distal point 212 can then be used to calculate the distal resection depth [block 267]. The distal resection depth may be used to generate resection data, which may be employed by the surgical system 100 as a haptic boundary for controlling the haptic device 60 or surgical robot. Additionally or alternatively, the resection data may be utilized by a surgical robot during the arthroplasty procedure. Additionally or alternatively, the resection data may be utilized by a navigation system during the arthroplasty procedure. The navigation system may operate in conjunction with an autonomous robot or a surgeon-assisted device in performing the arthroplasty procedure. An autonomous robot, such as a cutting device with at least two degrees of freedom (e.g., rotating burr and translation capabilities) may perform the arthroplasty procedure with the resection data utilized as a tool path for performing a resection. A surgeon-assisted device, such as the haptic device 60 described herein or a cutting tool with at least one degree of freedom (e.g., rotating burr moved or translated by a surgeon), may perform the arthroplasty procedure with the resection data being a virtual or haptic boundary for controlling or limiting certain movements of the cutting tool (e.g., depth of resection). Thus, the methods described herein for determining the location of the most distal point may describe a method of generating resection plane data for use in planning an arthroplasty procedure on a patient bone.

Figure 9C:
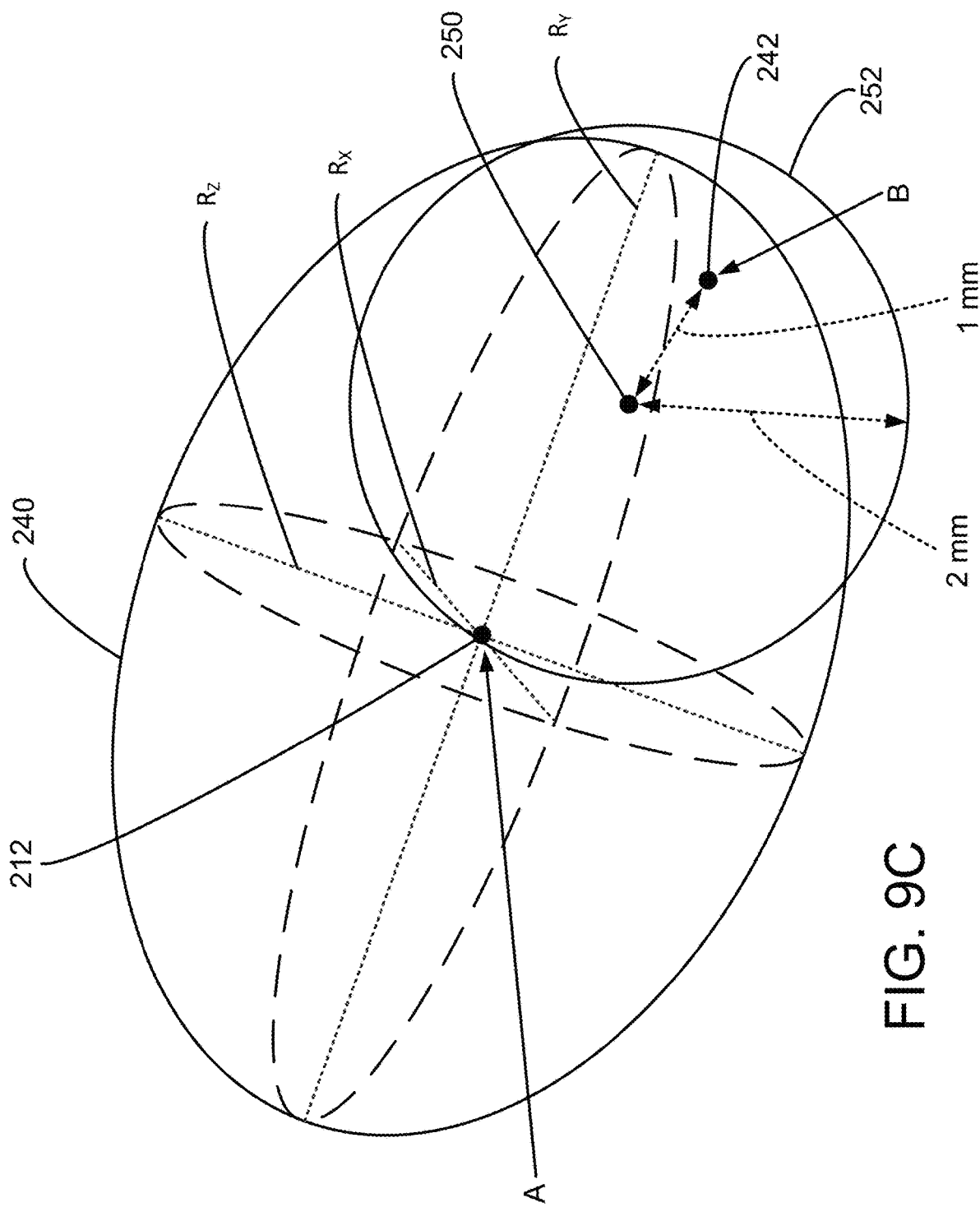
FIG. 9C is the same ellipsoid of FIGS. 9A and 9B plus a sphere employed in the process of fine-tuning the placement of the mapped distal points.
Figure 10B:
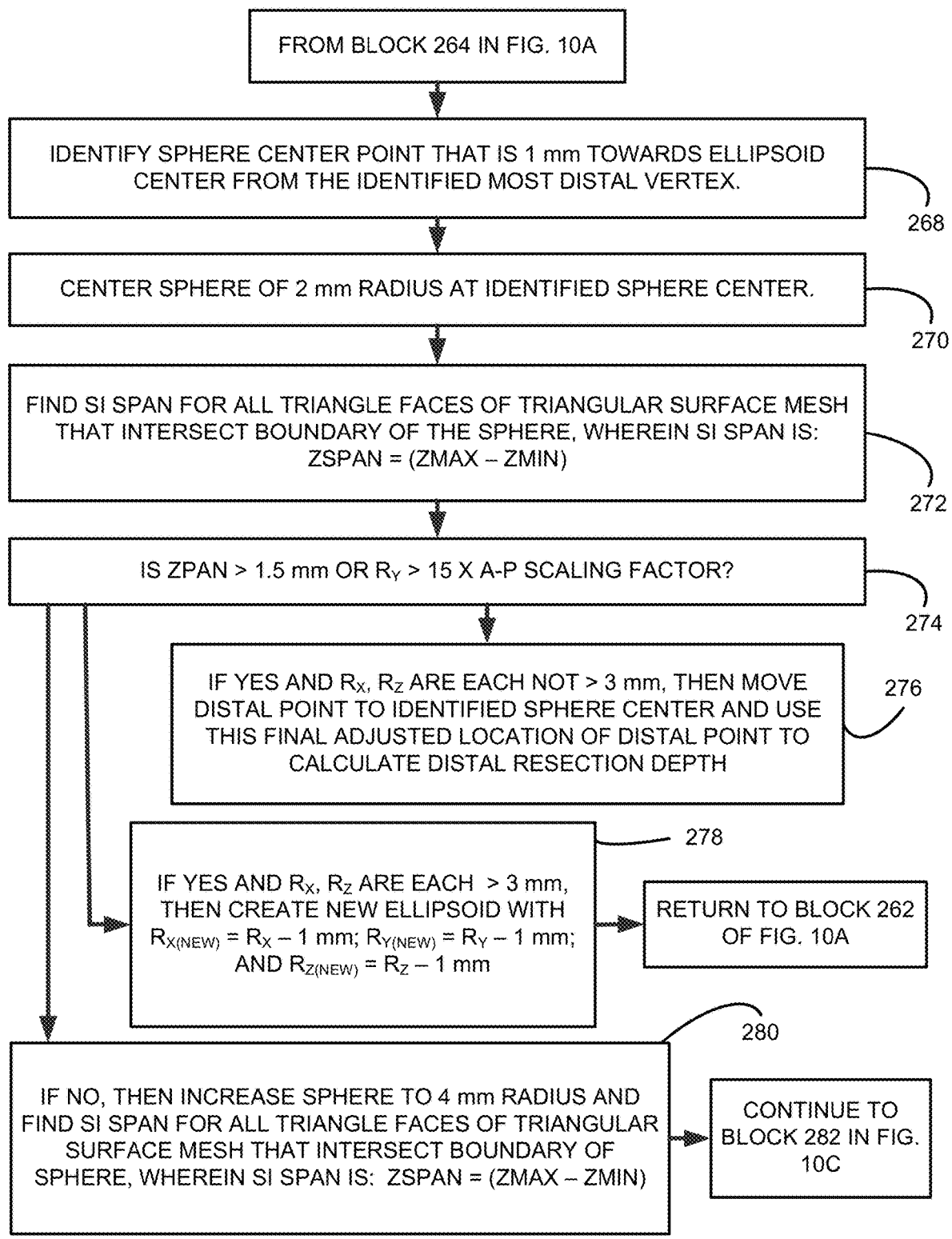
Figure 10C:
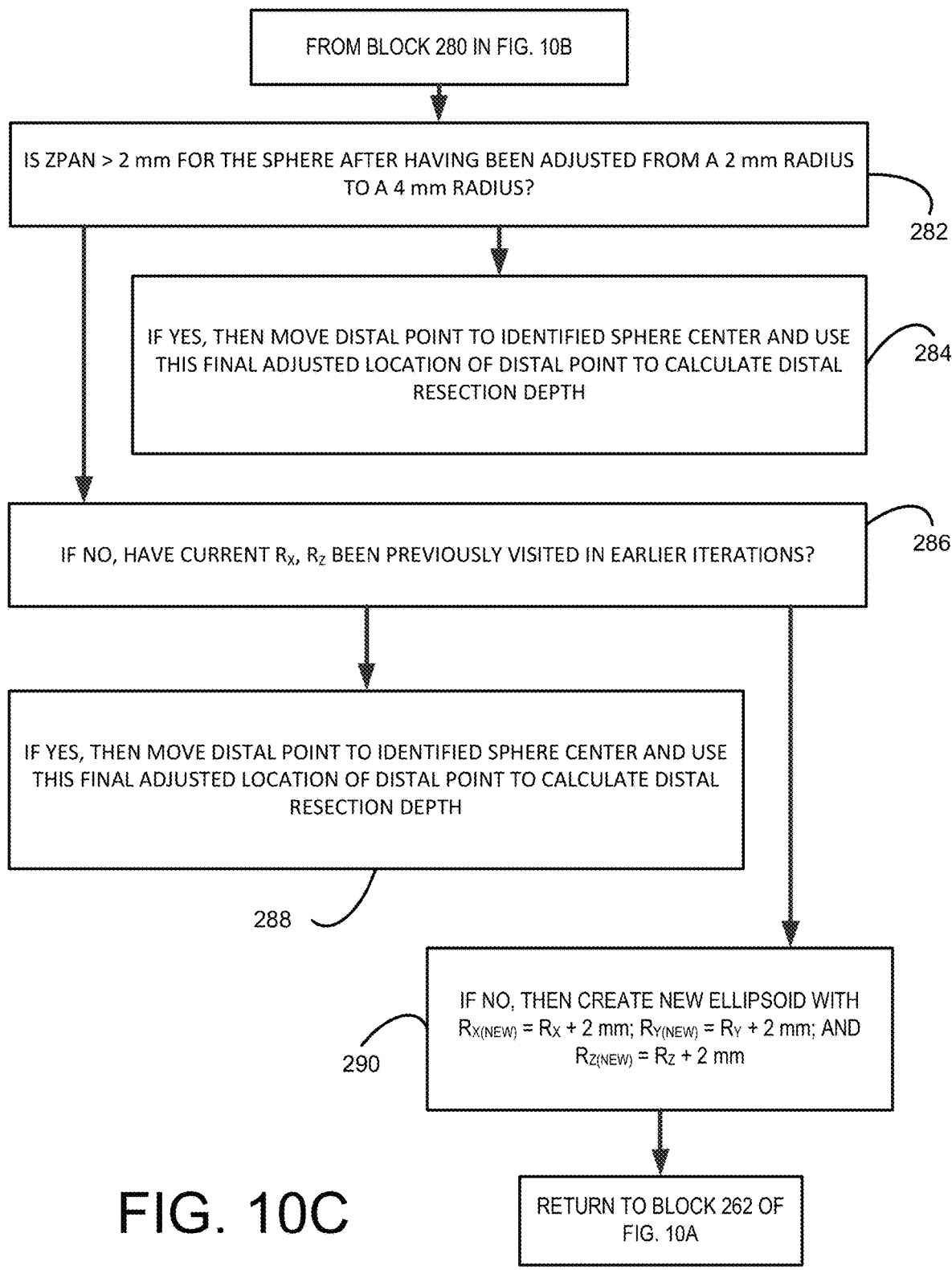

If on the other hand, as can be understood from FIGS. 10A, 10B and 9C, which is the same ellipsoid 240 of FIGS. 9A and 9B, the identified most distal vertex 242 (indicated by arrow B in FIGS. 9A and 9C) is too close to the boundary of the ellipsoid 240, then, as indicated in FIG. 9C, a sphere center point 250 is identified that is one millimeter towards the ellipsoid center (i.e., the initial most distal point 212 indicated by arrow A in FIGS. 9A and 9C) from the identified most distal vertex 242 indicated by arrow B [block 268]. As illustrated in FIG. 9C, the sphere 252 is centered at the sphere center point 250 and has a radius of 2 millimeters [block 270]. A superior-inferior or SI span is found for all triangle faces 232 of the triangular surface mesh 228 that intersect the boundary of the sphere 252, wherein the SI span is: Zspan=(Zmax−Zmin) [block 272]. It is noted that the Zspan is the span height in the Z direction (proximal-distal) from highest point to lowest point.

Describing the SI Span another way, for all triangle faces 232 contained inside the sphere 252, the vertex 242 with the smallest Z value (i.e., lowest height) is subtracted from the vertex 242 with the largest Z value (i.e., highest height). Thus, the SI span measures the difference between the maximum point of intersection of the triangular faces 232 with the sphere 252 and the minimum point of intersection of the triangular faces 232 with the sphere 252, along one coordinate direction (e.g., z). From this, it can be determined that a change or difference between the minimum and maximum along a particular coordinate direction can predict the presence of an osteophyte, which protrudes, often abruptly, from a boney surface.

A check is made to see if the Zspan is greater than 1.5 millimeters or the semi-major axis $R_Y$ of the current iteration of the ellipsoid 240 is greater than 15 times the A-P scaling factor [block 274]. If either of the conditions of [block 274] are satisfied and each of the semi-minor axes $R_X$, $R_Z$ of the current iteration of the ellipsoid 240 are each not greater than three millimeters, then the distal point 212 is moved to the identified sphere center point 250 and this final adjusted location of the distal point 212 is used to calculate the distal resection depth [block 276]. In this way, the Zspan is used to identify a peak (e.g., osteophyte) in the Z direction. And if the system detects a peak (i.e., Zspan>1.5 mm), then the system will adjust the search in an attempt to find the highest elevation outside the peak.

Alternatively, if either of the conditions of [block 274] are satisfied, but the semi-minor axes $R_X$, $R_Z$ of the current iteration of the ellipsoid 240 are each greater than three millimeters, then a new ellipsoid is created to have: a semi-minor axis $R_{X(NEW)}$ that is one millimeter less than the semi-minor axis $R_X$ of the immediately preceding ellipsoid in the iteration (i.e., $R_{X(NEW)}=R_X-1$ mm); a semi-minor axis $R_{Z(NEW)}$ that is one millimeter less than the semi-minor axis $R_Z$ of the immediately preceding ellipsoid in the iteration (i.e., $R_{Z(NEW)}=R_Z-1$ mm); and a semi-major axis $R_{Y(NEW)}$ that is one millimeter less than the semi-major axis $R_Y$ of the immediately preceding ellipsoid in the iteration (i.e., $R_{Y(NEW)}=R_Y-1$ mm), and the process returns to [block 262] of FIG. 10A to perform another iteration with the new ellipsoid [block 278].

Finally, if neither of the conditions of [block 274] are not satisfied, then the radius of the sphere 252 is increased to 4 millimeters and a SI span is found for all triangles faces 232 of the triangular surface mesh 228 that intersect the boundary of the sphere 252, wherein the SI span is: Zspan= (Zmax−Zmin), and the process continues at [block 282] in FIG. 10C [block 280]. A check is made to see if the Zspan associated with the new 4 mm radius sphere 252 is greater than 2 millimeters [block 282]. If the condition of [block 282] is satisfied, then the distal point 212 is moved to the identified sphere center point 250 and this final adjusted location of the distal point 212 is used to calculate the distal resection depth [block 284].

While a sphere 252 is described in the present disclosure, it is foreseen that other three-dimensional shapes may be employed instead of a sphere. For example, an ellipsoid, prism, or box, among other three-dimensional shapes may be used without limitation and without departing from the scope of the present disclosure. Additionally or alternatively, a two-dimensional shape such as a plane or a surface without a thickness may be used herein.

If the condition of [block 282] is not satisfied, then a check is made to see if the values for the current semi-minor axes $R_X$, $R_Z$ have been previously visited in earlier iterations [block 286]. If the values for the current semi-minor axes $R_X$, $R_Z$ were previously visited, then the distal point 212 is moved to the identified sphere center point 250 and this final adjusted location of the distal point 212 is used to calculate the distal resection depth [block 288].

If on the other hand, the values for the current semi-minor axes $R_X$, $R_Z$ were not previously visited, then a new ellipsoid is created to have: a semi-minor axis $R_{X(NEW)}$ that is two millimeters greater than the semi-minor axis $R_X$ of the immediately preceding ellipsoid in the iteration (i.e., $R_{X(NEW)}=R_X+2$ mm); a semi-minor axis $R_{Z(NEW)}$ that is two millimeters greater than the semi-minor axis $R_Z$ of the immediately preceding ellipsoid in the iteration (i.e., $R_{Z(NEW)}=R_Z+2$ mm); and a semi-major axis $R_{Y(NEW)}$ that is two millimeters greater than the semi-major axis $R_Y$ of the immediately preceding ellipsoid in the iteration (i.e., $R_{Y(NEW)}=R_Y+2$ mm), and the process returns to [block 262] of FIG. 10A to perform another iteration with the new ellipsoid [block 290].

The process previously described may be useful in detecting whether an osteophyte or other irregular boney feature is encountered when determining the identified most distal vertex 242 (indicated by arrow B in FIG. 9A). Because an osteophyte may protrude from the surface of the patient femur model 226, the most distal vertex 242 may lie on the osteophyte. But, for the purposes of mapping a distal point 212 from the generic femur model 202 onto the patient femur model 226, it may be beneficial to disregard the presence of the osteophyte on the patient femur model 226 because the osteophyte surface may be irrelevant in determining a resection depth. That is, since resection depth is a function of the most distal vertex 242, the most distal vertex 242 should not be altered by the presence of an irregular boney feature. Thus, the process described previously may be summarized as follows.

The initial location of a distal point 212 is mapped from the generic femur model 202 onto the patient femur model 226, which is indicated at the location called out by Arrow A in FIG. 9A. An ellipsoid 240 is created based on the parameters previously described. A most distal vertex 242 is identified within the ellipsoid 240 based on the parameters previously described. If the most distal vertex 242 is not too close to the edge of the boundary of the ellipsoid 240, then the most distal vertex 242 is used to calculate distal resection depth, as discussed with reference to [Block 267]. If the most distal vertex 242 is too close to the edge of the boundary of the ellipsoid 240, it must be determined if the most distal vertex 242 lies on an osteophyte via, in certain embodiments, the Zspan calculation described previously. If the most distal vertex 242 lies on an osteophyte, the size of the ellipsoid is reduced and the process continues as previously described. Finally, if the most distal vertex 242 does not lie on an osteophyte, the size of the ellipsoid is increased and the process continues as previously described. The process of increasing or decreasing the size of the ellipse can occur multiple times. For example, if the most distal point is near the edge of the ellipse and it is determined to not be located on an osteophyte, then the ellipse could continue to increase in size until it either encounters an osteophyte or is determined to be near the edge.

The patient femur model 226 and the points 212, 214, 218, 220 thereon may be depicted on the display 54 as a three dimensional computer model capable of being rotated and moved. Additionally or alternatively, the patient femur model 226 and the points 212, 214, 218, 220 thereon may be depicted on the display 54 in three different views, namely, a coronal view, an axial or transverse view, and a sagittal view as respectively illustrated in FIGS. 6A-6C. Where one or more of the points 212, 214, 218, 220 is hidden by bone structure of the model 226, for example, as is the case with points 214, 220 in FIG. 6A and point 218 in FIG. 6C, the hidden points may be depicted translucent or in another depiction that indicates the points are present, but located behind some bone structure in the view. In certain embodiments, the patient femur model 226 may be depicted transparently so that the points 212, 214, 218, 220 are visible even if occluded by the surfaces of the patient femur model 226. Where the one or more of the points 212, 214, 218, 220 are fully visible in a view (in other words, not hidden by bone structure of the model 226), as is in the case with points 212, 218 in FIG. 6A, points 212, 214, 218, 220 in FIG. 6B and points 212, 214, 220 in FIG. 6C, the visible points 204, 208 may be depicted as solid fully visible points to indicate the points are not hidden by bone structure of the model 226 but are fully visible in the view.

These points 212, 214, 218, 220, when properly positioned on the femur model 226, can serve as bone resection depth points to be used to calculate the depth of bone resections to the patient femur that will allow a selected femur implant (in conjunction with a selected tibial implant) to achieve a desired surgical outcome when the actual implants are implanted onto the patient's tibia and femur as part of the arthroplasty procedure preoperatively planned as described herein.

Once the most posterior points 214, 220 and the most distal points 212, 218 have been properly located on the patient femur model 226 as described above, these points 212, 214, 218, 220 can be used with a three dimensional computer model of a candidate femur implant 320, or data associated with such an implant 320, to preoperatively calculate the associated bone resections that need to be made in the actual patient bone to receive the actual femur implant to achieve a desired surgical outcome from implanting the actual femur implant onto the actual patient bone during the actual arthroplasty procedure.

Figure 13:
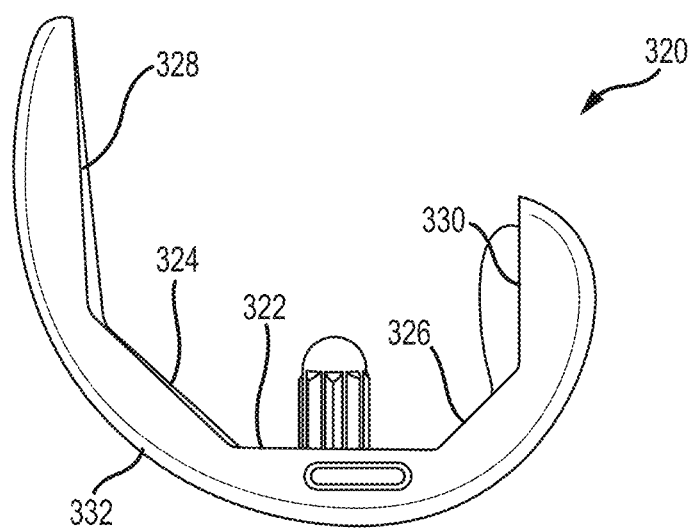
FIG. 13 is a sagittal view of a three dimensional computer model of the candidate femur implant (i.e., the femur implant model) illustrating its distal bone resection contacting surface along with the adjacent anterior chamfer resection contacting surface, posterior chamfer resection contacting surface, anterior resection contacting surface, and posterior resection contacting surface, these resection contacting surfaces being proximal the medial and lateral condylar surfaces of the of the femur implant model.

FIG. 13 is a sagittal view of a three dimensional computer model of the candidate femur implant (i.e., the femur implant model 320) illustrating its distal bone resection contacting surface 322 along with the adjacent anterior chamfer resection contacting surface 324, posterior chamfer resection contacting surface 326, anterior resection contacting surface 328, and posterior resection contacting surface 330, these resection contacting surfaces being proximal the medial and lateral condylar surfaces of the 332 of the femur implant model 320.

Figure 14C:
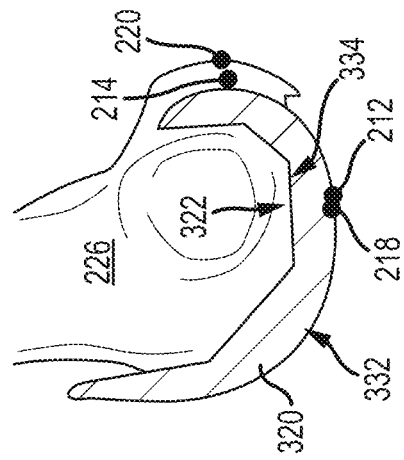
FIGS. 14A-14C respectively illustrate coronal, axial or transverse, and sagittal views of the femur implant model superimposed on the distal end of the three dimensional computer model of the patient femur (i.e., the patient femur model).
Figure 14B:
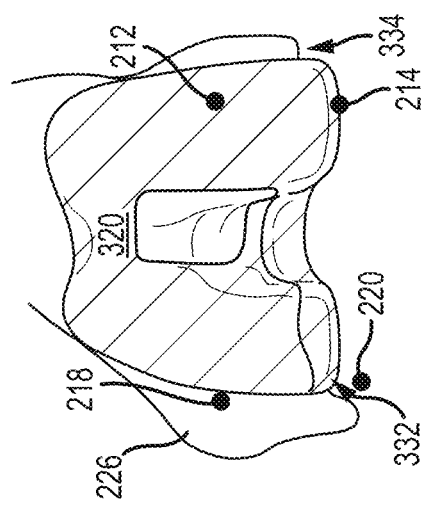
Figure 14A:
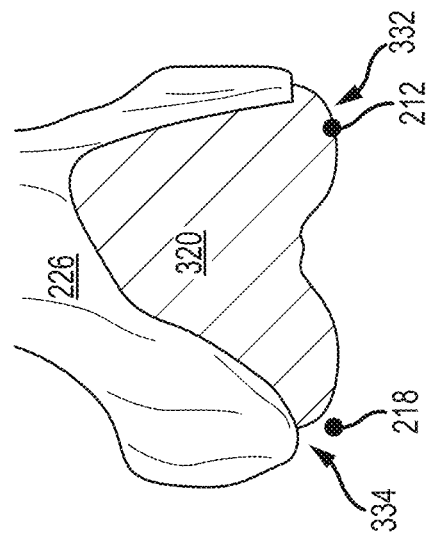

As can be understood from FIGS. 14A-14C, which respectively illustrate coronal, axial or transverse, and sagittal views of the femur implant model 320 superimposed on the distal end of the three dimensional computer model of the patient femur (i.e., the patient femur model 226), one, two, three or four of the points 212, 214, 218, 220 may be aligned with a similar or equivalent most proximal and most distal femur condyle points or regions on the articular surface 332 of the femur implant model 320, thereby defining a proposed distal femur resection 334 that extends along the distal bone resection contacting surface 322 of the implant model 300. In some embodiments, the defined proposed resection may also include proposed bone resections corresponding to the various other bone resection contacting surfaces 324, 326, 328, 330 of the candidate femur implant model 320, as can be understood from a comparison of FIGS. 13 and 14C.

The defined proposed distal femur resection 334 is defined according to resection depth and planar orientation. Of course, the defined proposed distal femur resection 334 can be adjusted or modified by preoperative, and/or in some embodiments, intraoperative, surgeon input by changing the resection depth distally or proximally relative to the points 212, 214, 218, 220, changing the size of the candidate femur implant model 320 to a smaller or larger size, changing the planar orientation of the proposed distal resection 334 to account for a desired varus-valgus, internal-external, or extension-flexion rotation, to cause all four points 212, 214, 218, 220 or only a single pair of points to correspond to similar points on the lateral and medial articular surfaces 332 of the femur implant model 320, depending on whether or not an anatomic (natural) alignment is sought or a more traditional mechanical axis alignment is sought.

Figure 16C:
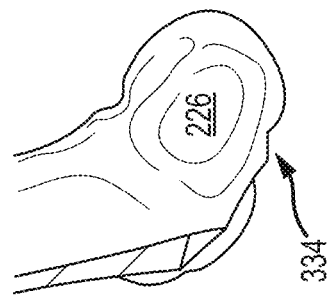
FIGS. 16A-16C are various views of the femur model as proposed to be resected and illustrating the proposed femur resections, including the distal resection.
Figure 16B:
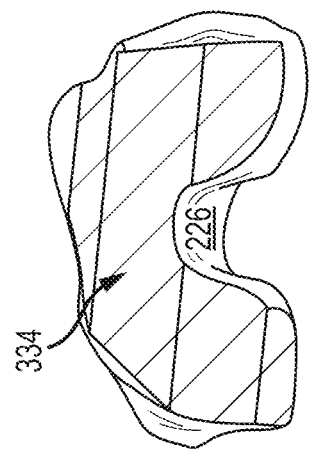
Figure 16A:
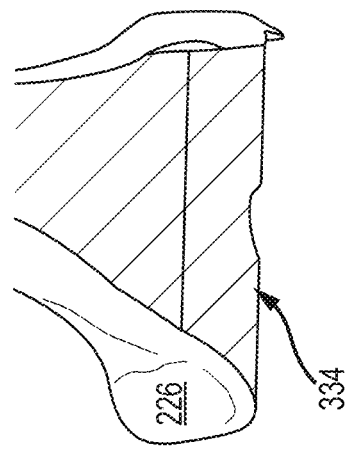

FIGS. 14A-14C are illustrative of a situation where just a pair of points 212, 214 is aligned with a similar pair of points or regions on one of the articular surfaces 332 of the femur implant model 320. For example, as can be seen in FIGS. 12A-12C, the lateral points 212, 214 are aligned with similar points or regions on the articular surface 334 of the femur implant model 320, but the medial points 218, 220 are not aligned with their similar medial points or regions on the articular surface 332 of the implant model 320. With only the these pairs of points matching, which happens to be on the lateral side, the orientation of the distal bone resection contacting surface 322 of the implant model 320, and as a result, the orientation of the proposed resection plane 334, is then determined by maintaining the matching of the lateral points while achieving a desired angle of the proposed distal resection plane 334 relative to an axis of the patient's leg, femur or tibia, such as, for example, the femoral mechanical axis or leg mechanical axis. Once the surgeon has approved the depth and orientation of the proposed femur resection plane 334, the associated data can be provided to the surgical system 100 for use by the navigation system in guiding the haptic device 60 during the surgery, and the resected patient femur model 226 may be represented to the surgeon intraoperatively as indicated in FIGS. 16A-16C, which are various views of the femur model 226 as proposed to be resected and illustrating the proposed femur resections, including the distal resection 334.

While the preceding discussion of defining the proposed femur resection plane 334 has been made in the context of superimposing a candidate femur implant 320 on the femur model 226 and showing such superimposing visually on the computer display 54 of the system 100, in other embodiments, such a process can take place by data representative of the candidate femur implant 320, not requiring a three dimensional representation of the candidate femur implant or its actual visual representation on the computer display 54.

3. Adjusting Proposed Resection Depths for Joint Gap

Figure 17:
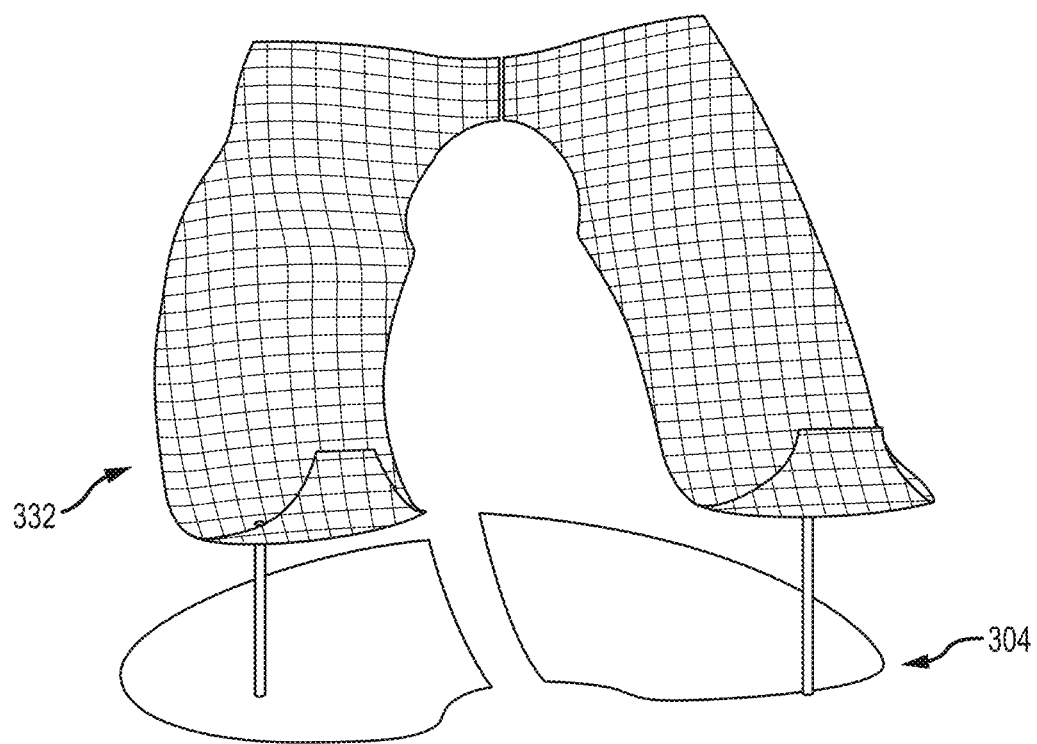
FIG. 17 is an isometric view of the femoral articular surface of the femur implant model and the tibial articular surface of the tibial implant model.

To account for proper joint gap spacing between the preoperatively planned implant models 224, 226 that will result in a desired surgical outcome when the actual implants are implanted during the arthroplasty on the patient, the bone resections being made via the surgical system 100 according to the preoperative planning outlined above in Subsections I(A)(1) and I(A)(2) of this Detailed Description, two gap distances are calculated as part of the preoperative planning of the resection depths. The two calculated gap distances are the minimum signed distance between: the medial condyle surface 332 of the femur implant model 320 and the medial articular surface 304 of the tibial implant model 300; and the lateral condyle surface 332 of the femur implant model 320 and the lateral articular surface 304 of the tibial implant model 300. FIG. 17 is an isometric view of the femoral articular surface 332 of the femur implant model 320 and the tibial articular surface 304 of the tibial implant model 300. While the disclosure focuses on the bones forming the knee joint, the teachings herein are equally application to bones forming other joints as well such as, for example, an ankle, elbow, or wrist.

The minimum gap distance is defined as positive for all points on the femoral condyle implant that are located inside a positive Voronoi region defined by the faces, internal edges, and internal vertices of the articular surface 304 of the tibial implant model 300. The minimum gap distance is defined as negative for all points on the articular surface 332 of the femoral implant model 320 that are located inside a negative Voronoi region. Only the distance between the articular surfaces of the models need to be considered, as these are the surfaces on which the implants contact each other.

To achieve an acceptable level of accuracy, the gap distance is computed between the vertices of the triangular faces of the triangular surface mesh of the articular surface model 332 of the femur implant model 320 and the triangle faces of the triangular surface mesh of the articular surface model 304 of the tibial implant model 300, as shown in FIG. 17. Due to the fine resolution of the femoral articular surface model 320, the vertex to surface gap distance is a close approximation to the true surface to surface gap distance.

The system 100 may employ two different algorithms for calculating the joint gap, the first being a global search closest distance algorithm ("GSCDA"), and the second being an incremental search closest distance algorithm ("ISCDA"). The GSCDA is guaranteed to find the minimum signed distance between arbitrary surfaces. The ISCDA is a quick incremental local search algorithm that works for convex surfaces.

In the application, the gap distance for a first joint pose is calculated with the GSCDA. It returns the gap distance and the index of the vertex of the surface mesh of the articular surface model 332 of the femur implant model 320 that has the closest gap distance.

In the application, the gap distance for a second joint pose is calculated with the ISCDA. In doing so, it references the vertex returned from the first joint pose calculation. All the gap distance calculations of the remaining joint poses that follow occur in the same way; i.e., each uses the ISCDA and references the vertex from the previous joint pose calculation.

Using the GSCDA algorithm for a single pose and then the ISCDA for the remaining poses speeds up the gap calculation. Utilizing GSCDA for each pose would require additional time and computing resources, especially with many poses to analyze.

In certain instances, a tibial surface profile may be utilized that is different than the anatomical or true tibial articular surface. If, for example, the tibial articular surface is nearly as conforming as the femoral articular surface, a modified tibial articular surface that is flattened somewhat may be used in the joint gap calculation. In certain instances where the tibial surface profile is very conforming to the femoral articular surface, then slight anterior-posterior and/or medial-lateral translation may result in a virtual interference condition, which makes the computed signed distance show "tight" or negative. Thus, pose positions may indicate an interference position if the tibia is slightly translated anterior-posterior and/or medial-lateral, where there is actually no interference condition. Such a measurement of perceived interference may indicate to the surgeon that the femoral and tibial components of an implant system should be positioned further away from each other to eliminate the perceived interference condition. In order to counter the perceived interference, the signed distance may be computed between the femoral articular surface and a generalized tibial surface that is somewhat flat or slightly concave (i.e., more flat than the true tibia).

i. Global Search Closest Distance Algorithm ("GSCDA")

Figure 18:
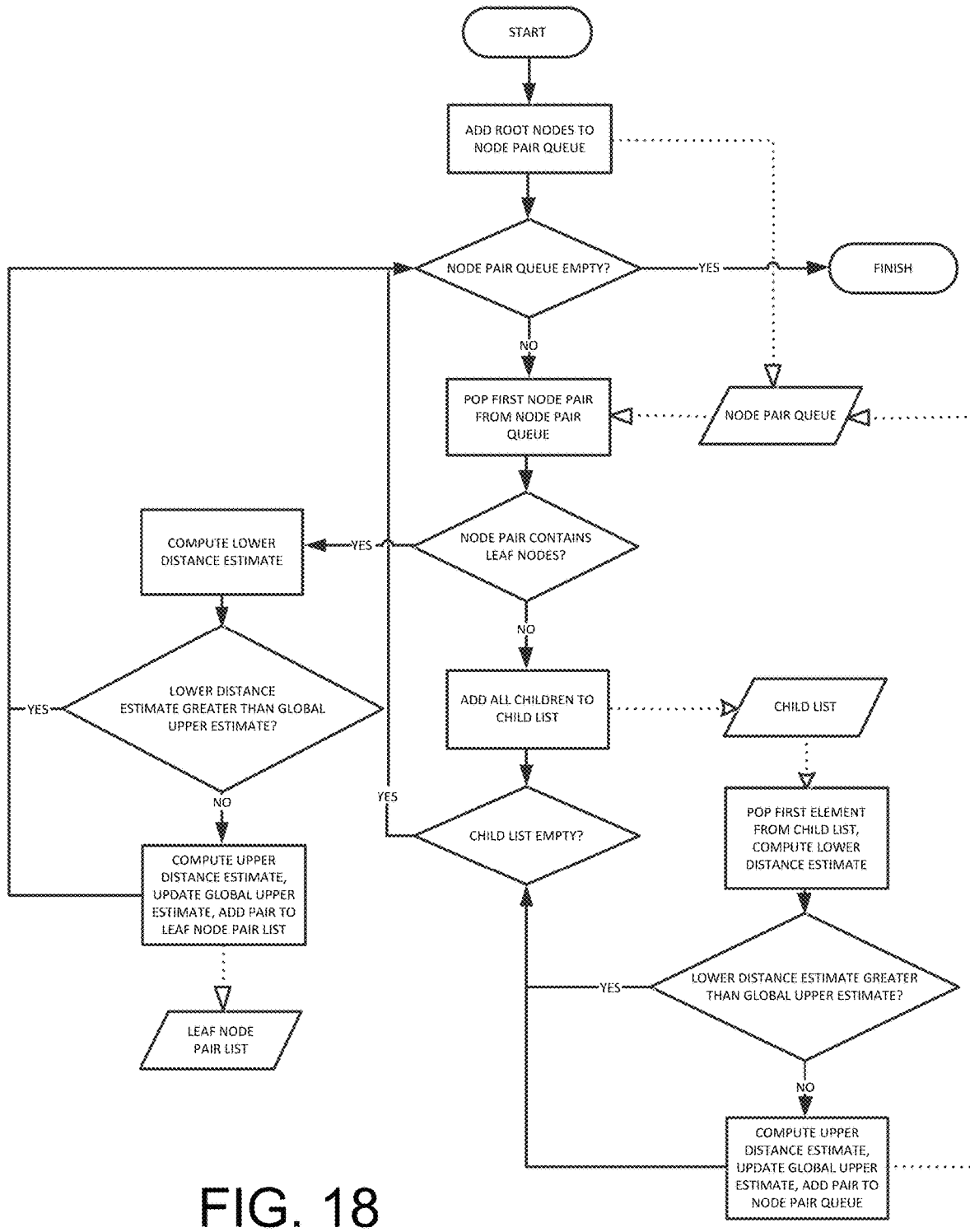
FIGS. 18 and 19 are, respectively, algorithm flow charts of a broad-phase search stage and a narrow-phase search stage of a global search closest distance algorithm.
Figure 19:
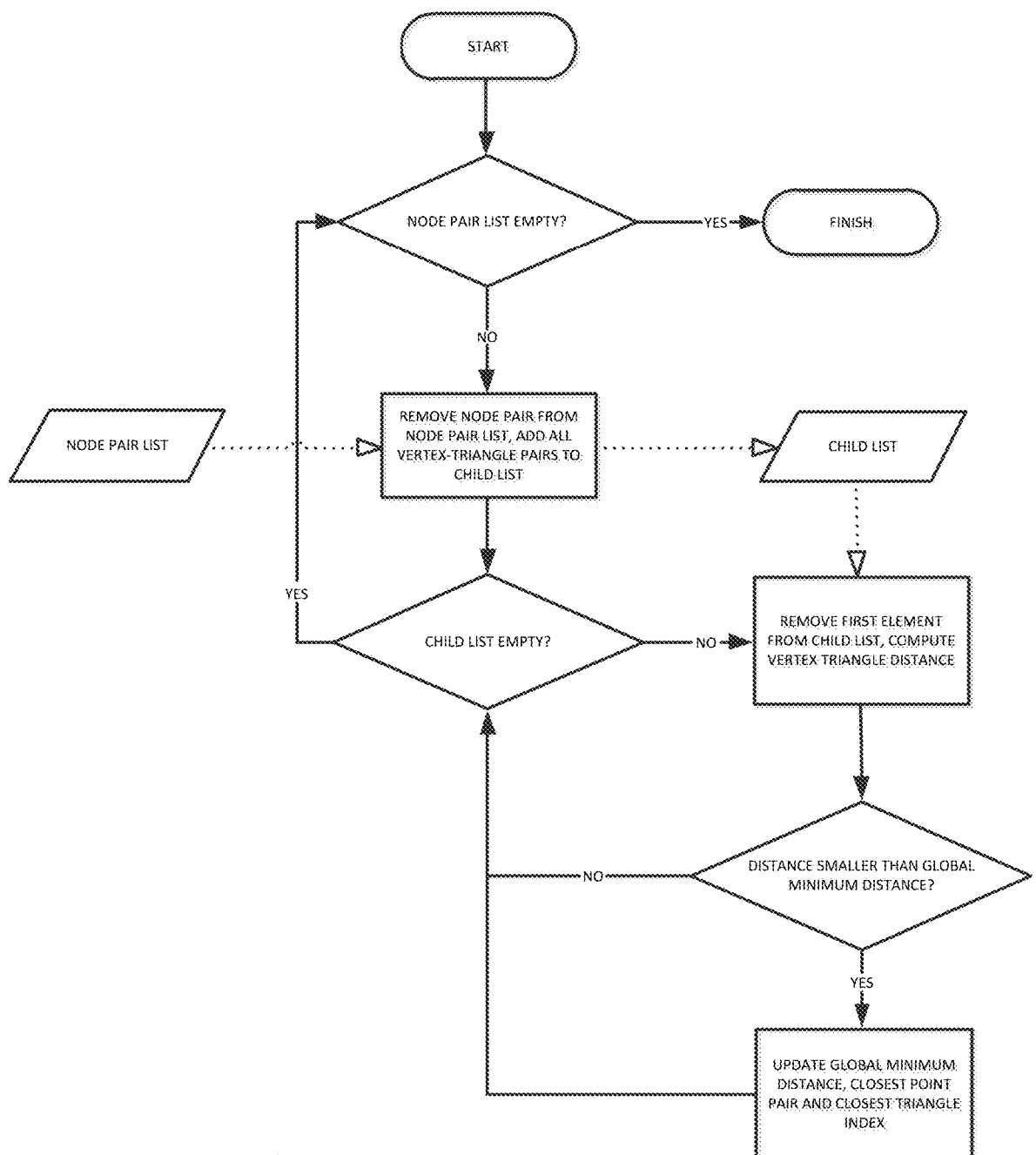

The GSCDA can be divided into a broad-phase search stage of FIG. 18 and a narrow-phase search stage of FIG. 19.

A hierarchical sphere tree is created for each articular surface model. The tree is constructed in a bottom up fashion, so each leaf node sphere encloses a single triangle face and each parent node sphere encloses its child node spheres. During the broad-phase search stage of FIG. 18, the GSCDA traverses both sphere trees in a breadth-first manner while maintaining a queue of candidate node pairs for the narrow-phase search stage, which may be similar to the algorithm described in A Framework for Efficient Minimum Distance Computations by David E. Johnson and Elaine Cohen, Department of Computer Science, University of Utah (1998), which is hereby incorporated by reference herein in its entirety. Each node pair produces lower and upper bound estimates for the gap distance between the models 304, 332. A global upper bound estimate is maintained to prune candidate node pairs. If a new non-leaf node pair yields a lower bound estimate that is greater than the global upper bound estimate, the pair is discarded during the search. Leaf node pairs are inserted into a leaf node pair list. If a node pair is not discarded, its upper bound estimate is used to update the global upper bound estimate. The broad-phase search is terminated when there are no more node pairs in the queue.

As reflected in FIG. 19, the narrow-phase search stage traverses the list of leaf node pairs and computes the gap distance between the vertices referenced in the femoral condyle component leaf nodes and the triangle faces referenced in the tibial component leaf nodes. The vertex-triangle pair with the smallest gap distance is selected as the solution. The gap distance, the triangle index, as well as the closest point pair is returned by the algorithm.

The narrow-phase search uses the point-triangle distance calculation method described in Section 5.1 of *Real-Time Collision Detection* by Christer Ericson (2005), which is hereby incorporated by reference herein in its entirety. To account for negative gap distances, the algorithm is modified such that when the closest point is on a triangle face and not on a triangle edge or vertex, the sign of the distance is determined from the sign of the inner product of the triangle normal and the difference vector between the point and the closest point on the triangle.

This modified algorithm does not handle the case when the point is located in the negative Voronoi cells of the internal edges and vertices of the tibial component model because it returns a positive distance when the closest point is located on any edge or vertex of the model. Due to the high resolution of the femoral condyle component model, the modified algorithm yields a reasonable approximation to the distance between the models, because when the closest point is located on an internal edge or vertex of the tibial component model, there will be a nearby vertex of the femoral condyle model for which the closest point is located on a triangle face of the tibial component model. Closely approximating the gap distance by computing the distance between the vertices of the femoral condyle articular surfaces to the triangle faces of the tibial articular surface yields is performed quicker than calculating from vertices of the femoral condyle articular surface to vertices of the tibial articular surface. A vertices-to-vertices calculation may yield marginal improvements in accuracy, but will require more computing time and, thus, be slower.

ii. Incremental Search Closest Distance Algorithm ("ISCDA")

The ISCDA starts with a known vertex of the triangular faces of the triangular surface mesh of the articular surface model 332 of the femur implant model 320 and finds the locally closest vertex by searching all neighbor vertices of the current vertex. The search terminates when all adjacent vertices (first and second level) of the current vertex are further away from the triangle faces of the triangular surface mesh of the articular surface model 304 of the tibial implant model 300 than the current vertex. The gap distance is computed by traversing the sphere tree data structure of the tibial implant model in a depth-first manner using the position of the vertex as the input position.

Once the joint gap distance is determined according to the proper application of the above-discussed GSCDA and ISCDA, the joint gap values can be applied to adjust, if necessary, the proposed femur and tibia resection planes with respect to resection depth.

iii. Pose Capture and Intra-Operative Joint Gap Calculation

Once the patient femur 11 and tibia 10 are tracked by the tracking and navigation system, the surgeon may intraoperatively capture or record the pose (i.e., position and orientation) of the tibia 10 relative to the femur 10 with the surgical system 100. More particularly, the surgeon may position the patient's femur 11 and tibia 10 in a set of poses with different flexion angle values and capture or otherwise record the measured position and orientation of the tibia 10 relative to the femur 11 for each pose. As discussed previously, the three-dimensional femur model with the femur implant model and the three-dimensional tibia model with the tibial implant model may be depicted on the display screen, and the location and orientation of the models may correspond with the physical location and orientation of the tibia 10 and femur 11.

The surgeon may then run the joint gap calculation using the GSCDA for one of the poses. The calculation may be ran on the extension pose (i.e., flexion angle about zero degrees), or a flexion pose (i.e., flexion angle greater than zero degrees). Then, the ISCDA calculation may be executed for the rest of the poses. In certain embodiments, the surgeon may run the joint calculation using the GSCDA for all of the poses.

As an example, a surgeon may capture five poses corresponding to 0 degrees flexion, 30 degrees flexion, 60 degrees flexion, 90 degrees flexion, and 120 degrees flexion. The GSCDA calculation is executed for one of the poses, such as the 60 degree flexion pose. Next, the ISCDA calculation may be executed on the next-closest pose. In this example, the calculations of ISCDA may be performed in the following order: 90 degrees, 120 degrees, then 30 degrees, and 0 degrees. At the beginning of each ISCDA sequence, the vertex index from the GSCDA calculation is used for initialization of the search (i.e., at 90 degrees and 30 degrees). In the subsequent steps, the vertex index from the ISCDA calculation is used from the previous step (i.e., at 120 degrees the vertex index from 90 degrees, and at 0 degrees the vertex index from 30 degrees).

As another example, a method of generating resection data for use in planning an arthroplasty procedure on a knee joint may include the following steps. A computer may receive a three-dimensional femur model and a three-dimensional femur implant model oriented relative to each other in a first pre-planned orientation in a common three-dimensional coordinate system. The three-dimensional femur model may correspond to the femur of the patient. The three-dimensional femur implant model may include a medial condyle surface and a lateral condyle surface. The computer may also receive a three-dimensional tibia model and a three-dimensional tibia implant model oriented relative to each other in a second pre-planned orientation in the common three-dimensional coordinate system. The three-dimensional tibia model may correspond to the tibia of the patient. The three-dimensional tibia implant model may include a medial articular surface and a lateral articular surface. The three-dimensional femur model and the three-dimensional tibia model may be oriented relative to each other according to a pose of the femur and tibia of the patient via a navigation system. The computer may also receive first position and orientation data corresponding to a first position and orientation of the femur and the tibia in a first pose. The computer may also calculate a first signed distance between the medial condyle surface of the three-dimensional femur implant model and a first point on or associated with the three-dimensional tibia implant model in the first pose. The computer may also calculate a second signed distance between the lateral condyle surface of the three-dimensional femur implant model and a second point on or associated with the three-dimensional tibia implant model in the first pose. The computer may determine or adjust a resection depth based on the first and second signed distances. The computer may also generate resection data using the resection depth, the resection data configured to be utilized by the navigation system during the arthroplasty procedure.

B. Avoiding Anterior Shaft Notching

Figure 20:
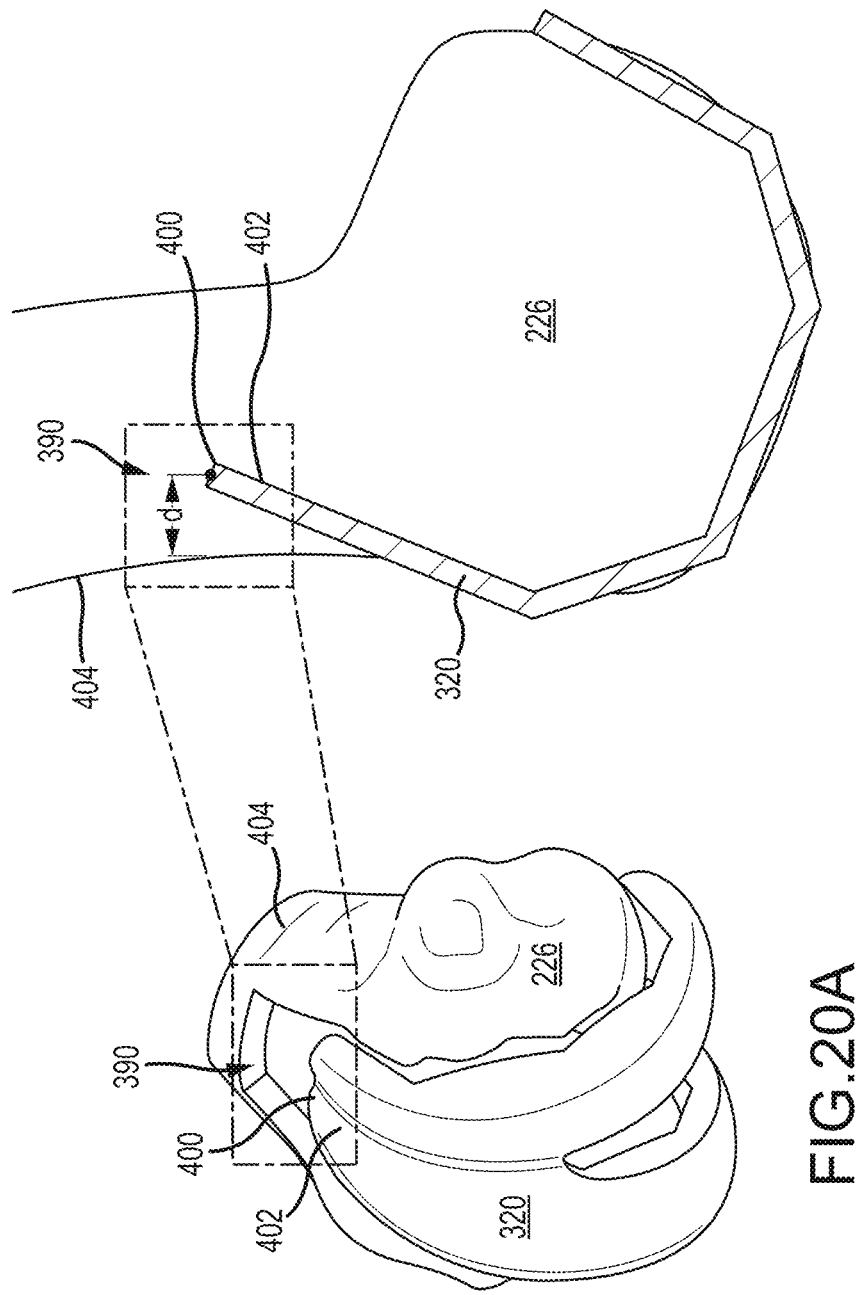
FIGS. 20A and 20B are, respectively, an anterior distal view and a sagittal cross sectional view of the femoral implant model positioned on the patient femur model such that the anterior femoral cortex is notched.

Once the preoperative planning has resulted in proposed bone resections as described above in Subsection A of this Detailed Description, the associated orientation of the candidate femoral implant model can be checked to see if notching of the anterior femoral cortex will occur. In total knee arthroplasty preoperative planning, anterior femoral cortex notching 390 occurs when the femoral implant model 320 is preoperatively planned such that the top edge 400 of the anterior flange 402 sits deep into the anterior femoral cortex 404 of the patient femur model 226. FIGS. 20A and 20B are, respectively, an anterior distal view and a sagittal cross sectional view of the femoral implant model 320 positioned on the patient femur model 226 such that the anterior femoral cortex 404 is notched. Where the actual femoral implant is implanted as indicated in FIGS. 20A and 20B, the indicated notching 390 of the femoral cortex 404 would be an undesirable surgical outcome as the notching creates stress concentrations in the anterior femoral cortex that can lead to fracture of the femoral shaft or supracondylar fractures.

Figure 21:
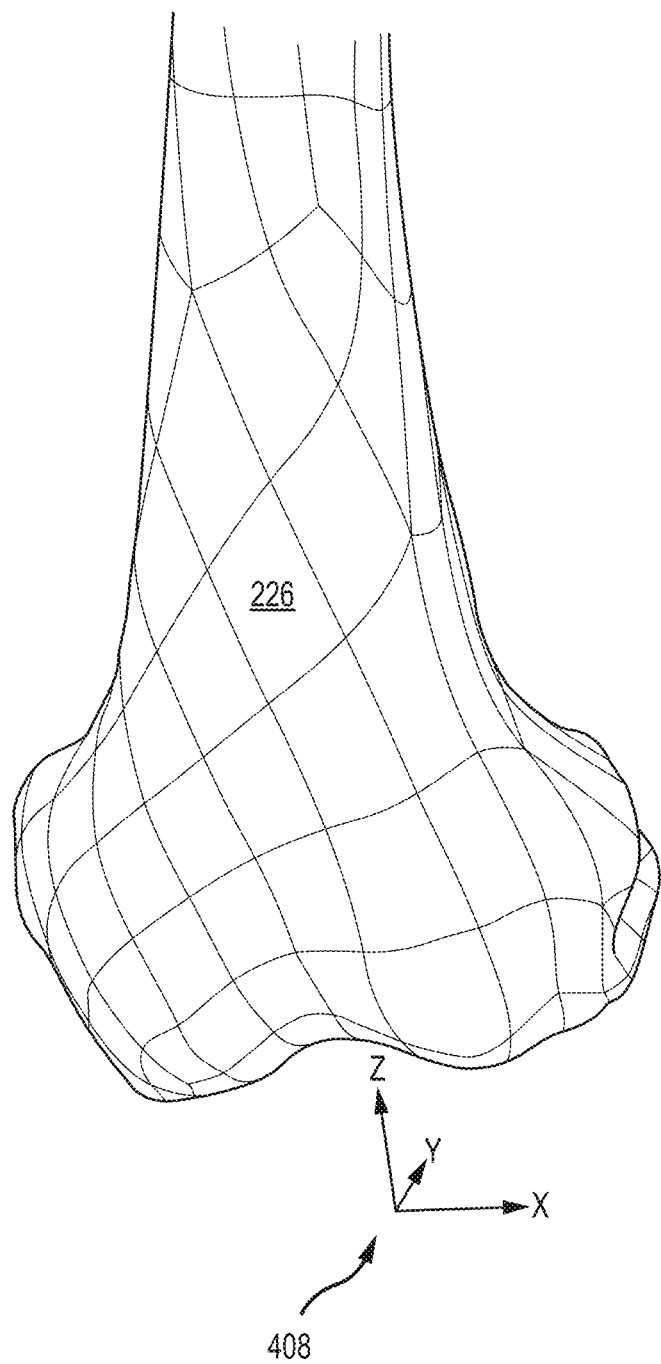
FIG. 21 illustrates a coordinate system established for the patient femur model.

As illustrated in FIG. 21, a coordinate system 408 can be established for the patient femur model 226, wherein the X-axis will be in the medial-lateral direction with the +X-axis pointing towards the lateral femur, the Y-axis will be in the anterior-posterior direction with the +Y-axis pointing towards the posterior femur, and the Z-axis will be in the superior-inferior direction with the +Z direction pointing towards the proximal femur.

Figure 22:
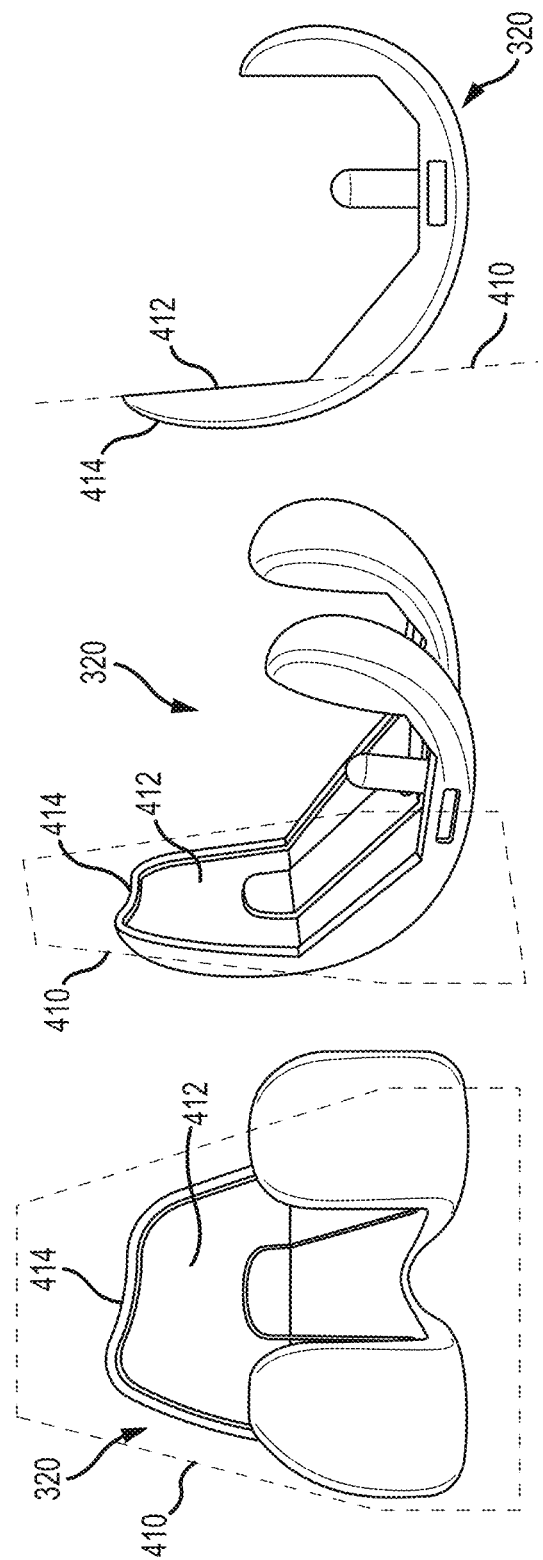
FIGS. 22A-22C are, respectively, posterior, sagittal-posterior, and sagittal views of a candidate femoral implant model with an outline of a haptic plane superimposed on the femoral implant model.

FIGS. 22A-22C are, respectively, posterior, sagittal-posterior, and sagittal views of a candidate femoral implant model 320 with an outline 410 of a haptic object superimposed on the femoral implant model 320. The candidate femoral implant model 320 includes an anterior bone resection contact surface 412 on an anterior flange portion 414 of the femoral implant model 320. The anterior bone resection contact surface 412 of the model 320 and an actual femoral implant are substantially planar and configured to make substantially planar surface contact with an anterior bone resection surface generated in the actual patient bone during the arthroplasty procedure.

As seen in FIGS. 22B and 22C, the haptic object 410 is generally co-planar with the planar contact surface 412 of the anterior flange portion 414 of the femoral implant model 320. Thus, the haptic object 410 is essentially a planar extension of the planar contact surface 412 of the anterior flange portion 414 of the femoral implant model 320.

Figure 23:
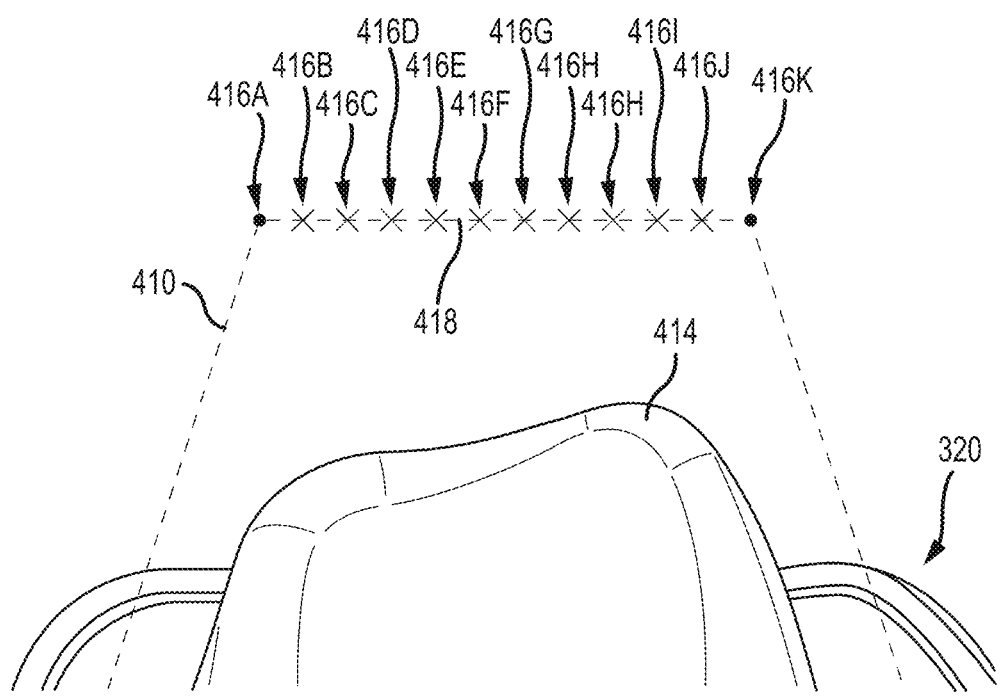
FIG. 23 is an enlarged anterior view of a superior edge of the anterior flange portion of the femoral implant model and a superior boundary of the haptic plane, a series of equally-spaced reference points extending along the superior boundary of the haptic plane.

As illustrated in FIG. 23, which is an enlarged anterior view of a superior edge of the anterior flange portion 414 of the femoral implant model 320 and a superior boundary 418 of the haptic plane 410, a series of equally-spaced reference points 416A-416K extend along the superior boundary 418 of the haptic plane. Reference points 416A and 416K are end points of the series of equally-spaced points 416A-416K. It is noted that the number of points 416 along the superior boundary 418 may be more or less than depicted in FIG. 23. More points 416 may increase the accuracy of the notch assessment, but increasing the points 216 also increases computing time. As discussed below, these reference points are used to evaluate the depth of anterior femoral notch 390 which is measured along the femur anatomical Y direction according to the coordinate system of FIG. 21.

The number of reference points 416A-416K employed in the algorithm depends on the following assumptions in conjunction with the size of the candidate femoral implant model 320. For example, the chance of error in identifying anterior femoral cortex notching increases with a decrease in radius of curvature of the anterior femoral cortex or with a decrease in the number of equally-spaced reference points 416A-416K. Unfortunately, simply increasing the number of equally-spaced reference points 416A-416K to reduce the point-spacing can have an adverse impact on the performance of the algorithm.

Figure 24:
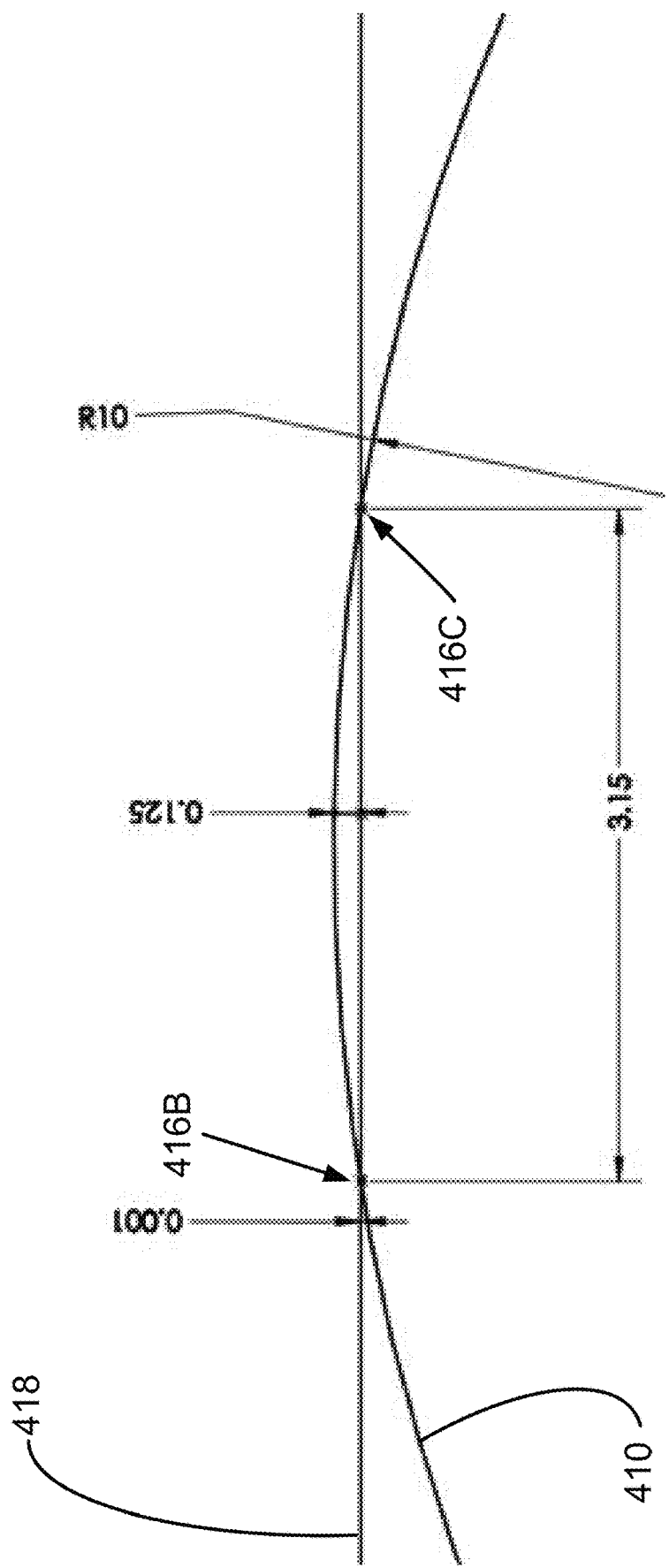
FIG. 24 is a schematic depiction of an anterior femoral cortex notch situation.

The cortex region is convex in nature with a varying radius of curvature moving medial to lateral along the femur. Accordingly, assuming the smallest radius of curvature the algorithm may encounter will be 10 mm, and the minimum clinically relevant notch depth a surgeon may feel is 0.125 mm, these two assumptions yield a minimum point-spacing of 3.15 mm. Thus, as can be understood from FIG. 24, which is a schematic depiction of an anterior femoral cortex notch situation 390 with a radius of 10 mm, the superior edge 418 of the haptic plane 410 with a pair of reference points 416B-416C spaced-apart 3.15 mm, the pair of points 416B-416C being just below (e.g., 0.001 mm) the notch, and the candidate femoral implant model 320 having an anterior flange 414 with a superior edge that has a largest possible size of 37.53 mm, the maximum number of points possible with a point-spacing less than or equal to 3.15 mm is approximately 12 (i.e., 37.53/3.15=11.91≈12). Thus, as shown in FIG. 23, 12 reference points 416A-416K are employed. Of course, where anterior flanges of other sizes are employed, the number of reference points employed in the algorithm may be less than or greater than 12 equally-spaced reference points.

As can be understood from FIG. 23 and also FIGS. 25A and 25B, which are cross-sectional sagittal views of the patient femur model 226 and the candidate femoral implant model 320 thereon in no-notching and notching arrangements, respectively, the algorithm projects a vector 420 along the femur anatomical Y axis of the coordinate system 408 from each of the reference points 416A-416K to the surface boundary of the patient femur model 226. A state of "notching" is determined to occur when the following two conditions are fulfilled: (1) the length of the smallest of these vectors 420 is equal to or greater than 0 mm; and (2) the direction of the smallest of these vectors 420 is opposite to anatomical+Y of the coordinate system 408, as illustrated in FIG. 25B. Once a state of "notching" is identified, the system 100 may provide an audio and/or visual warning and the state if "notching" may be displayed to appear much like any of FIGS. 20A and/20B on the display 56.

A state of "no notching" is determined when the following two conditions are fulfilled: (1) the length of the smallest of these vectors 420 is greater than 0 mm; and (2) the direction of the smallest of these vectors 420 is the same as anatomical+Y of the coordinate system 408, as indicated in FIG. 25A. Once a state of "no notching" is identified, the system 100 may provide an audio and/or visual indication and the state of "no notching" may be displayed to appear much like FIG. 25A or a non-notching version of FIG. 20A on the display 56.

Once a surgeon has approved, or modified and approved, the proposed bone resections as preoperatively planned according to Subsection A of this Detailed Description and verified that there is no unacceptable notching of the anterior femoral cortex associated with the preoperatively planned bone resection, the lack of unacceptable notching having been verified according to Subsection B of this Detailed Description, the preoperatively planned bone resections can be intraoperatively registered with the patient's actual bone and the surgical system 100 as will now be described.

Once it is determined if notching occurs or not, the surgical system 100 may generate implant component position and orientation data based on the determined position and orientation of the femoral implant model relative to the patient femur model. The implant component position and orientation data may be employed in setting haptic boundaries for controlling a haptic device 60 or surgical robot during the arthroplasty procedure. Thus, the steps described herein may describe a method of generating implant position and orientation data for use in planning an arthroplasty procedure on a patient bone.

Other methods of notch assessment are possible such as, for example, if a line extending between 416A and 416K along the superior boundary 418 of the haptic plane intersects the solid bone of the patient femur model 226. In such a case, notching occurs if the line does intersect the solid bone of the patient femur model 226. Conversely, notching does not occur if the line does not intersect the solid bone of the patient femur model 226.

C. Checking the Closeness of Checkpoints to Resection Planes

In certain robotic assisted orthopedic procedures, intraoperative registration of the patient bone with the robotic system 100 may involve the use of removable checkpoints positioned on the patient's boney anatomy. As seen in FIG. 26A, which is a side view of a checkpoint 600, the checkpoint 600 is similar to bone anchor or screw for impacting into the bone of the patient. The checkpoint 600 may include a head end 602 at a proximal end and shaft 604 extending distally from the head end 602. The head end 602 may include an opening or divot 606 having an inner surface 608 that is conical or frusto-conical, among other shapes. The divot 604 provides for a mechanical interface with a registration instrument (e.g., navigation probe). The shaft 604 of the checkpoint 600 may include threads 610 and a distal tip 612 for rotationally driving the checkpoint 600 into a bone.

Figure 26B:
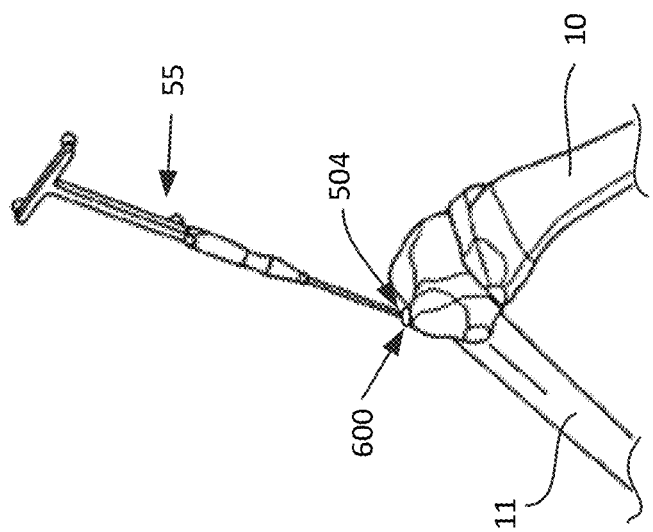
FIG. 26B is a side view of a knee joint having a checkpoint positioned on the femur with a navigation probe contacting the checkpoint.
Figure 26A:
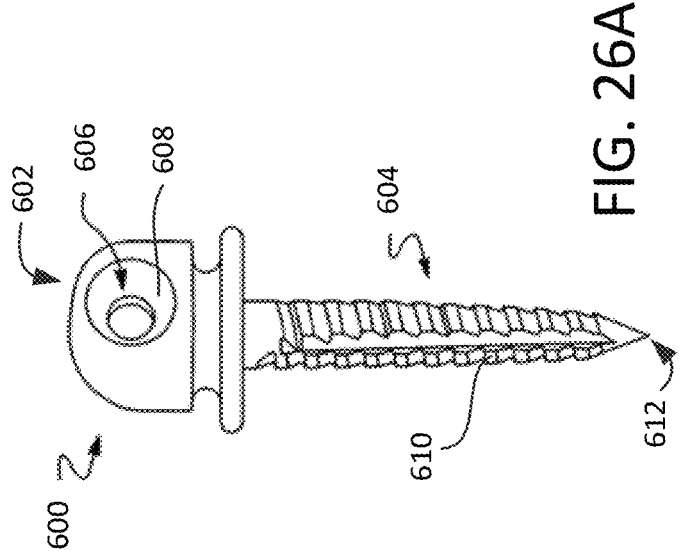
FIG. 26A is a side view of a checkpoint used in an intraoperative registration process.

As seen in FIG. 26B, which is side view of a patient's bone (tibia 10, femur 11) undergoing a checkpoint identification step in a total knee arthroplasty, the distal end 504 of the navigation probe 55 may be placed in contact with the inner surface 608 of the divot 606 on the head end 602 of the checkpoint 600 in order to positionally relate, reference, or register the femur 11 relative to other components of the surgical system 100 via the detection device 44 of the navigation system 42, as seen in FIG. 1. During checkpoint identification, the distal end 504 of the navigation probe 55 may "bottom out" at a predetermined location within the divot 606 such that the surgical system 100 can accurately position the checkpoint 600 and, thus, the patient femur 11 relative to the instrument 55 and any other devices in the surgical system 100, such as any computerized patient models 226 of the bone 11 depicted on the display 56. Aspects of checkpoint identification and checkpoints 600, among other topics, are discussed in U.S. patent application Ser. No. 11/750,807, entitled "System and method for verifying calibration of a surgical device," filed May 18, 2007, which is incorporated by reference in its entirety into the present application.

Each checkpoint 600 used during a surgical procedure must be positioned on the patient bone (e.g., femur 11) such that it is accessible during the procedure given the particular surgical approach. Additionally, each checkpoint 600 must be positioned such that it does not interfere with the procedure or the tools used during the procedure. For example, the checkpoint 600 should be located on a portion of the bone such that it will not interfere with a cutting device or be removed by a resection. The subsequently described methods and systems may aid in preoperatively determining the locations or positions of checkpoints 600 that will not interfere with the cutting tool and that will not be removed during the resections.

Figure 26C:
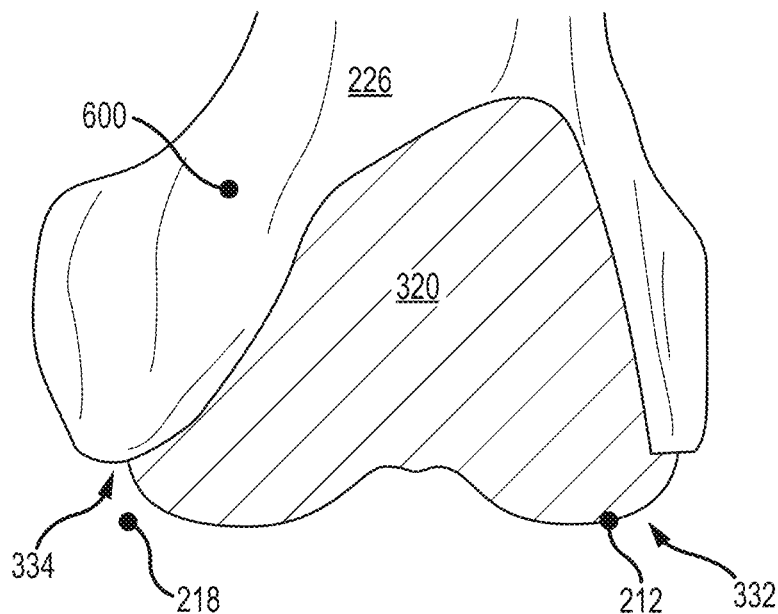
FIG. 26C illustrates a coronal view of a femur implant model superimposed on the distal end of the three dimensional computer model of the patient femur (i.e., the patient femur model) with a checkpoint positioned on the patient femur model.
Figure 26D:
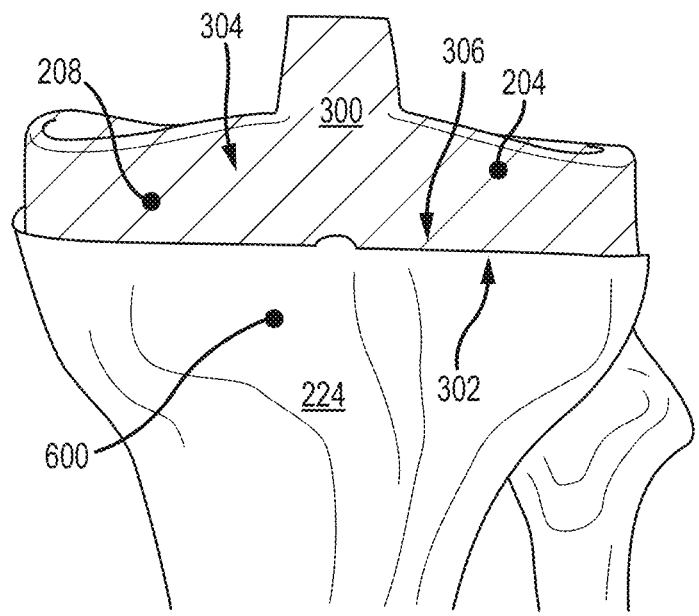
FIG. 26D illustrates a coronal view of a tibial implant model superimposed on the proximal end of the three dimensional computer model of the patient tibia (i.e., the patient tibia model) with a checkpoint positioned on the patient tibia model.
Figure 26E:
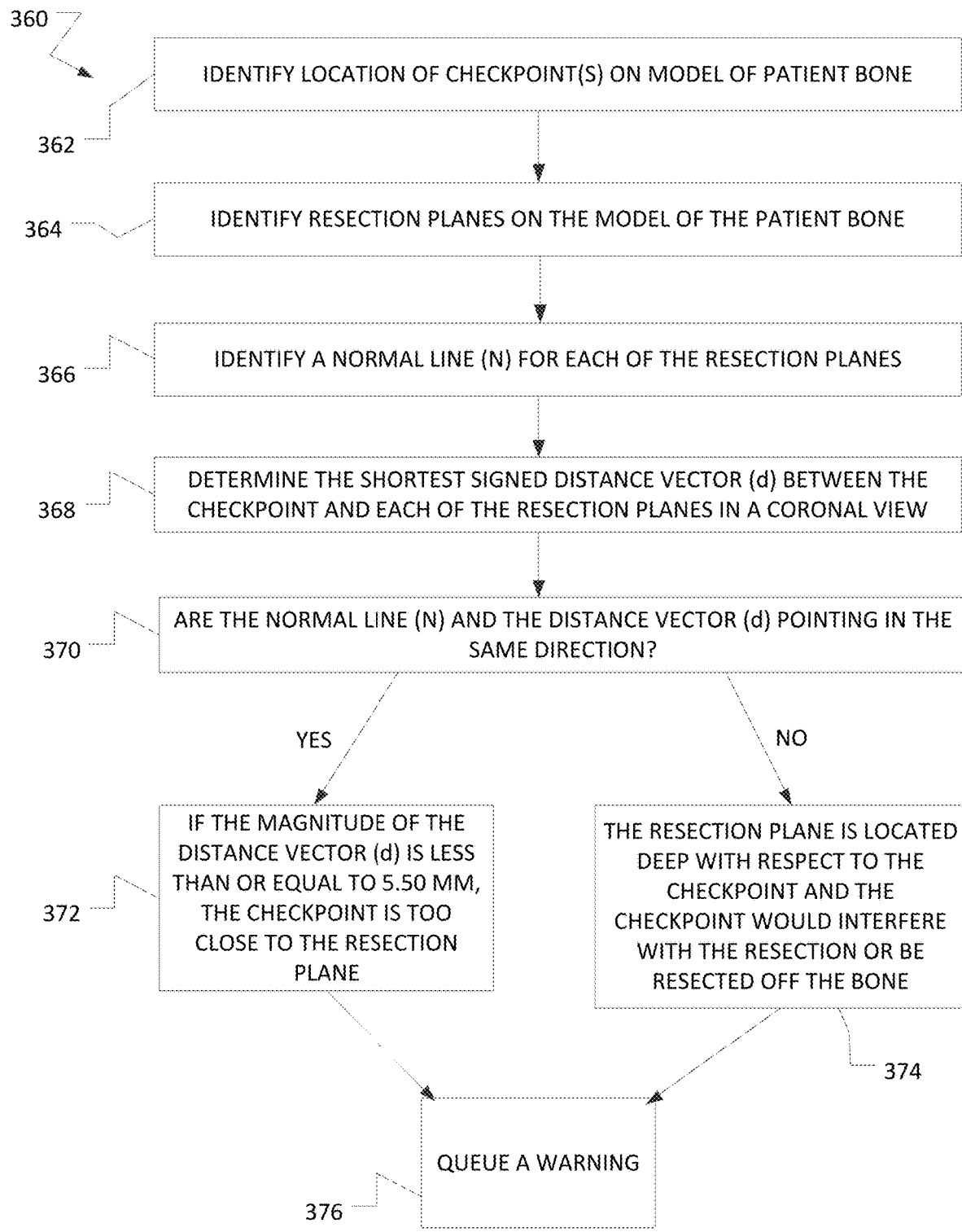
FIG. 26E illustrates steps in a checkpoint location verification process.

Reference is made to FIGS. 26C-26E, which are, respectively, the patient femur model 226 depicting the location of an implant component 320 and a checkpoint 600, a patient tibia model 224 depicting a location of an implant component 300 and a checkpoint 600, and a flow chart indicating steps in the preoperative checkpoint location verification process 360. During preoperative planning of an arthroplasty procedure, the surgeon or medical professional may identify the locations of the checkpoints 600 on the patient bone models 224, 226 [block 362]. Alternatively, the locations of the checkpoints may be automatically positioned on the patient bone models 224, 226. Preoperative planning continues as described in the previous sections by planning the types, positions, and orientations of implant components 320, 300 and resection planes 334, 306 relative to the patient bone models 224, 226 [block 364]. The checkpoint location verification process 360 may work in conjunction with the planning of the implant components 320, 300 by alerting the planner (e.g., surgeon) when the implant component 320, 300 is planned such that the associated resection plane will interfere with the checkpoint 600 in a certain way that will require an alternative location for the checkpoint 600 or an alternative placement/orientation of the implant component 320, 300. In certain instances, it may be easier to modify the location and placement of the checkpoints 600 than to modify the location and orientation of a desired implant component 320, 300. Therefore, the planner may alter the location of the checkpoints 600 such that the checkpoints 600 no longer interfere with the resection planes.

Figures 26F, 26G:
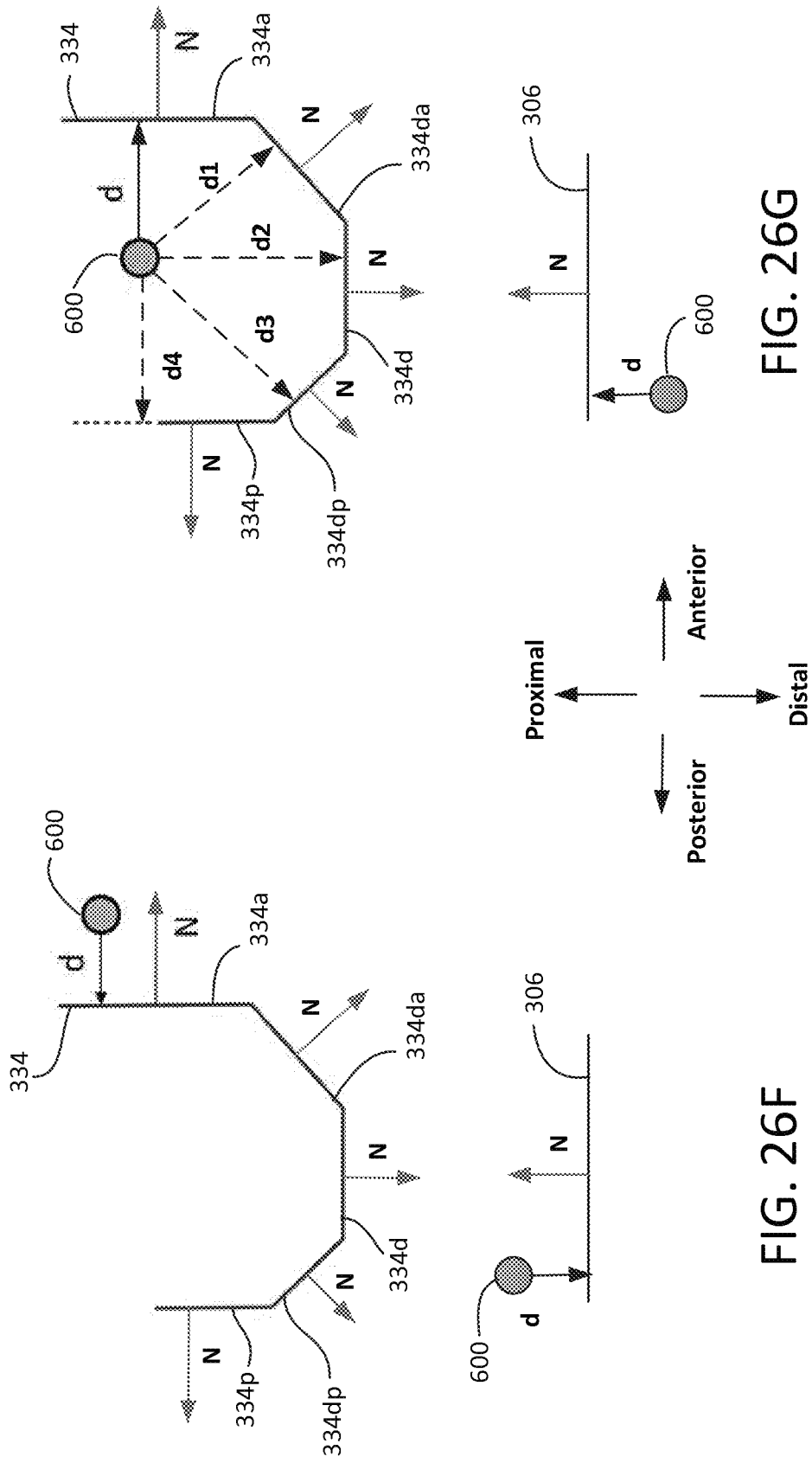
FIG. 26F is a sagittal view of the femur and tibial resection planes with the resection planes sitting "deep" with respect to the checkpoint.
FIG. 26G is a sagittal view of the femur and tibial resection planes with the resection plane sitting "proud" with respect to the checkpoint.

Continuing on, once the resection planes 334, 306 are identified at [block 364], a normal line (N) is identified for each of the resection planes [block 366], as shown in FIGS. 26F and 26G, which are, respectively, a pair of sagittal schematic views of femur resections 334 and tibial resections 306 with checkpoints 600 positioned relative to the resections 334, 306. As seen in FIGS. 26F-26G, the normal lines (N) are perpendicular to the resection planes 334, 306. Next, the shortest signed distance vector (d) is determined between the checkpoint 600 and each of the resection planes. FIGS. 26F-26G depict the shortest signed distance vector (d) in the sagittal view since the resection planes 334, 306 are orthogonal to this view, which results in the planes 334, 306 appearing as lines instead of planes.

While the shortest signed distance vector is displayed visually, the shortest signed distance vector (d) may be computed without being displayed visually. Additionally, while the shortest signed distance vector (d) in FIGS. 26F-26G is only depicted for the anterior resection 334a, the shortest signed distance vector (d) may be determined, calculated, or identified for each of the resection planes 334 (e.g., distal resection plane 334d, posterior resection plane 334p, distal-anterior chamfer resection plane 334da, and distal-posterior chamfer resection plane 334dp).

It is noted that the shortest signed distance vector (d) includes a magnitude or distance and a three-dimensional direction. The shortest signed distance vector (d) may be defined as the shortest perpendicular distance between the checkpoint 600 and a corresponding point on the associated resection plane(s) of the implant component that is coextensive with the resected surface 334 of the bone. That is, the shortest signed distance vector (d) is perpendicular to the resection plane(s) and parallel with the normal line(s) (N). As seen in FIG. 26G, the shortest signed distance vector (d4) extends to a point on the associated resection plane of the implant component that is coextensive with and positioned above the resection surface 334p.

In certain embodiments, a shortest distance vector may be used instead of a shortest signed distance vector (d). That is, in this particular embodiment, the shortest distance vector is not required to be perpendicular to the associated resection plane(s) of the implant component or the resected bone surfaces. Instead, the shortest distance vector may simply be the shortest distance vector between the checkpoint 600 and either a point on the resection plane or the resected surface 334, 306 of the bone. In some cases, the shortest distance vector may be perpendicular to the resected surface 334, 306 or the resection plane. Using a shortest distance vector may, in some instances, result in a magnitude that is less than a magnitude calculated with a shortest signed distance vector (d).

As discussed previously, the shortest distance vector may extend from the checkpoint 600 to the associated resection plane(s) or the virtually resected bone surface 334, 306. Additionally or alternatively, the shortest distance vector may extend from the checkpoint 600 to a haptic object that represents the allowable cutting perimeter of a cutting tool (e.g., saw blade). The haptic object is planar in geometry and is not infinite (i.e., unlike a resection plane). It is located at the intended resection plane but has a finite area. The perimeter of the haptic object constrains the saw blade to the intended cut and is designed to be large enough to include the saw (e.g. a blade of 25 mm wide will have a haptic object of at least 25 mm wide), shaped to remove at least the bone amount necessary to place the implant at that location, and is shaped to protect soft tissues (i.e., not infinite).

The following discussion will take place with a discussion of the shortest signed distance vector (d), but the discussion is equally applicable to a shortest distance vector as described in the previous paragraphs.

Referring back to FIG. 26E, the next step in the checkpoint location verification process 360 is to ask whether the normal line (N) and the distance vector (d), for each respective resection plane 344, are pointing in the same direction [block 370]. If the normal line (N) and the distance vector (d) are pointing in the same direction [block 372], then the resection plane is considered to be sitting "proud" with respect to the checkpoint 600. In this case, the following function is computed: if the magnitude of the distance vector (d) is less than or equal to 4.50 mm, then the location of the checkpoint 600 is too close to the resection plane 334 and the system alerts the planner with a warning [block 376], which may be an audio and/or visual indication that the location of the checkpoint 600 should be modified. If the normal line (N) and the distance vector (d) are pointing in the same direction, but the magnitude of the distance vector (d) is more than 4.50 mm, then the location of the checkpoint 600 does not need to be modified.

If the normal line (N) and the distance vector (d) are not pointing in the same direction (i.e., pointing in opposite directions), then the resection plane 334 is located "deep" with respect to the checkpoint 600 and, thus, the checkpoint 600 would interfere with the resection or be resected off of the bone during the arthroplasty procedure [block 374]. In such a case, the system alerts the planner with a warning [block 376], which may be an audio and/or visual indication that the location of the checkpoint 600 should be modified. Information associated with the checkpoint position/orientation, as well as the position/orientation of the resection planes may be used by the surgical system 100 to generate resection and checkpoint positioning data, which may be employed during the arthroplasty procedure with a haptic device 60 or surgical robot. Thus, the steps in the method described herein may describe a method of generating resection plane and checkpoint positioning data for use in planning an arthroplasty procedure on a patient bone.

Alternative methods may be used to determine whether or not the location of the checkpoint 600 is situated "deep" or "proud" without using the normal line (N). For example, the shortest signed distance vector (d) from the checkpoint 600 to the resection plane may be determined. A positive sign may indicate the checkpoint 600 is "proud" of the plane. Conversely, a negative sign for the shortest signed distance vector (d) may indicate the checkpoint 600 is "deep" or recessed from the plane.

As seen in FIG. 26F, regarding the femur resections 334, the distance vector (d) from the checkpoint 600 to the anterior resection plane 334a points in a first direction (i.e., towards the patient bone), and the normal line (N) for the anterior resection plane 334a points in a second direction (i.e., away from the patient bone), which is opposite of the first direction. Thus, as seen in [block 370] and [block 374], the resection plane is located deep with respect to the checkpoint 600 and the checkpoint 600 would interfere with the resection (e.g., contact the cutting tool) or be resected off of the bone during the arthroplasty procedure. Because of this, an alert or warning is signaled to the planner by the system to consider an alternative placement of the checkpoints 600 or implant component 320, 300. Once a determination is made that the checkpoint 600 would interfere with a cutting tool or be resected off of the bone, there may not be a need to compute the shortest signed vector (d) for other resection surfaces 334da, 334d, 334dp, 334p. Such a computation may, however, be computed in certain instances.

Regarding the tibial resection 306 in FIG. 26F, the distance vector (d) from the checkpoint 600 to the proximal tibial resection 306 points in a first direction (i.e., towards the patient bone), and the normal line (N) for the resection 306 points in a second direction (i.e., away from the patient bone), which is opposite of the first direction. Thus, as seen in [block 370] and [block 374], the resection plane is located deep with respect to the checkpoint 600 and the checkpoint 600 would interfere with the resection (e.g., contact the cutting tool) or be resected off of the bone during the arthroplasty procedure. Because of this, an alert or warning is signaled to the planner by the system to consider an alternative placement of the checkpoints 600 or implant component 320, 300.

Referring to the femur resection portion of FIG. 26G, the distance vector (d) from the checkpoint 600 to the anterior resection plane 334a points in a first direction (i.e., away from the patient bone), and the normal line (N) for the anterior resection plane 334a also points in the first direction (i.e., away from the patient bone). Since the normal line (N) and the directional portion of the distance vector (d) points in the same direction, the checkpoint location verification process 360 continues with [block 372]. According to this step in the process, the magnitude or distance portion of the distance vector (d) is analyzed according to the following equation: is magnitude of distance vector (d) less than or equal to 4.50 mm, if so, then the checkpoint 600 is too close to the resection plane 334 and an alert or warning is sent by the system to the planner [block 376]. If the magnitude of the distance vector (d) is greater than 4.50 mm, then the checkpoint 600 is adequately positioned for the arthroplasty procedure.

As seen with reference to the femur resections 334 of FIG. 26G, additional distance vectors (d1), (d2), (d3), (d4) may be analyzed in the same way that the original distance vector (d) was analyzed. As seen in the figure, all distance vectors (d1), (d2), (d3), (d4) point in the same direction as their respective normal lines (N). Thus, each distance vector (d1), (d2), (d3), (d4) is analyzed with respect to [block 372] to determine if the checkpoint 600 is too close to the respective resection plane 334da, 334d, 334dp, 334p. If one or more of the distance vectors (d1), (d2), (d3), (d4) are less than or equal to 4.50 mm from their respective resection plane 334da, 334d, 334dp, 334p, then the location of the checkpoint 600 must be modify, adjusted, or moved such that it satisfies the condition in [block 372], while not causing any of the other distance vectors (d1), (d2), (d3), (d4) to be less than or equal to 4.50 mm from the resection plane 334a, 334da, 334d, 334dp, 334p.

The rationale for the 4.50 mm threshold in [block 372] is illustrated in the table 650 of FIG. 26H. The table 650 outlines various error sources taken into account for the 4.50 mm threshold of the checkpoint 600 being too close to the resection plane. The posterior cut system error in line 1 of the table 650 refers to the maximum system error associated with a posterior resection in anatomical Y-direction (e.g., anterior-posterior direction in FIGS. 26F-26G). The maximum system error is the maximum permitted error or deviation that the system 100 will permit the user to make while conducting the posterior cut. In this particular instance, the maximum system error associated with the posterior cut in the anatomical Y-direction is illustrated by reference X1.

The distal cut system error in line 2 of the table 650 of FIG. 26H refers to the maximum system error associated with a distal resection in anatomical Z-direction (e.g., distal-proximal direction in FIGS. 26F-26G). The maximum system error is the maximum permitted error or deviation that the system 100 will permit the user to make while conducting the distal cut. In this particular instance, the maximum system error associated with the distal cut in the anatomical Z-direction is illustrated by reference X2.

Figure 26I:
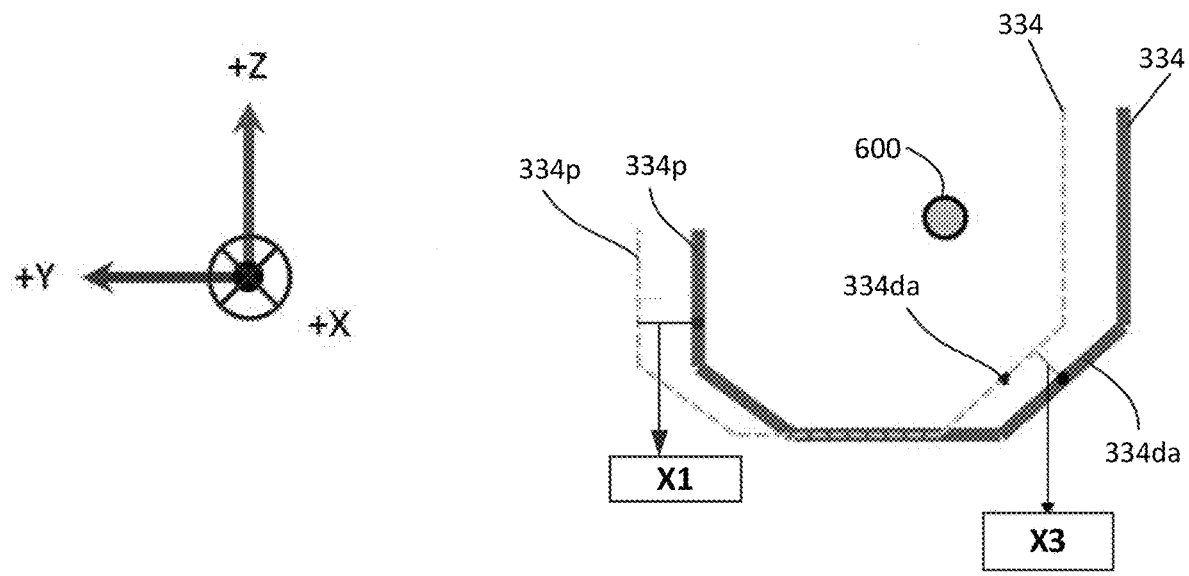
FIG. 26I is a sagittal view of the femur resection planes showing the effect of anterior chamfer error due to the error in the posterior resection.

The anterior chamfer system error due to the posterior cut, in line 3 of the table 650 in FIG. 26H, refers to the maximum system error associated with the anterior chamfer cut due to the maximum error associated with the posterior cut, discussed in reference to line 1 of the table 650. As seen in FIG. 26I, which is a sagittal view of the femur resections 334 in a first position shown in solid line and a second position shown in dotted lines after being translated, when the posterior cut is translated by in the anatomical Y-direction, the anterior chamfer cut moves closer to the checkpoint by an amount illustrated by reference X3.

Figure 26J:
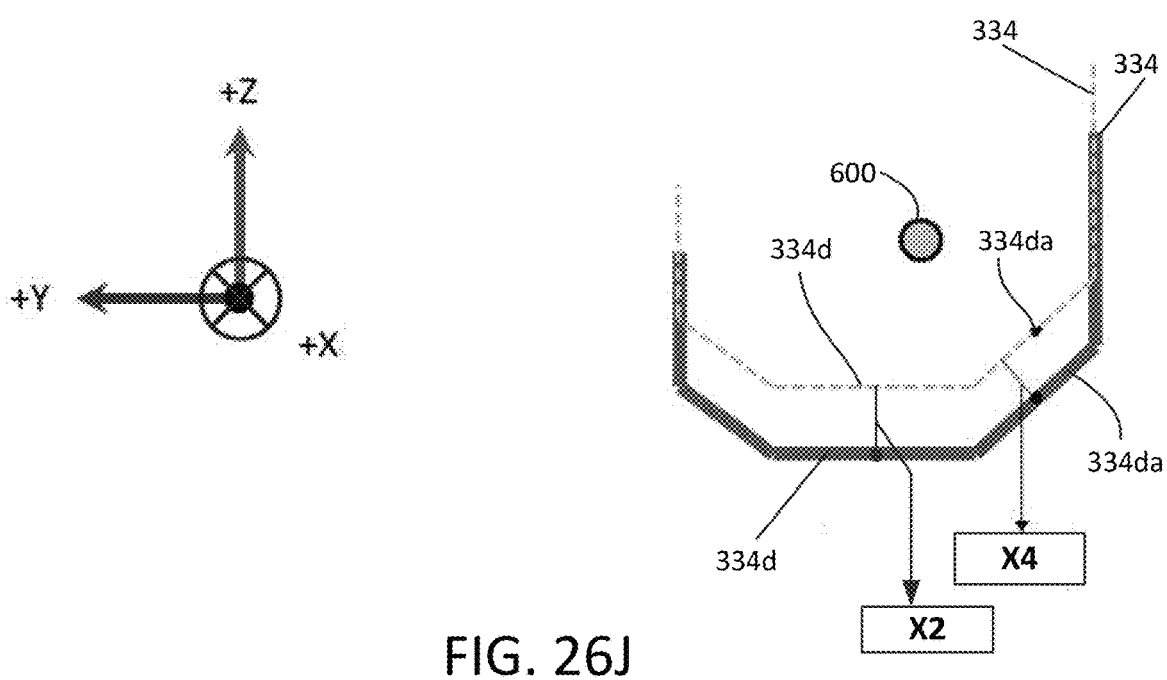
FIG. 26J is a sagittal view of the femur resection planes showing the effect of anterior chamfer error due to the error in the distal resection.

The anterior chamfer system error due to the distal cut, in line 4 of the table 650 in FIG. 26H, refers to the maximum system error associated with the anterior chamfer cut due to the maximum error associated with the distal cut, discussed in reference to line 2 of the table 650. As seen in FIG. 26J, which is a sagittal view of the femur resections 334 in a first position shown in solid line and a second position shown in dotted lines after being translated, when the distal cut is translated in the anatomical Z-direction, the anterior chamfer cut moves closer to the checkpoint by an amount illustrated by reference X4.

The profile error, illustrated by reference X5, in line 5 of the table 650 of FIG. 26H is the maximum profile error associated with the anterior chamfer cut. Profile error is the resection error associated with anterior, anterior chamfer, and posterior chamfer cuts after aligning the surgeon's distal and posterior cuts with planned distal and posterior cuts. Thus, it is an error relative to distal and posterior cuts which are assumed to be primary and secondary data for alignment purposes.

As an example, suppose a surgeon has finished all five cuts on a femur and begins trialing. Assume the distal cut is 1 mm prouder than planned and the posterior cut is 1 mm deeper than planned. When the surgeon begins trialing, the surgeon zeroes out the distal cut error by ensuring the implant component sits flushed with the resected bone on the distal plane and ensures the same on the posterior cut. With this, the surgeon transfers all of the distal and posterior cut errors onto the anterior, anterior chamfer, and posterior chamfer cuts. This type of error may be controlled by setting a bilateral tolerance band of 1.5 mm, for example, around the cuts. That is, all anterior, anterior chamfer, and posterior chamfer cuts will be within ±1.5 mm about the preoperatively planned location when distal and posterior cuts are zeroed out.

At line 6 of the table 650 of FIG. 26H, the root sum of the squares, illustrated by reference X6, which is a combined error given a list of contributing variables, is computed for the anterior chamfer error due to the posterior cut, the anterior chamfer error due to the distal cut, and the profile error. Using the values provided in the table 650, the root sum of the squares equates as follows: $RSS = SQRT((X3)^2 + (X4)^2 + (X5)^2) = X6$.

At lines 7 of the table 650 of FIG. 26H, the distance of the blade of a cutting tool from the TCP inside a checkpoint 600 is illustrated by reference X7, which in certain instances may be about 2.87 mm. This value is the shortest distance the blade of a cutting tool could be from the center point of the divot 606 (as seen in FIG. 26A) of the checkpoint 600 without contacting the checkpoint 600. Thus, the cutting tool must be spaced at least 2.87 mm, in this instance, from the tool center point (TCP) of the checkpoint 600 in order for the tool to not interfere or contact the checkpoint 600. For this calculation, it is assumed that the femoral checkpoint 600 is positioned on the femoral surface that is angled at about forty-five degrees to the sagittal plane.

As seen on the table 650 of FIG. 26H, the total threshold distance X8 is calculated by combining or adding the root sum of the squares X6, on line 6, with the blade distance factor X7, on line 7.

Referring to the tibial chart 652 of FIG. 26H, the tibial proximal cut error is illustrated by reference Y1, at line 1.

The tibial proximal cut error is the maximum system error associated with the proximal resection in the anatomical Z-direction (e.g., distal-proximal direction). That is, Y1 is the maximum allowable error that is permissible for a user in conducting the proximal resection of the tibia. In line 2 of the tibial chart 652, the blade distance factor is illustrated by reference Y2 for a tibial checkpoint 600. Given the values in lines 1 and 2 of the tibial chart 652, the sum of these values is illustrated by reference Y3 and is the total threshold distance.

The larger of the femoral and tibial checkpoint thresholds may be rounded up to 4.50 mm and used in the checkpoint location verification process 360 described herein.

III. Intraoperative Cartilage Surface Registration

In one embodiment, the three dimensional patient bone models 224, 226 are generated from CT images of the patient's actual femur and tibia. In other embodiments, the patient bone models 224, 226 are generated from other types of medical images, such as CT with contrast injection, MRI, X-ray, or etc. Some of these imaging modalities will depict the patient's cartilage (e.g., CT with contrast and MRI) and result in patient bone models that reflect the presence of the patient's cartilage and other imaging modalities (e.g., straight CT) will not, resulting in patient bone models that do not reflect the presence of the patients cartilage and are reflective of only the patient's actual cortical or outer bone surface.

In situations where straight CT images are used to generate the three dimensional patient bone models 224, 226 because CT has advantages over other imaging modalities, such as MRI, in the areas of resolution and speed, for example, the resulting CT based bone models will not reflect the patient's cartilage surface. That is, the bone models are bone-only models. Since the above-described preoperative planning involves determining bone resection depth off of the bone-only condylar surfaces of the patient bone models 224, 226, which do not reflect the patient's cartilage condylar surfaces, and since the surgical implantation of the actual femoral and tibial implants need to be positioned such that their respective condylar surfaces are located in a position that replicates the patient's native cartilage condylar surfaces being replaced as part of the total knee arthroplasty procedure, the thickness of the cartilage needs to be accounted for in the surgery.

Figure 27A:
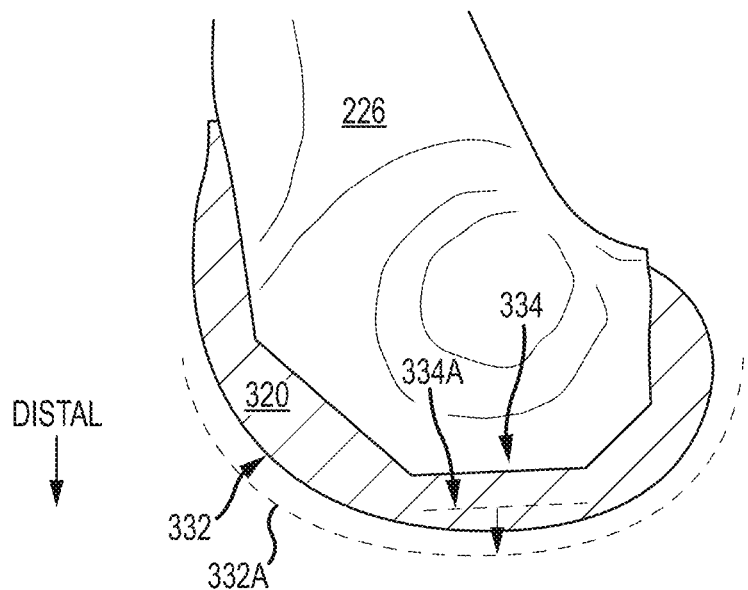
FIGS. 27A and 27B which are, respectively, a sagittal view of the femoral implant and patient bone models as preoperatively planned and a sagittal view of the tibial implant and patient bone models as preoperatively planned.
Figure 27B:
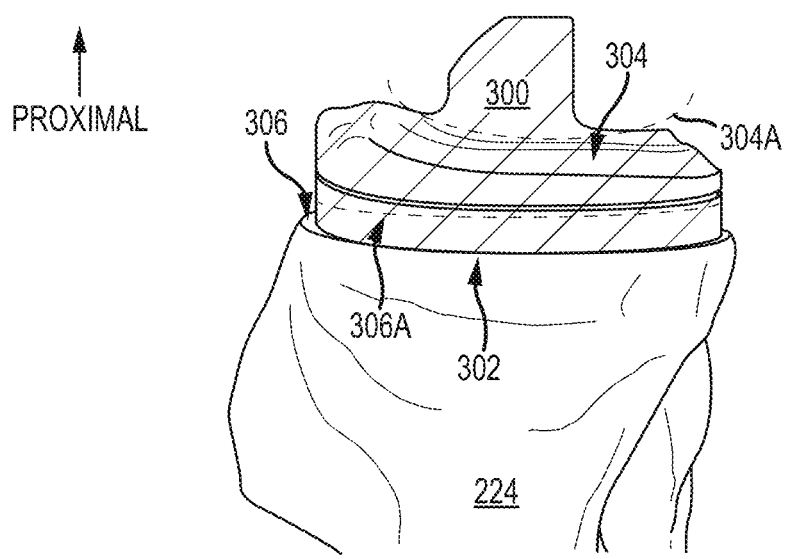

One way of accounting for the lack of cartilage representation in bone models 224, 226 generated via CT and used in the above-described preoperative planning methodology is to move the preoperatively planned femur and tibia bone resection planes 334, 302 respectively distally and proximally an amount equivalent to the cartilage thickness, as can be understood from FIGS. 27A and 27B, which are, respectively, a sagittal view of the femoral implant and patient bone models 320, 226 as preoperatively planned and a sagittal view of the tibial implant and patient bone models 300, 224 as preoperatively planned. As indicated by the dashed arrows in FIG. 27A, the preoperatively planned location of the femoral implant condylar surface 332 moves distally to assume a cartilage compensated location 332A of the femoral implant condylar surface, and the preoperatively planned location of the femoral resection 334 moves distally to assume a cartilage compensated location 334A of the femoral resection. The result of such an adjustment will cause the actual femoral implant to have its condylar surface located so as to act in place of the resected femoral cartilage condylar surface.

As shown by the dashed arrows in FIG. 27B, the preoperatively planned location of the tibial implant condylar surface 304 moves proximally to assume a cartilage compensated location 304A of the tibial implant condylar surface, and the preoperatively planned location of the tibial resection 306 moves proximally to assume a cartilage compensated location 306A of the tibial resection. The result of such an adjustment will cause the actual tibial implant to have its condylar surface located so as to act in place of the resected tibial cartilage condylar surface.

In one embodiment, the cartilage compensation can be made by making the moves shown in FIGS. 27A and 27B according to an estimated value for cartilage thickness. For example, the femoral and tibia preoperatively planned resections could be moved their respective directions an estimated cartilage thickness of, for example, 2 mm.

In another embodiment, the cartilage compensation can be made during an intraoperative registration process as will now be discussed. As discussed above with respect to FIG. 1, during the actual surgery, the actual patient bones 10, 11 are positionally registered to the corresponding patient bone models 224, 226 via navigation markers 46 affixed to the patient bones 10, 11 and detected via the detection device 44 of the navigation system 42. On account of the intraoperative registration of the actual bones 10, 11 to the bone models 224, 226, the system 100 knows where the bone model condylar surfaces are relative to those of the actual bones 10, 11. However, since the bone models are the result of CT imaging, the cartilage condylar surfaces were not part of the preoperative planning, and the system 100 does not know where the cartilage condylar surface is in relation to those of the actual bones or bone models. Registration of the cartilage can remedy this situation.

Figure 28A:
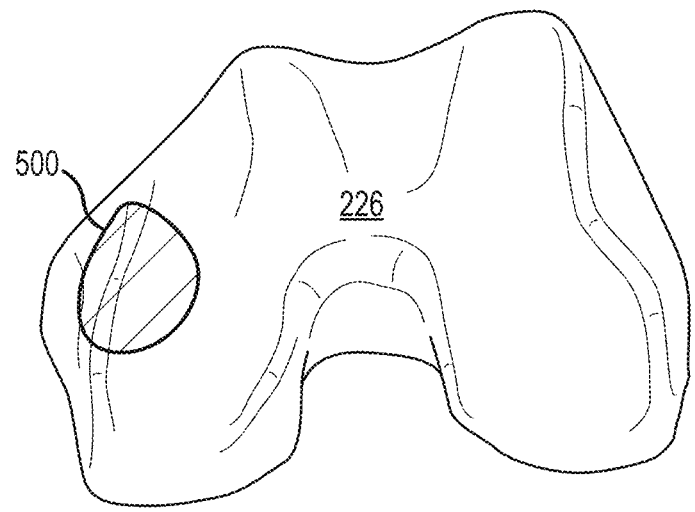
FIGS. 28A and 28B are, respectively, an axial or transverse view and a posterior view of the patient femoral model as depicted on the display of the system in FIG. 1.
Figure 28B:
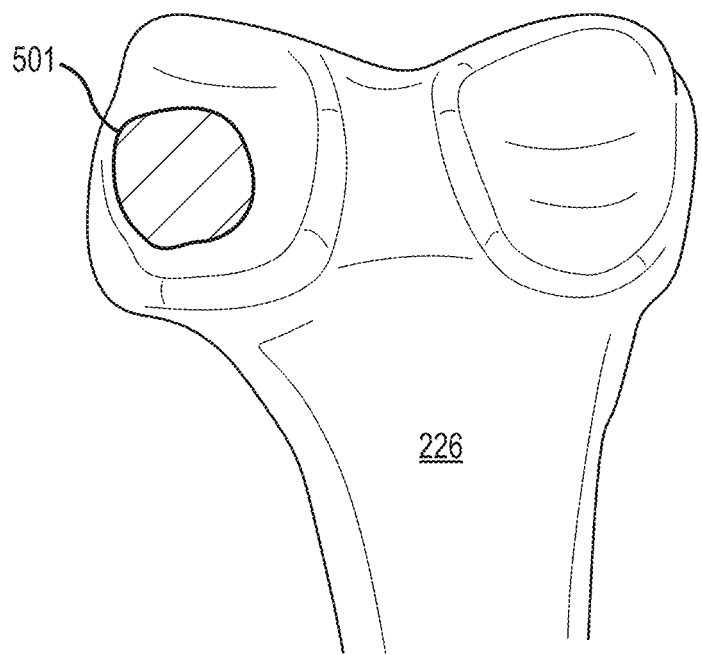

FIGS. 28A and 28B are, respectively, an axial or transverse distal view and a coronal posterior view of the patient femoral model 226 as depicted on the display 56 of the system in FIG. 1. Landmark capture regions 500, 501 are highlighted on the model 226 in each view. The landmark capture regions pertain to regions on the actual patient femur 11 that can be identified by the surgeon intraoperatively.

Figure 29A:
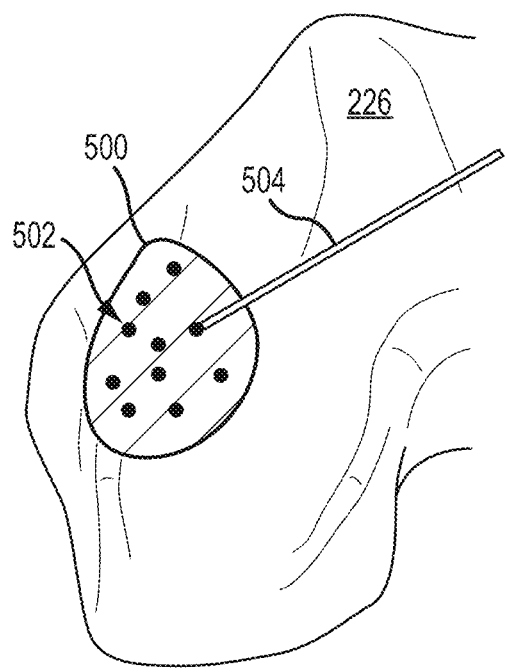
FIGS. 29A and 29B are, respectively, enlarged views of the landmark capture regions of FIGS. 28A and 28B, respectively, wherein a series of registration points are depicted on each capture region.
Figure 29B:
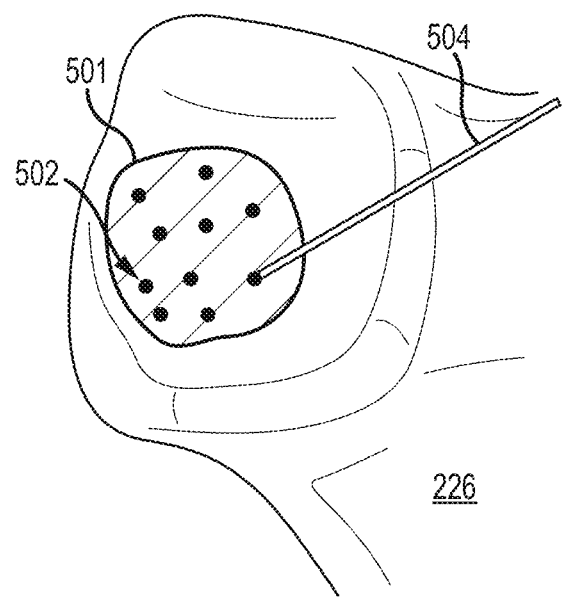

FIGS. 29A and 29B are, respectively, enlarged views of the landmark capture regions 500, 501 of FIGS. 28A and 28B, respectively, wherein a series of registration points 502 are depicted on each capture region. In one embodiment, each region 500, 501 has ten points 502 thereon, and in other embodiments, the number of points 502 can be greater or less than 10.

As can be understood from FIG. 1 and FIGS. 29A and 29B, a distal end 504 of the navigation probe 55 or the distal end 504 of a capture probe extending from the free end of the end effector of the haptic device 60 (i.e., the part of the haptic device 60 that is shown as occupied by the surgical tool 58 in FIG. 1) is guided by the surgeon to contact the actual cartilage condyle surface of the patient's actual femur 11 intraoperatively at locations the surgeon believes to be the same as the points 502 in regions 500 and 501 shown on the display in FIGS. 29A and 29B. Each time the surgeon touches the cartilage condylar surface of the patient's actual femur 11 in a location believed to correspond with one of the points 502 displayed on the display 56, the surgeon makes an input into the system 100, which then registers that actual cartilage point location and the corresponding point 502 show on the display 56. This process is repeated until all ten points 502 are registered to corresponding point locations on the cartilage condylar surface of the actual patient femur 11. While the process is described as registering individual points on the cartilage surface that correspond with specific points shown on the bone models, the system 100 may alternatively display a target region only and not depict individual points for capturing.

As a result of the capturing process, the cartilage condylar surface of the actual patient femur is now registered to the patient femur model 226 on account of the patient femur model being already registered to the actual patient femur 11. As an alternative to individually inputting each point 502 into the system 100 with separate discreet actions by the surgeon or member of the surgical team, the capture process may be initiated by a single input (e.g., button click on screen, foot pedal input, button press on navigation probe 55), then the surgeon may "paint" the region 500, 501 while the system automatically inputs the location of the distal end 504 of the navigation probe 55 on the bone surface. Thus, the system may collect the ten points in a short amount of time with only a single input signal provided by the surgeon or surgical team.

Returning to FIG. 27A with the cartilage condylar surface being registered relative to the patient bone model 226 as described and with the location of the cartilage condylar surface being represented by the dashed line 332A, the system 100 moves the implant condylar surface 332 distally to positionally coincide with the cartilage condylar surface line 332A, thereby pulling the preoperatively planned resection line 334 to the intraoperatively adjusted resection line 334A. Thus, the preoperatively planned resection line has been adjusted intraoperatively via registration of the cartilage condylar surface of the actual patient femur 11 to the patient femur model 226 via the described registration process.

Once the cartilage condylar surface is registered, the preoperatively planned resection may be adjusted or determined by moving the implant condylar surface distally an amount that equals the difference between the articular surface of the three-dimensional bone-only model and the mapped cartilage surface in a particular direction.

While the registration line for the cartilage condylar surface 332A is depicted in FIG. 27A as being a line, in some embodiments, the cartilage offset information may simply be in the form of a point or other reference that is offset from the condylar surface of the femur model 226 by the registered thickness of the cartilage region 500 being registered. In certain embodiments, the system 100 may only depict a single point that is the lowest/most distal/most posterior/most proximal depending on the particular bone region of interest. In certain embodiments, all or a portion of all of the points 502 may be used to interpolate a surface and the system 100 may move the implant condylar surface 332 to the interpolated surface.

Once the resection depth is adjusted based on the cartilage thickness, the surgeon may accept the change or modify the implant plan.

While the preceding cartilage registration discussion takes place in the context of the femoral intraoperative cartilage registration and resection adjustment, the preceding discussion is equally applicable to the tibial intraoperative cartilage registration and resection adjustment, as can be understood from a comparison of FIGS. 27A, 28A and 29A to FIGS. 27B, 28B and 29B.

On account of having the preoperatively planned resections adjusted to account for cartilage thickness via the above-described cartilage registration process, the implanted implants may have their respective condylar surfaces located so as to act in place of the resected cartilage condylar surfaces. In other embodiments, the implanted implants may have only one condylar surface (e.g., medial or lateral) located so as to act in place of the resected cartilage condylar surface. In other embodiments, the implanted implants may not have any condylar surface (e.g., medial or lateral) located so as to act in place of the resected cartilage condylar surface.

The intra-operative cartilage registration process may be described as a process or method of generating resection data for use in planning a knee arthroplasty. Since the patient bone model 226, 224 may depict bone only, in certain embodiments, and the actual patient bone may be covered at least partially in cartilage, intra-operative registration of the cartilage may provide insight into an amount of adjustment to the resection depth, which may be determined preoperatively with or without additional or alternative considerations of cartilage.

The process or method may generally be described as follows. A computer of the system may receive a three-dimensional patient bone model 226, 224 (e.g., femur model, tibia model) generated from medical images (e.g., CT, MRI, X-ray) of the patient bone (e.g., femur, tibia). The three-dimensional patient bone model 226, 224 may include a bone model surface corresponding to the shape and patient-specific contours of the actual patient bone. The three-dimensional patient bone model 226, 224 may be correlated with a position and orientation of the actual patient bone via the tracking and navigation system described in reference to FIG. 1. The three-dimensional patient bone model 226, 224 may be positioned in a three-dimensional coordinate system or space.

The method or process may also include identifying a location of a first plurality of points 502 within a target region 500, 501 on the bone model surface of the three-dimensional patient bone model 226, 224 for intra-operative registration by a surgeon with a distal end 504 of a navigation probe 55. The method or process may also include receiving location data for a second plurality of points based on the intra-operative registration of the cartilage on the actual, physical patient bone in locations corresponding to the first plurality of points 502 on the bone model surface of the three-dimensional bone model 226, 224.

The method or process may also include determining a resection depth based on a comparison between the location data for the second plurality of point and the location of the first plurality of points on the bone model surface. The method or process may also include generating resection data using the resection depth. The resection data may be employed as a haptic boundary for controlling the surgical robot of FIG. 1. Additionally or alternatively, the resection data may be utilized by a surgical robot during the arthroplasty procedure. Additionally or alternatively, the resection data may be utilized by a navigation system during the arthroplasty procedure. The navigation system may operate in conjunction with an autonomous robot or a surgeon-assisted device in performing the arthroplasty procedure. An autonomous robot, such as a cutting device with at least two degrees of freedom (e.g., rotating burr and translation capabilities) may perform the arthroplasty procedure with the resection data utilized as a tool path for performing a resection. A surgeon-assisted device, such as the haptic device 60 described herein or a cutting tool with at least one degree of freedom (e.g., rotating burr moved or translated by a surgeon), may perform the arthroplasty procedure with the resection data being a virtual or haptic boundary for controlling or limiting certain movements of the cutting tool (e.g., depth of resection).

An example of the method described herein may involve generating resection data for use in planning an arthroplasty procedure on a patient bone covered at least partially in cartilage. The method may include a computer receiving a three-dimensional patient bone model including a bone model surface, the three-dimensional patient bone model correlated with a position and orientation of the patient bone via a navigation system. The three-dimensional patient bone model being in a three-dimensional coordinate system. The computer may identify a target region on the bone model surface of the three-dimensional patient bone model for intra-operative registration. The computer may also receive location data for a first plurality of points based on the intra-operative registration of the cartilage on the patient bone in locations corresponding to points within the target region on the bone model surface of the three-dimensional bone model. The computer may also determine a resection depth based at least in part on the location data for the first plurality of point. The computer may also generate resection data using the resection depth, the resection data configured to be utilized by the navigation system during the arthroplasty procedure.

Figure 30:
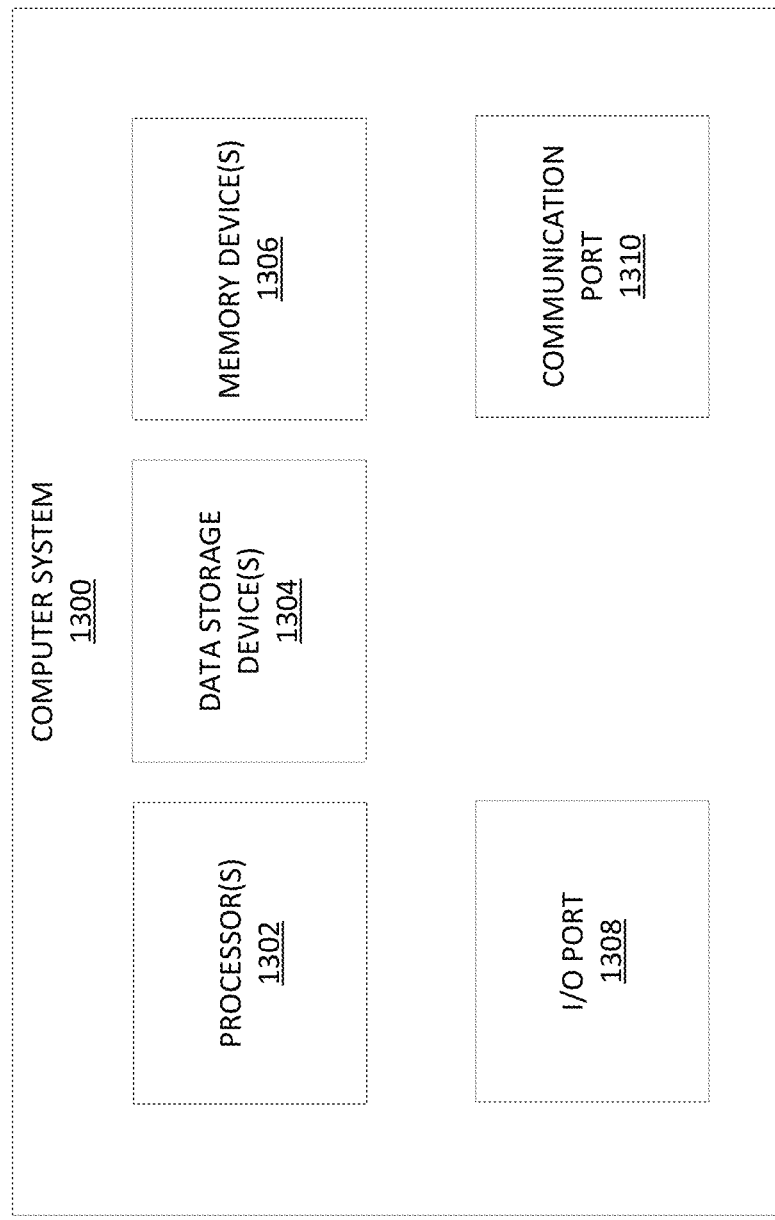
FIG. 30 is an example computing system having one or more computing units that may implement various systems and methods discussed herein is provided.

Referring to FIG. 30, a detailed description of an example computing system 1300 having one or more computing units that may implement various systems and methods discussed herein is provided. The computing system 1300 may be applicable to any of the computers or systems utilized in the preoperative planning of the arthroplasty procedure, and other computing or network devices. It will be appreciated that specific implementations of these devices may be of differing possible specific computing architectures not all of which are specifically discussed herein but will be understood by those of ordinary skill in the art.

The computer system 1300 may be a computing system that is capable of executing a computer program product to execute a computer process. Data and program files may be input to the computer system 1300, which reads the files and executes the programs therein. Some of the elements of the computer system 1300 are shown in FIG. 30, including one or more hardware processors 1302, one or more data storage devices 1304, one or more memory devices 1308, and/or one or more ports 1308-1310. Additionally, other elements that will be recognized by those skilled in the art may be included in the computing system 1300 but are not explicitly depicted in FIG. 30 or discussed further herein. Various elements of the computer system 1300 may communicate with one another by way of one or more communication buses, point-to-point communication paths, or other communication means not explicitly depicted in FIG. 30.

The processor 1302 may include, for example, a central processing unit (CPU), a microprocessor, a microcontroller, a digital signal processor (DSP), and/or one or more internal levels of cache. There may be one or more processors 1302, such that the processor 1302 comprises a single central-processing unit, or a plurality of processing units capable of executing instructions and performing operations in parallel with each other, commonly referred to as a parallel processing environment.

The computer system 1300 may be a conventional computer, a distributed computer, or any other type of computer, such as one or more external computers made available via a cloud computing architecture. The presently described technology is optionally implemented in software stored on the data stored device(s) 1304, stored on the memory device(s) 1306, and/or communicated via one or more of the ports 1308-1310, thereby transforming the computer system 1300 in FIG. 30 to a special purpose machine for implementing the operations described herein. Examples of the computer system 1300 include personal computers, terminals, workstations, mobile phones, tablets, laptops, personal computers, multimedia consoles, gaming consoles, set top boxes, and the like.

The one or more data storage devices 1304 may include any non-volatile data storage device capable of storing data generated or employed within the computing system 1300, such as computer executable instructions for performing a computer process, which may include instructions of both application programs and an operating system (OS) that manages the various components of the computing system 1300. The data storage devices 1304 may include, without limitation, magnetic disk drives, optical disk drives, solid state drives (SSDs), flash drives, and the like. The data storage devices 1304 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1306 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1304 and/or the memory devices 1306, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1300 includes one or more ports, such as an input/output (I/O) port 1308 and a communication port 1310, for communicating with other computing, network, or vehicle devices. It will be appreciated that the ports 1308-1310 may be combined or separate and that more or fewer ports may be included in the computer system 1300.

The I/O port 1308 may be connected to an I/O device, or other device, by which information is input to or output from the computing system 1300. Such I/O devices may include, without limitation, one or more input devices, output devices, and/or other devices.

In one implementation, the input devices convert a human-generated signal, such as, human voice, physical movement, physical touch or pressure, and/or the like, into electrical signals as input data into the computing system 1300 via the I/O port 1308. Similarly, the output devices may convert electrical signals received from computing system 1300 via the I/O port 1308 into signals that may be sensed as output by a human, such as sound, light, and/or touch. The input device may be an alphanumeric input device, including alphanumeric and other keys for communicating information and/or command selections to the processor 1302 via the I/O port 1308. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

In one implementation, a communication port 1310 is connected to a network by way of which the computer system 1300 may receive network data useful in executing the methods and systems set out herein as well as transmitting information and network configuration changes determined thereby. Stated differently, the communication port 1310 connects the computer system 1300 to one or more communication interface devices configured to transmit and/or receive information between the computing system 1300 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1310 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1310 may communicate with an antenna or other link for electromagnetic signal transmission and/or reception.

In an example implementation, patient data, bone models (e.g., generic, patient specific), transformation software, and other software and other modules and services may be embodied by instructions stored on the data storage devices 1304 and/or the memory devices 1306 and executed by the processor 1302. The computer system 1300 may be integrated with or otherwise form part of the surgical system 100.

The system set forth in FIG. 30 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed herein, for example, those shown in FIGS. 8, 10A-10C, 18-19, and 26E, among others, may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure including any of the methods described herein may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A method of generating implant position and orientation data for use in planning an arthroplasty procedure on a patient bone comprising a lateral femur area, proximal femur area, and a posterior femur area, the method comprising:

obtaining patient data associated with at least a portion of the patient bone;

generating a three-dimensional patient femur model from the patient data, the patient femur model comprising a surface boundary and a cortex region, the patient femur model being in a three-dimensional coordinate system with an X-axis in a medial-lateral direction, a Y-axis in an anterior-posterior direction with the +Y-axis pointing towards the posterior femur area, and a Z-axis in a superior-inferior direction with the +Z axis pointing towards the proximal femur area;

obtaining a three-dimensional femoral implant model comprising an anterior flange portion having a superior edge and an anterior bone resection contact surface being planar and adjacent the superior edge;

determining a position and orientation of the femoral implant model relative to the patient femur model;

extending a haptic plane coplanar with the anterior bone resection contact surface, the haptic plane comprising a superior boundary positioned superior of the superior edge of the anterior flange portion of the femoral implant model;

identifying a series of points on the superior boundary of the haptic plane;

projecting a vector along the Y-axis from each of the series of points to a corresponding surface of the surface boundary of the patient femur model;

determining that notching occurs based on a length and a direction of a smallest of the vectors; and generating implant component position and orientation data based on the determined position and orientation of the femoral implant model relative to the patient femur model, the implant component position and orientation data configured to be utilized by a navigation system during the arthroplasty procedure.

2. The method of claim 1, wherein notching occurs when: the length of the smallest of the vectors is equal to or greater than 0 mm; and the direction of the smallest of the vectors is opposite of the +Y-axis of the coordinate system.

3. The method of claim 1, wherein no notching occurs when: the length of the smallest of the vectors is greater than 0 mm; and the direction of the smallest of the vectors is in a same direction as the +Y-axis of the coordinate system.

4. The method of claim 1, wherein the length is based on a perceivable depth of notching.

5. The method of claim 1, wherein the series of points are equally spaced along the superior boundary of the haptic plane.

6. The method of claim 5, wherein the series of points are equally spaced based upon a radius of curvature at or near the cortex region of the patient femur model.

7. The method of claim 5, wherein the series of points are equally spaced based upon a clinically relevant depth of perceivable notching.

8. The method of claim 5, wherein the series of points are equally spaced based upon: a radius of curvature at or near the cortex region of the patient femur model; and a clinically relevant depth of perceivable notching.

9. The method of claim 1, wherein the series of points are equally spaced about 3.15 mm apart.

10. The method of claim 1, wherein the patient data is captured using a medical imaging machine.

11. The method of claim 1, wherein the navigation system operates in conjunction with an autonomous robot or a surgeon-assisted device in performing the arthroplasty procedure.

12. A method of generating implant position and orientation data for use in planning an arthroplasty procedure on a patient bone comprising a lateral femur area, proximal femur area, and a posterior femur area, the method comprising:

obtaining patient data associated with at least a portion of the patient bone, the patient data captured using a medical imaging machine;

generating a three-dimensional patient femur model from the patient data, the three-dimensional patient femur model comprising a surface boundary;

obtaining a three-dimensional femoral implant model comprising an anterior flange portion having an associated haptic resection object having a superior boundary edge;

determining a position and orientation of the femoral implant model relative to the patient femur model;

projecting a vector from each of a series of points on the superior boundary edge of the haptic resection object to a corresponding surface on the surface boundary of the patient femur model;

determining that notching occurs based on a length and a direction of a smallest of the vectors; and generating implant component position and orientation data based on the determined position and orientation of the femoral implant model relative to the patient femur model, the implant component position and orientation data configured to be utilized by a navigation system during the arthroplasty procedure.

13. The method of claim 12, wherein the three-dimensional patient femur model further comprises a cortex region, the patient femur model being in a three-dimensional coordinate system with an X-axis in a medial-lateral direction, a Y-axis in an anterior-posterior direction with the +Y-axis pointing towards the posterior femur area, and a Z-axis in a superior-inferior direction with the +Z axis pointing towards the proximal femur area; the method further comprising:

identifying the series of points on the superior boundary edge of the haptic resection object.

14. The method of claim 13, wherein notching occurs when: the length of the smallest of the vectors is equal to or greater than 0 mm; and the direction of the smallest of the vectors is opposite of the +Y-axis of the coordinate system.

15. The method of claim 13, wherein no notching occurs when: the length of the smallest of the vectors is greater than 0 mm; and the direction of the smallest of the vectors is in a same direction as the +Y-axis of the coordinate system.

16. The method of claim 13, wherein the length is based on a perceivable depth of notching.

17. The method of claim 13, wherein the series of points are equally spaced along the superior boundary edge.

18. The method of claim 17, wherein the series of points are equally spaced based upon a radius of curvature at or near the cortex region of the patient femur model.

19. The method of claim 17, wherein the series of points are equally spaced based upon a clinically relevant depth of perceivable notching.

20. The method of claim 17, wherein the series of points are equally spaced based upon: a radius of curvature at or near the cortex region of the patient femur model; and a clinically relevant depth of perceivable notching.

21. The method of claim 13, wherein the series of points are equally spaced about 3.15 mm apart.

22. The method of claim 12, wherein the navigation system operates in conjunction with an autonomous robot or a surgeon-assisted device in performing the arthroplasty procedure.

* * * * *

UNITED STATES PATENT AND TRADEMARK OFFICE
CERTIFICATE OF CORRECTION

PATENT NO. : 11,229,485 B2
APPLICATION NO. : 16/436102
DATED : January 25, 2022
INVENTOR(S) : Otto et al.

It is certified that error appears in the above-identified patent and that said Letters Patent is hereby corrected as shown below:

In the Claims

Replace all the Claims beginning in Column 54, Line 55 - Column 56, Line 62 with the following:

1. A method of generating implant component position and orientation data for use in planning an arthroplasty procedure on a patient bone comprising a lateral femur area, proximal femur area, and a posterior femur area, the method comprising:
obtaining patient data associated with at least a portion of the patient bone;
generating a three-dimensional patient femur model from the patient data, the three-dimensional patient femur model comprising a surface boundary and a cortex region, the three-dimensional patient femur model being in a three-dimensional coordinate system with an X-axis in a medial-lateral direction, a Y-axis in an anterior-posterior direction with the +Y-axis pointing towards the posterior femur area, and a Z-axis in a superior-inferior direction with the +Z axis pointing towards the proximal femur area;
obtaining a three-dimensional femoral implant model comprising an anterior flange portion having a superior edge and an anterior bone resection contact surface being planar and adjacent the superior edge;
determining a position and orientation of the three-dimensional femoral implant model relative to the three-dimensional patient femur model;
extending a haptic plane coplanar with the anterior bone resection contact surface, the haptic plane comprising a superior boundary positioned superior of the superior edge of the anterior flange portion of the three-dimensional femoral implant model;
    identifying a series of points on the superior boundary of the haptic plane;
    projecting a vector along the Y-axis from each of the series of points to a corresponding
        surface of the surface boundary of the three-dimensional patient femur model;
    determining that notching occurs based on a length and a direction of a smallest of the
        vectors; and
    generating the implant component position and orientation data based on the determined
        position and orientation of the three-dimensional femoral implant model relative Signed and Sealed this
Twenty-eighth Day of May, 2024

*Katherine Kelly Vidal*

Katherine Kelly Vidal
*Director of the United States Patent and Trademark Office* to the three-dimensional patient femur model, the implant component position and orientation data configured to be utilized by a navigation system during the arthroplasty procedure.

2. The method of claim 1, wherein notching occurs when: the length of the smallest of the vectors is equal to or greater than 0 mm; and the direction of the smallest of the vectors is opposite of the +Y-axis of the three-dimensional coordinate system.

3. The method of claim 1, wherein no notching occurs when: the length of the smallest of the vectors is greater than 0 mm; and the direction of the smallest of the vectors is in a same direction as the +Y-axis of the three-dimensional coordinate system.

4. The method of claim 1, wherein the length is based on a perceivable depth of notching.

5. The method of claim 1, wherein the series of points are equally spaced along the superior boundary of the haptic plane.

6. The method of claim 5, wherein the series of points are equally spaced based upon a radius of curvature at or near the cortex region of the three-dimensional patient femur model.

7. The method of claim 5, wherein the series of points are equally spaced based upon a clinically relevant depth of perceivable notching.

8. The method of claim 5, wherein the series of points are equally spaced based upon: a radius of curvature at or near the cortex region of the three-dimensional patient femur model; and a clinically relevant depth of perceivable notching.

9. The method of claim 1, wherein the series of points are equally spaced about 3.15 mm apart.

10. The method of claim 1, wherein the patient data is captured using a medical imaging machine.

11. The method of claim 1, wherein the navigation system operates in conjunction with an autonomous robot or a surgeon-assisted device in performing the arthroplasty procedure.

12. A method of generating implant component position and orientation data for use in planning an arthroplasty procedure on a patient bone comprising a lateral femur area, proximal femur area, and a posterior femur area, the method comprising:
    obtaining patient data associated with at least a portion of the patient bone, the patient data captured using a medical imaging machine;
    generating a three-dimensional patient femur model from the patient data, the three-dimensional patient femur model comprising a surface boundary;
    obtaining a three-dimensional femoral implant model comprising an anterior flange portion having an associated haptic resection object having a superior boundary edge;
    determining a position and orientation of the three-dimensional femoral implant model relative to the three-dimensional patient femur model;

projecting a vector from each of a series of points on the superior boundary edge of the haptic resection object to a corresponding surface on the surface boundary of the three-dimensional patient femur model;

determining that notching occurs based on a length and a direction of a smallest of the vectors; and generating the implant component position and orientation data based on the determined position and orientation of the three-dimensional femoral implant model relative to the three-dimensional patient femur model, the implant component position and orientation data configured to be utilized by a navigation system during the arthroplasty procedure.

13. The method of claim 12, wherein the three-dimensional patient femur model further comprises a cortex region, the three-dimensional patient femur model being in a three-dimensional coordinate system with an X-axis in a medial-lateral direction, a Y-axis in an anterior-posterior direction with the +Y-axis pointing towards the posterior femur area, and a Z-axis in a superior-inferior direction with the +Z axis pointing towards the proximal femur area; the method further comprising:

identifying the series of points on the superior boundary edge of the haptic resection object.

14. The method of claim 13, wherein notching occurs when: the length of the smallest of the vectors is equal to or greater than 0 mm; and the direction of the smallest of the vectors is opposite of the +Y-axis of the three-dimensional coordinate system.

15. The method of claim 13, wherein no notching occurs when: the length of the smallest of the vectors is greater than 0 mm; and the direction of the smallest of the vectors is in a same direction as the +Y-axis of the three-dimensional coordinate system.

16. The method of claim 13, wherein the length is based on a perceivable depth of notching.

17. The method of claim 13, wherein the series of points are equally spaced along the superior boundary edge.

18. The method of claim 17, wherein the series of points are equally spaced based upon a radius of curvature at or near the cortex region of the three-dimensional patient femur model.

19. The method of claim 17, wherein the series of points are equally spaced based upon a clinically relevant depth of perceivable notching.

20. The method of claim 17, wherein the series of points are equally spaced based upon: a radius of curvature at or near the cortex region of the three-dimensional patient femur model; and a clinically relevant depth of perceivable notching.

21. The method of claim 13, wherein the series of points are equally spaced about 3.15 mm apart.

22. The method of claim 12, wherein the navigation system operates in conjunction with an autonomous robot or a surgeon-assisted device in performing the arthroplasty procedure.